United States Patent
Wolters et al.

(10) Patent No.: US 10,172,718 B2
(45) Date of Patent: Jan. 8, 2019

(54) EXPANDABLE INTERBODY AND INTRAVERTEBRAL BODY DEVICES

(71) Applicant: Life Spine, Inc., Huntley, IL (US)

(72) Inventors: Madeline Wolters, Carol Stream, IL (US); Daniel Predick, Chicago, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/797,978

(22) Filed: Oct. 30, 2017

(65) Prior Publication Data

US 2018/0133024 A1    May 17, 2018

Related U.S. Application Data

(60) Continuation of application No. 14/714,821, filed on May 18, 2015, now Pat. No. 9,801,733, which is a
(Continued)

(51) Int. Cl.
| | |
|---|---|
| *A61F 2/44* | (2006.01) |
| *A61B 17/88* | (2006.01) |
| *A61F 2/30* | (2006.01) |

(52) U.S. Cl.
CPC ........ *A61F 2/4425* (2013.01); *A61B 17/8858* (2013.01); *A61F 2/44* (2013.01);
(Continued)

(58) Field of Classification Search
CPC . A61B 17/68; A61B 17/70; A61F 2/44; A61F 2/442; A61F 2/4425; A61F 2/4455
See application file for complete search history.

(56) References Cited

U.S. PATENT DOCUMENTS

| | | |
|---|---|---|
| 4,466,426 A | 8/1984 | Blackman |
| 4,636,217 A | 1/1987 | Ogilvie et al. |
| | (Continued) | |

FOREIGN PATENT DOCUMENTS

| | | |
|---|---|---|
| WO | WO 2006/102485 | 9/2006 |
| WO | WO 2006/105437 A2 | 10/2006 |
| | (Continued) | |

OTHER PUBLICATIONS

Bacfuse® Spinous Process Fusion Plate Surgical Technique, 2011, Pioneer Surgical, 12 pages.
(Continued)

*Primary Examiner* — Larry E Waggle, Jr.
(74) *Attorney, Agent, or Firm* — Foley & Lardner LLP

(57) ABSTRACT

A device for insertion into a spinal (intervertebral or intravertebral) space is expandable and contractable. The device includes a body assembly, a top member configured to fit within a gap in the body assembly, a drive gear disposed within the body assembly at a distal end of the body assembly, a proximal gear assembly, and a distal gear assembly. The drive gear includes a receiver accessible from outside the body assembly and configured to be rotated in order to rotate the drive gear. Each gear assembly is attached to the top member. The distal gear assembly engages the drive gear. Rotation of the drive gear in a first direction causes the gear assemblies to translate the top member away from the body assembly, and rotation of the drive gear in a second direction causes the gear assemblies to translate the top member towards the body assembly.

18 Claims, 66 Drawing Sheets

Related U.S. Application Data continuation-in-part of application No. 13/802,110, filed on Mar. 13, 2013, now Pat. No. 9,034,041, which is a continuation-in-part of application No. 13/615,273, filed on Sep. 13, 2012, now Pat. No. 8,940,048, which is a continuation-in-part of application No. 12/789,257, filed on May 27, 2010, now Pat. No. 8,512,407, which is a division of application No. 11/394,719, filed on Mar. 31, 2006, now Pat. No. 7,731,751.

(60) Provisional application No. 60/666,945, filed on Mar. 31, 2005.

(52) U.S. Cl.
CPC .............. *A61F 2/442* (2013.01); *A61F 2/446* (2013.01); *A61F 2/447* (2013.01); *A61F 2/4455* (2013.01); *A61F 2002/3037* (2013.01); *A61F 2002/3055* (2013.01); *A61F 2002/30158* (2013.01); *A61F 2002/30163* (2013.01); *A61F 2002/30179* (2013.01); *A61F 2002/30428* (2013.01); *A61F 2002/30471* (2013.01); *A61F 2002/30482* (2013.01); *A61F 2002/30507* (2013.01); *A61F 2002/30523* (2013.01); *A61F 2002/30537* (2013.01); *A61F 2002/30556* (2013.01); *A61F 2002/30579* (2013.01); *A61F 2002/30594* (2013.01); *A61F 2002/30784* (2013.01); *A61F 2002/30841* (2013.01); *A61F 2002/30904* (2013.01); *A61F 2002/4415* (2013.01); *A61F 2310/00017* (2013.01); *A61F 2310/00023* (2013.01)

(56) References Cited

U.S. PATENT DOCUMENTS

| | | | |
|---|---|---|---|
| 4,863,476 A | 9/1989 | Shepperd | |
| 5,390,683 A | 2/1995 | Pisharodi | |
| 5,645,599 A | 7/1997 | Samani | |
| 5,658,335 A | 8/1997 | Allen | |
| 5,658,337 A | 8/1997 | Kohrs et al. | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,126,689 A | 10/2000 | Brett | |
| 6,176,882 B1 | 1/2001 | Biedermann et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,375,682 B1 | 4/2002 | Fleischmann et al. | |
| 6,409,766 B1 | 6/2002 | Brett | |
| 6,451,019 B1 | 9/2002 | Zucherman et al. | |
| 6,491,724 B1 | 12/2002 | Ferree | |
| 6,494,883 B1 | 12/2002 | Ferree | |
| 6,537,320 B1 | 3/2003 | Michelson | |
| 6,648,917 B2 | 11/2003 | Gerbec et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,773,460 B2 | 8/2004 | Jackson | |
| 6,796,983 B1 | 9/2004 | Zucherman et al. | |
| 7,048,736 B2 | 5/2006 | Robinson et al. | |
| 7,087,055 B2 | 8/2006 | Lim et al. | |
| 7,101,375 B2 | 9/2006 | Zucherman et al. | |
| 7,217,291 B2 | 5/2007 | Zucherman et al. | |
| 7,621,950 B1 | 11/2009 | Globerman et al. | |
| 7,695,513 B2 | 4/2010 | Zucherman et al. | |
| 7,731,751 B2 | 6/2010 | Butler et al. | |
| 7,879,098 B1 | 2/2011 | Simmons, Jr. | |
| 8,016,861 B2* | 9/2011 | Mitchell | A61B 17/7005 606/264 |
| 8,048,117 B2 | 11/2011 | Zucherman et al. | |
| 8,105,382 B2 | 1/2012 | Olmos et al. | |
| 8,231,656 B2 | 7/2012 | Lee et al. | |
| 8,241,330 B2 | 8/2012 | Lamborne et al. | |
| 8,303,663 B2* | 11/2012 | Jimenez | A61F 2/4465 623/17.16 |
| 8,343,190 B1 | 1/2013 | Mueller et al. | |
| 8,353,963 B2* | 1/2013 | Glerum | A61F 2/442 623/17.16 |
| 8,382,801 B2 | 2/2013 | Lamborne et al. | |
| 8,597,360 B2 | 12/2013 | McLuen et al. | |
| 8,894,711 B2 | 11/2014 | Varela | |
| 8,894,712 B2 | 11/2014 | Varela | |
| 9,034,041 B2 | 5/2015 | Wolters et al. | |
| 9,532,883 B2* | 1/2017 | McLuen | A61F 2/447 |
| 2002/0128716 A1 | 9/2002 | Cohen et al. | |
| 2003/0040746 A1 | 2/2003 | Mitchell et al. | |
| 2003/0236520 A1 | 12/2003 | Lim et al. | |
| 2004/0153156 A1 | 8/2004 | Cohen et al. | |
| 2004/0167625 A1 | 8/2004 | Beyar et al. | |
| 2005/0033437 A1 | 2/2005 | Bao et al. | |
| 2005/0070911 A1 | 3/2005 | Carrison et al. | |
| 2005/0131536 A1 | 6/2005 | Eisermann et al. | |
| 2005/0143827 A1 | 6/2005 | Globerman et al. | |
| 2005/0222681 A1 | 10/2005 | Richley et al. | |
| 2005/0228391 A1 | 10/2005 | Levy et al. | |
| 2005/0261769 A1 | 11/2005 | Moskowitz et al. | |
| 2005/0278036 A1 | 12/2005 | Leonard et al. | |
| 2006/0036258 A1 | 2/2006 | Zucherman et al. | |
| 2006/0084988 A1 | 4/2006 | Kim | |
| 2006/0089718 A1 | 4/2006 | Zucherman et al. | |
| 2006/0095136 A1 | 5/2006 | McLuen | |
| 2006/0189999 A1 | 8/2006 | Zwirkoski | |
| 2006/0241601 A1 | 10/2006 | Trautwein et al. | |
| 2006/0264938 A1 | 11/2006 | Zucherman et al. | |
| 2007/0142915 A1 | 6/2007 | Altarac et al. | |
| 2008/0114456 A1 | 5/2008 | Dewey et al. | |
| 2008/0140207 A1 | 6/2008 | Olmos et al. | |
| 2008/0161818 A1 | 7/2008 | Kloss et al. | |
| 2008/0177391 A1 | 7/2008 | Mitchell et al. | |
| 2008/0183211 A1 | 7/2008 | Lamborne et al. | |
| 2008/0312741 A1 | 12/2008 | Lee et al. | |
| 2009/0062915 A1 | 3/2009 | Kohm et al. | |
| 2010/0179655 A1 | 7/2010 | Hansell et al. | |
| 2010/0211176 A1 | 8/2010 | Greenhalgh | |
| 2010/0241167 A1 | 9/2010 | Taber et al. | |
| 2011/0022090 A1 | 1/2011 | Gordon et al. | |
| 2011/0066186 A1 | 3/2011 | Boyer et al. | |
| 2011/0144692 A1 | 6/2011 | Saladin et al. | |
| 2011/0172709 A1 | 7/2011 | Lyons et al. | |
| 2011/0184468 A1 | 7/2011 | Metcalf et al. | |
| 2011/0224731 A1 | 9/2011 | Smisson et al. | |
| 2011/0282453 A1 | 11/2011 | Greenhalgh et al. | |
| 2011/0319997 A1 | 12/2011 | Glerum et al. | |
| 2012/0016418 A1 | 1/2012 | Chin et al. | |
| 2012/0059474 A1 | 3/2012 | Weiman | |
| 2012/0109203 A1 | 5/2012 | Dryer et al. | |
| 2012/0221051 A1 | 8/2012 | Robinson | |
| 2012/0330422 A1 | 12/2012 | Weiman | |
| 2013/0085572 A1 | 4/2013 | Glerum et al. | |
| 2013/0103156 A1 | 4/2013 | Packer et al. | |
| 2013/0158664 A1 | 6/2013 | Palmatier et al. | |
| 2013/0158668 A1* | 6/2013 | Nichols | A61F 2/4455 623/17.16 |
| 2013/0158669 A1 | 6/2013 | Sungarian et al. | |
| 2013/0211526 A1 | 8/2013 | Alheidt et al. | |
| 2014/0148904 A1 | 5/2014 | Robinson | |
| 2014/0236296 A1 | 8/2014 | Wagner et al. | |
| 2014/0277473 A1 | 9/2014 | Perrow | |
| 2014/0277500 A1 | 9/2014 | Logan et al. | |
| 2015/0100128 A1 | 4/2015 | Glerum et al. | |
| 2015/0173917 A1 | 6/2015 | Radcliffe et al. | |
| 2016/0242927 A1 | 8/2016 | Seifert et al. | |
| 2017/0056197 A1 | 3/2017 | Weiman et al. | |

(56) References Cited

U.S. PATENT DOCUMENTS

FOREIGN PATENT DOCUMENTS

| WO | WO 2009/124269 | 10/2009 |
| WO | WO 2016/077610 A1 | 5/2016 |
| WO | WO 2016/127139 A1 | 8/2016 |
| WO | WO 2017/027873 A1 | 2/2017 |
| WO | WO 2017/066463 A1 | 4/2017 |

OTHER PUBLICATIONS

Extended European Search Report for European Application No. 14159101.6, dated Jun. 18, 2014, 6 pages.
Extended European Search Report for European Application No. 16169890.7, dated Oct. 21, 2016, 7 pages.
International Preliminary Report on Patentability for Application No. PCT/US06/12060, dated Jul. 18, 2007, 3 pages.
International Search Report and Written Opinion for International Application No. PCT/US2012/057324, dated Dec. 20, 2012, 10 pages.
International Search Report for Application No. PCT/US06/12060, dated Apr. 5, 2007, 1 page.
Written Opinion of the International Searching Authority for Application No. PCT/US06/12060, dated Apr. 5, 2007, 3 pages.
Search Report for International Application No. PCT/US2018/029120, dated Jun. 28, 2018, 17 pages.
Search Report for International Application No. PCT/US2018/029149, dated Jun. 25, 2018, 13 pages.
Search Report for International Application No. PCT/US2018/041306, dated Sep. 28, 2018, 12 pages.

\* cited by examiner

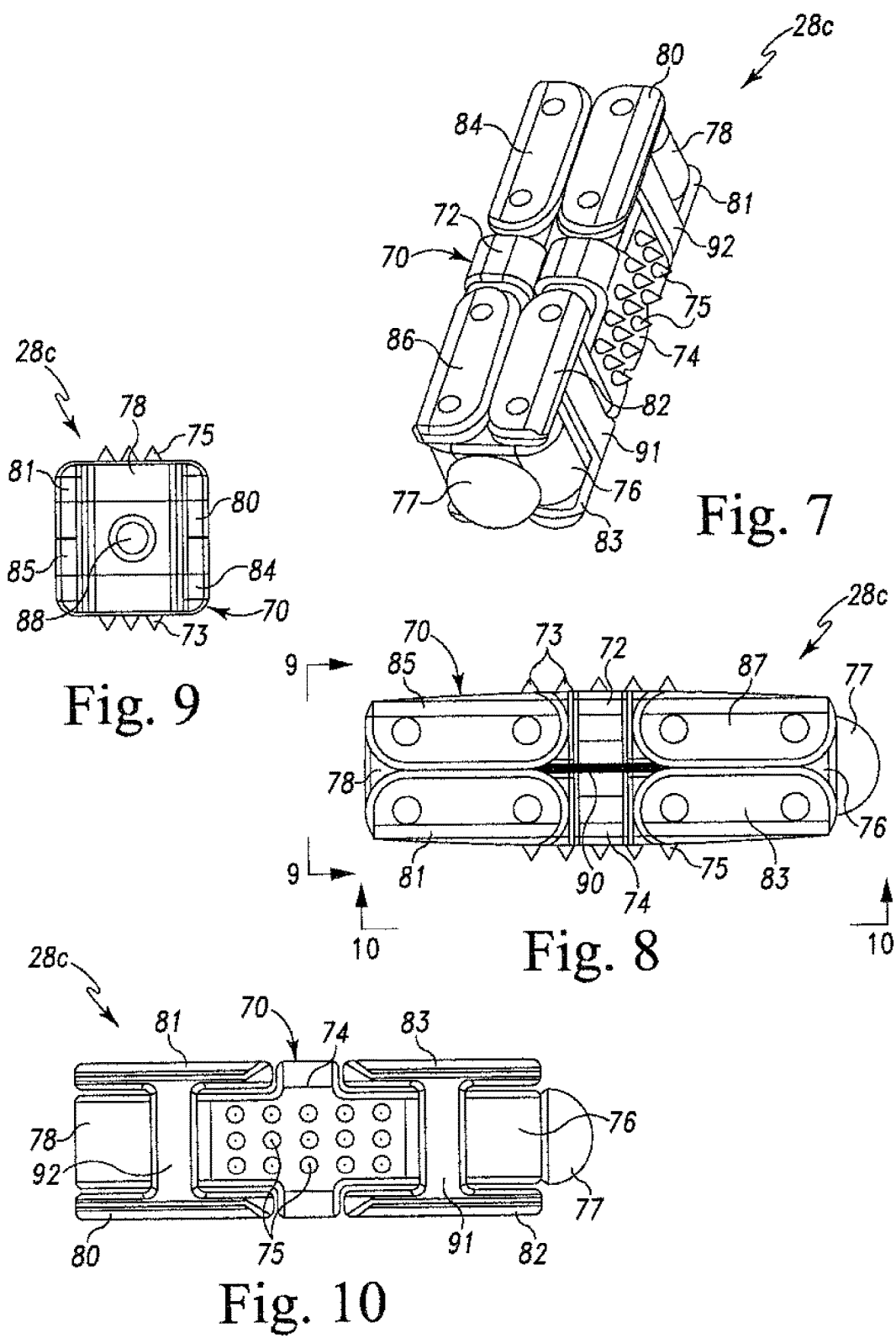

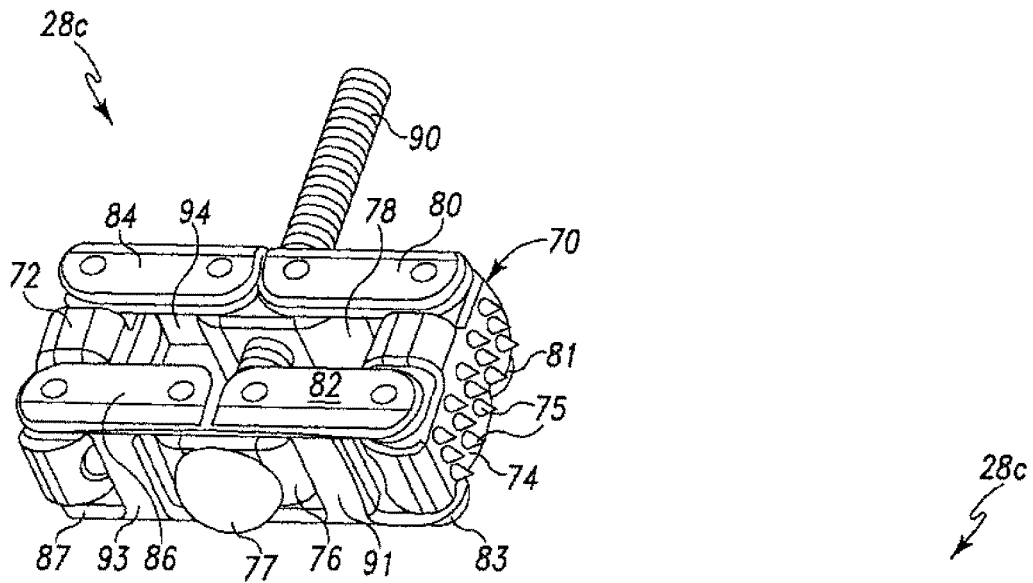
Fig. 11
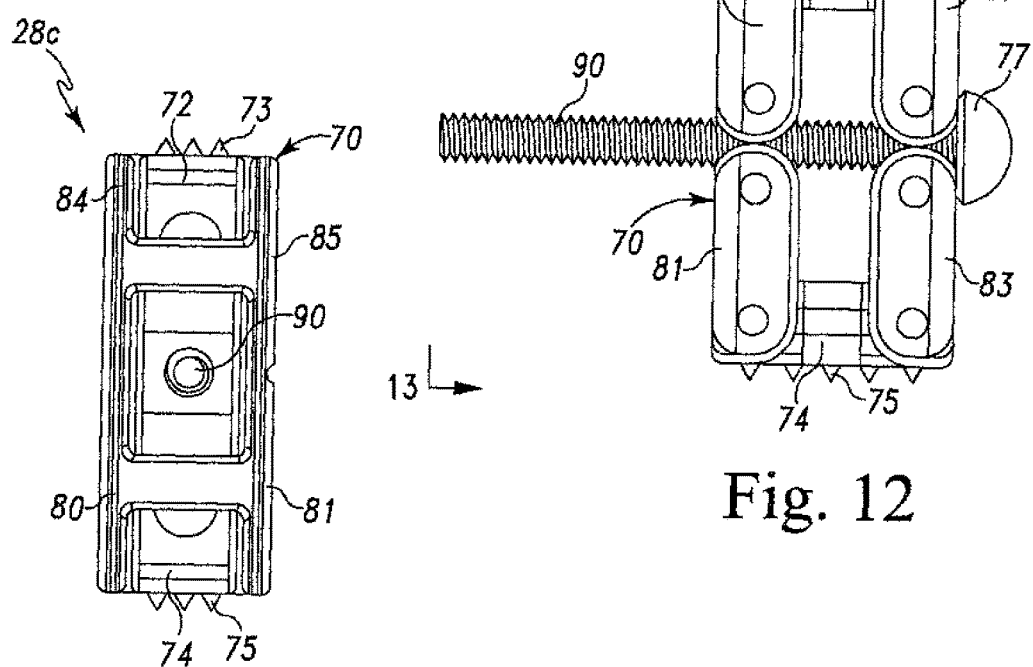
Fig. 13
Fig. 12

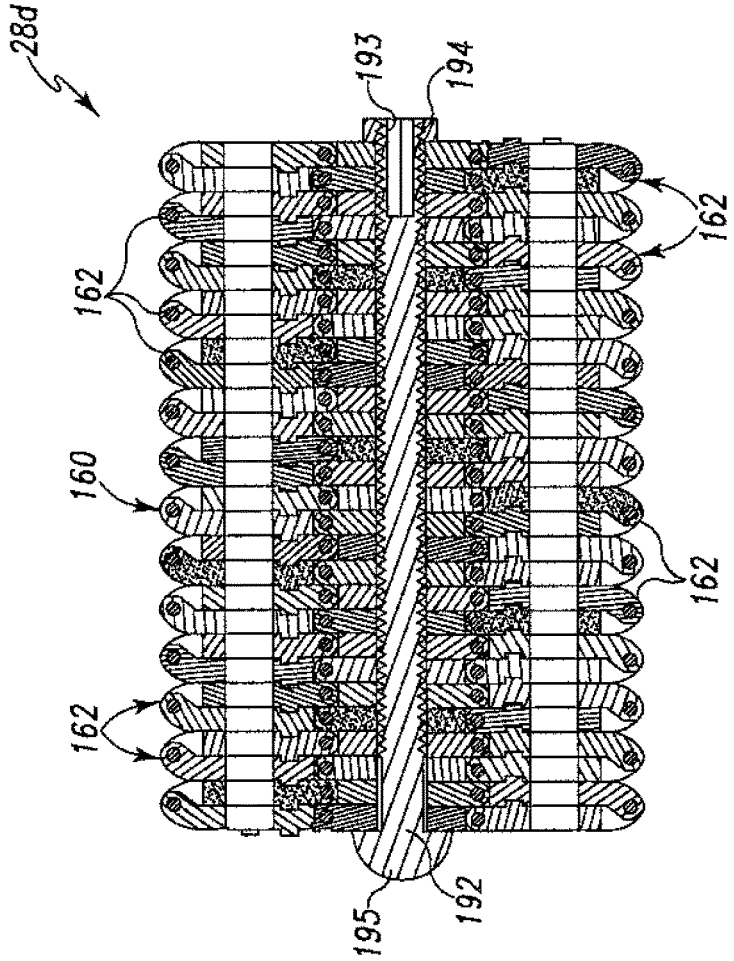
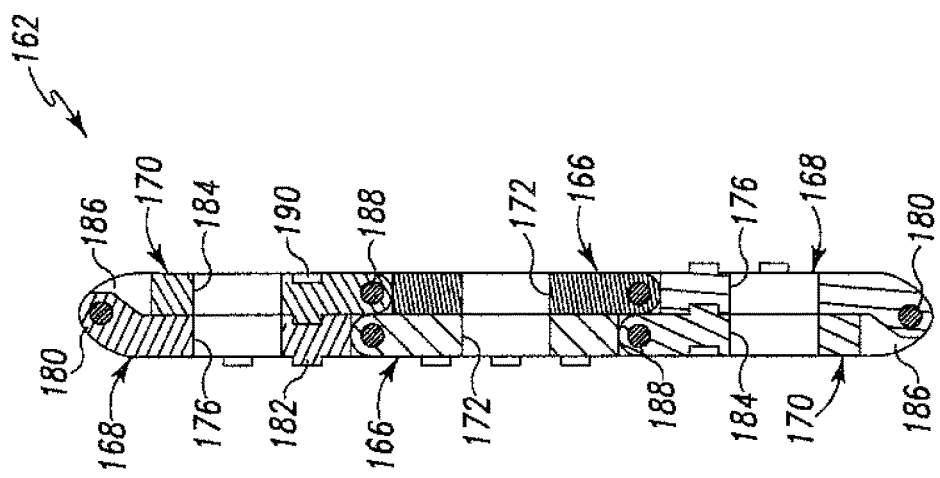
Fig. 16
Fig. 17

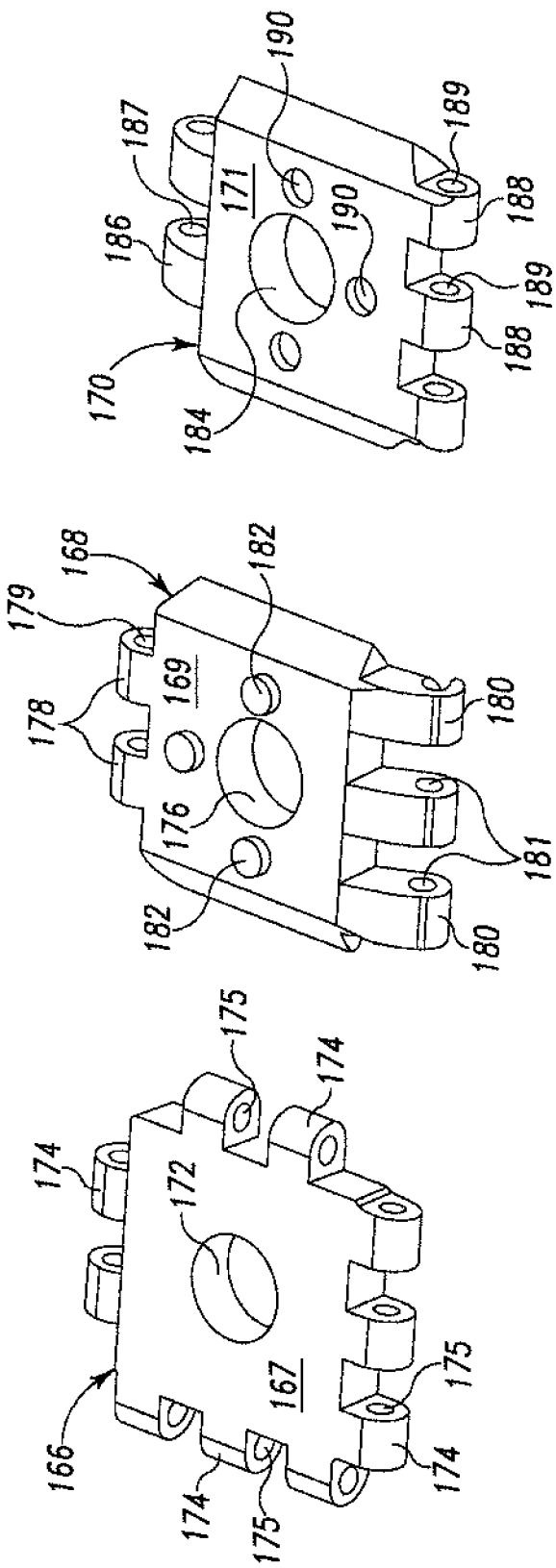

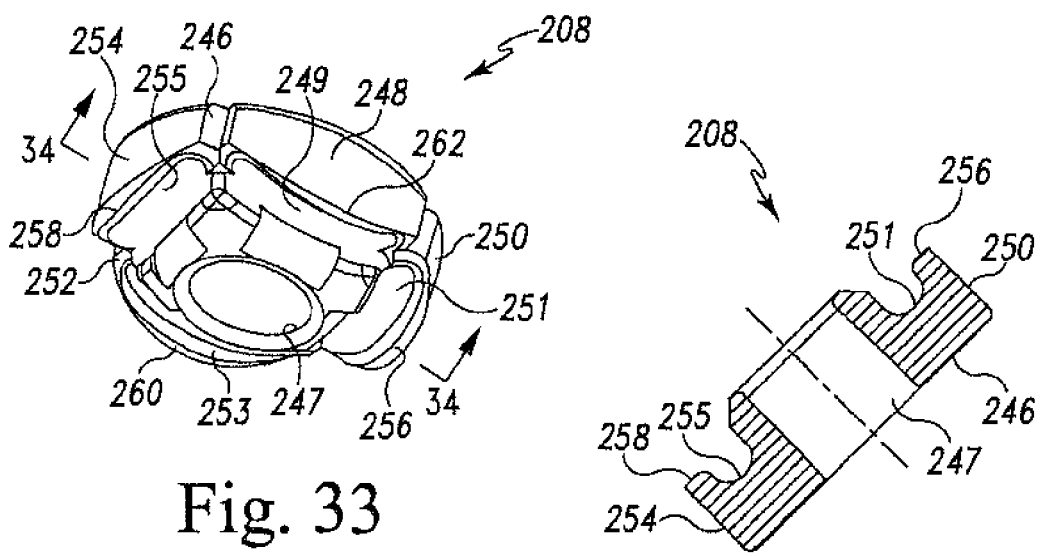
Fig. 33
Fig. 34
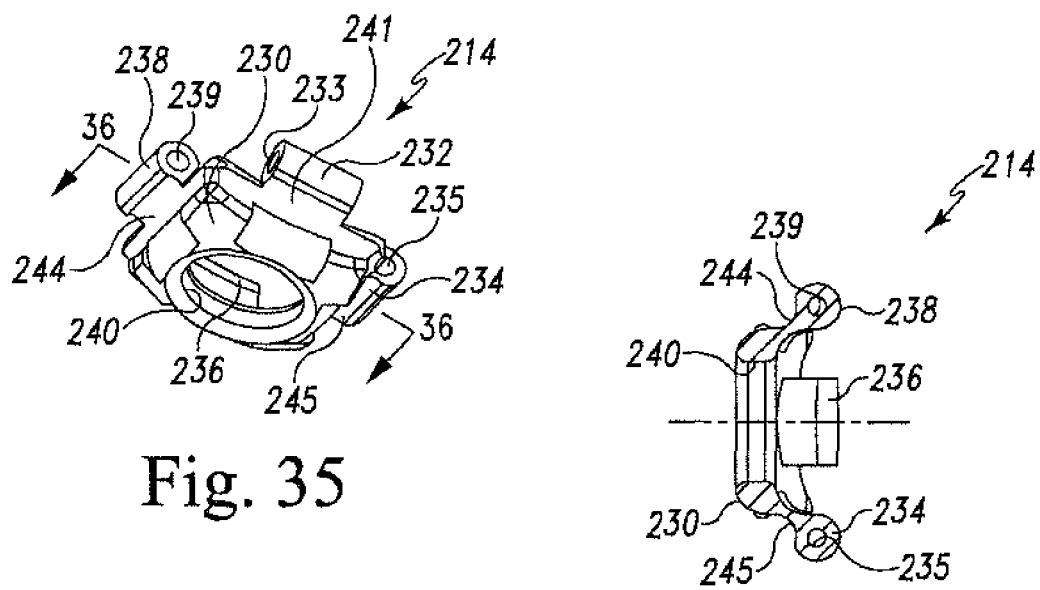
Fig. 35
Fig. 36

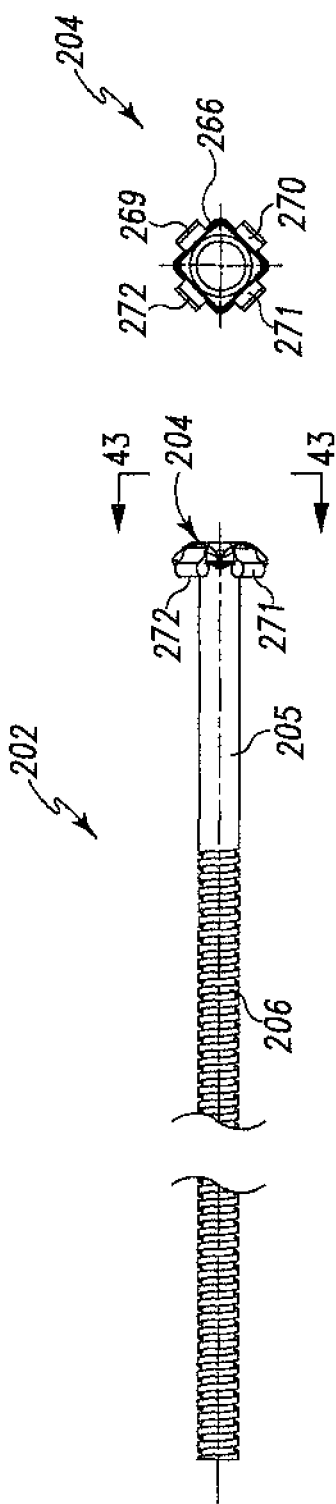
Fig. 42
Fig. 43
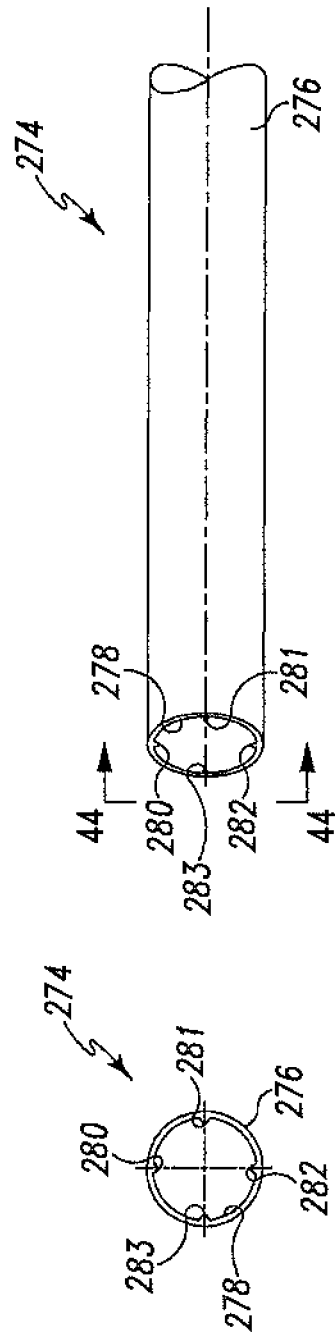
Fig. 44
Fig. 45

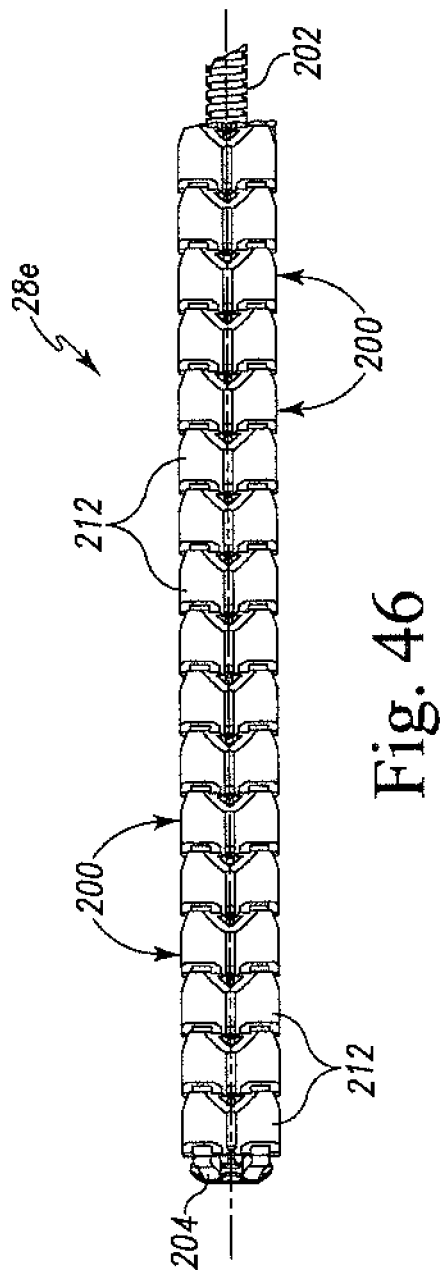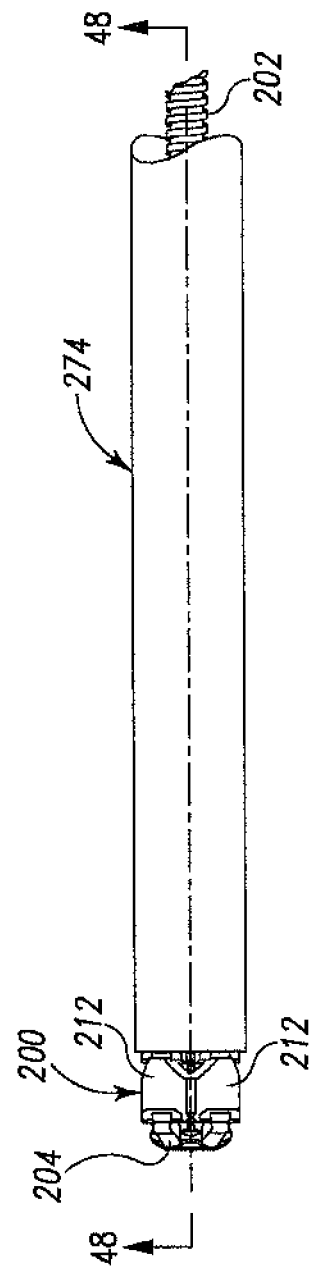

EXPANDABLE INTERBODY AND INTRAVERTEBRAL BODY DEVICES

CROSS-REFERENCE TO RELATED PATENT APPLICATIONS

This application is a continuation of U.S. application Ser. No. 14/714,821, filed May 18, 2015, which is a continuation-in-part of U.S. application Ser. No. 13/802,110, filed Mar. 13, 2013, which is a continuation-in-part of U.S. application Ser. No. 13/615,273, filed Sep. 13, 2012, which is a continuation-in-part of U.S. application Ser. No. 12/789,257, filed May 27, 2010, which is a divisional of U.S. application Ser. No. 11/394,719, filed Mar. 31, 2006, which claims the benefit of U.S. Provisional Application No. 60/666,945, filed Mar. 31, 2005. All of these applications are incorporated herein by reference in their entireties.

BACKGROUND

The present invention relates to spinal interbody and intravertebral body devices and, more particularly, to vertebral interbody and intravertebral devices that are expandable after spinal placement thereof.

Fusion cages, as well as other types of bodies and/or devices, are frequently utilized in spinal surgery inside a vertebra (intravertebral) and/or between vertebrae of a patient (interbody). With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size. This poses various problems with their use and/or implantation. Particularly, static sized spinal devices are fairly large in order to properly bridge the gap between adjacent vertebrae. This large size does not lend itself to microsurgery, arthroscopic surgery or the like.

A few interbody devices, however, are now being made that are expandable. Expandable interbody devices allow the interbody device to be initially smaller than traditional non-expandable (static) interbody devices such that expandable interbody devices may be more easily inserted or implanted into the vertebral space. Moreover, expandable interbody devices allow the surgeon to set the amount of expansion necessary for the particular patient rather than the static interbody device dictating the spacing.

However, current expandable spinal devices lack strength, reliability and/or simplicity of design.

In view of the above, it is desirable to provide expandable spinal devices that address prior art concerns.

In view of the above, it is desirable to provide expandable spinal interbody devices that address prior art concerns.

In view of the above, it is desirable to provide expandable spinal intravertebral body devices that address prior art concerns.

SUMMARY

The present invention provides expandable spinal interbody and intravertebral body devices for insertion and maintenance between adjacent vertebrae and inside a vertebra of the spine. Particularly, the present invention provides various embodiments of expandable and/or dynamic vertebral interbody and intravertebral body devices that expand from a first radial profile into a second radial profile.

One or more of the present various expandable interbody and intravertebral devices may also provide a dynamization, mobilization or artificial disk platform. One or more of the various dynamic expandable interbody/intravertebral body devices as an artificial disk platform thus allows micro motion of the spine to occur. Additionally, one or more of the present various dynamic expandable interbody/intravertebral devices may function as a fusion device when bone, therapeutic agent or the like is included therein.

In one form, an expandable vertebral interbody/intravertebral body device for insertion into a vertebral space is provided. The interbody/intravertebral body device is expandable from a first circumference (radial profile) to a second circumference (radial profile) through axial compression of segments of the vertebral interbody/intravertebral body device, particularly once the interbody/intravertebral body device has been properly situated within a vertebral space. The interbody/intravertebral body device is characterized by a plurality of axially stacked, individual segments that are provided on a central insertion and deployment rod. Each segment includes a central plate or body to which are pivotally attached plate or leaf structures. Pivoting of the structures provides a collapsed or unexpanded position of the first circumference and an open or expanded position of the second circumference. The vertebral interbody/intravertebral body device may be formed of a biocompatible radiolucent material. The radial profile of an interbody/intravertebral body device is easily defined by plate or leaf structures of the segments.

In some embodiments, an implant for insertion into a spinal space comprises a body assembly, the body assembly comprising a first portion moveably coupled to a second portion along a longitudinal axis; and upper and lower support members disposed at least partially between the first portion and the second portion; wherein movement of the first portion and the second portion toward each other causes the upper and lower support members to move away from each other, and wherein movement of the first portion and the second portion away from each other causes the upper and lower members to move toward each other.

In further embodiments, an implant comprises a front portion; a rear portion; a control portion extending through the rear portion and at least partially within an the second portion; and first and second support members configured to move away from each other in a linear fashion as the control portion moves into the front portion.

In yet further embodiments, an implant for insertion into a spinal space comprises a front member having at least one first projection and at least one first ramped surface; a rear member having at least one second projection and at least one second ramped surface; and at least one support having a first channel slidingly receiving the at least one first projection and a second channel slidingly receiving the at least one second channel; wherein relative movement between the front and rear members causes the at least one first projection to slide within the first channel and the at least one second projection to slide within the second channel to change a height of implant.

BRIEF DESCRIPTION OF THE DRAWINGS

The foregoing and other features of the present invention will become more apparent to one skilled in the art upon also reading the following description of embodiments with reference to the accompanying drawings wherein:

FIG. 7 is a perspective view of an exemplary embodiment of an expandable interbody/intravertebral body device in accordance with the present principles, the interbody/intravertebral body device shown in a pre-implant or unexpanded state;

FIG. 8 is a side view of the expandable interbody/intravertebral body device of FIG. 7;

FIG. 9 is a left side view of the expandable interbody/intravertebral body device of FIG. 8 taken along line 9-9 thereof;

FIG. 10 is a bottom view of the expandable interbody/intravertebral body device of FIG. 8 taken along line 10-10 thereof;

FIG. 11 is a perspective view of the expandable interbody/intravertebral body device of FIG. 7 shown in a post-implant or expanded state;

FIG. 12 is a side view of the expandable interbody/intravertebral body device of FIG. 11;

FIG. 13 is a right side view of the expandable interbody/intravertebral body device of FIG. 12 taken along line 13-13 thereof;

FIG. 16 is a sectional view of the expandable interbody/intravertebral body device of FIG. 15 taken along line 16-16 thereof;

FIG. 17 is an enlarged sectional view of a single segment, section or petal of the expandable interbody/intravertebral body device of FIG. 16, the single segment shown in an expanded position;

FIG. 20 is an enlarged perspective view of an end plate of the expandable interbody/intravertebral body segment of FIG. 18;

FIG. 21 is an enlarged perspective view of a first interconnect plate of the expandable interbody/intravertebral body segment of FIG. 18;

FIG. 22 is an enlarged perspective view of a second inter-connect plate of the expandable interbody/intravertebral body segment of FIG. 18;

FIG. 33 is a perspective view of an end plate of the expandable interbody/intravertebral body device of FIG. 23;

FIG. 34 is a sectional view of the end plate of FIG. 33 taken along line 34-34 thereof;

FIG. 35 is a perspective view of a deploy plate of the interbody/intravertebral body segment of the expandable interbody/intravertebral body device of FIG. 23;

FIG. 36 is a sectional view of the deploy plate of FIG. 35 taken along line 36-36 thereof;

FIG. 42 is a side view of an implant and deploy rod for use with the expandable interbody/intravertebral body device of FIG. 23;

FIG. 43 is a right side (end) view of the rod of FIG. 42 taken along line 43-43 thereof;

FIG. 44 is an end view of an exemplary insertion and deployment cannula for the various expandable interbody/intravertebral body devices taken along line 44-44 of FIG. 45;

FIG. 45 is a side view of the exemplary insertion and deployment cannula of FIG. 44;

FIG. 46 is a side view of the expandable interbody/intravertebral body device of FIG. 23 in a folded position;

FIG. 47 is a side view of the insertion and deployment cannula of FIG. 45 holding the folded interbody/intravertebral body device of FIG. 46;

FIG. 120 is an exploded perspective view of the expandable implant of FIG. 119 according to an exemplary embodiment.

FIG. 121 is an exploded perspective view of the expandable implant of FIG. 119 according to another exemplary embodiment.

FIG. 122 is an exploded perspective view of an expandable implant according to another exemplary embodiment.

FIG. 123 is an exploded perspective view of the expandable implant of FIG. 122 according to another exemplary embodiment.

Figure 1:
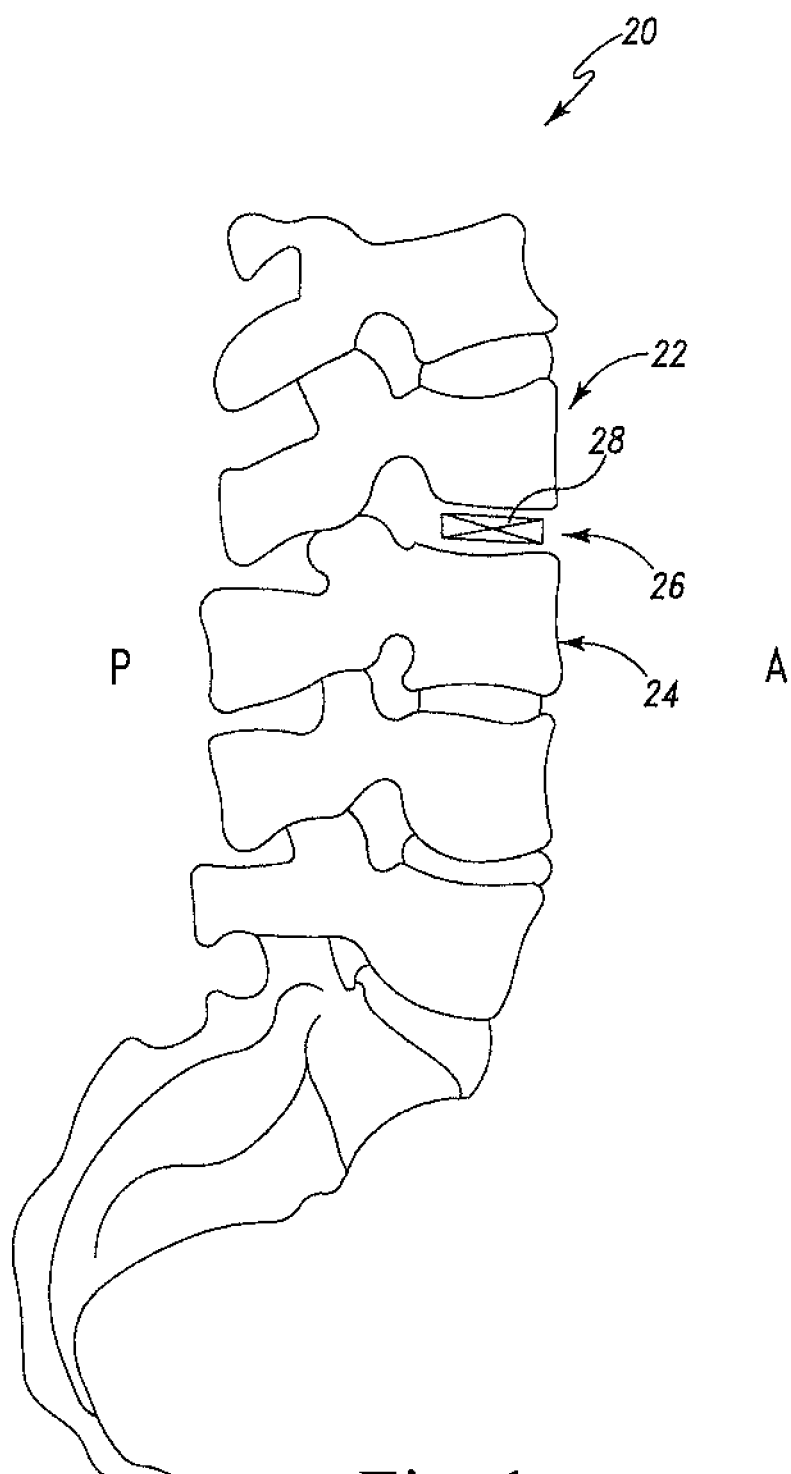
FIG. 1 is a side view of a portion of a human spine illustrating inter-vertebral placement of an expandable interbody/intravertebral body device in accordance with the principles of the present invention.

Corresponding reference characters indicate corresponding parts throughout the several views. Although the drawings represent embodiments of the invention, the drawings are not necessarily to scale and certain features may be exaggerated in order to better illustrate and explain the principles of the present invention. The exemplifications set out herein illustrate several embodiments of the invention, but the exemplifications are not to be construed as limiting the scope of the invention in any manner.

DETAILED DESCRIPTION OF EXEMPLARY EMBODIMENTS

The present invention relates to expandable and/or dynamic interbody (between adjacent vertebrae), intravertebral body devices (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization and/or promoting bone growth between or inside vertebrae that have been destabilized or otherwise due to injury, illness and/or the like. Particularly, the present invention provides various versions of dynamic (expandable and/or expandable and retractable) interbody/intravertebral body devices that are usable in a spinal column of a human. As representative of each one of the various versions of the present invention, FIG. 1 illustrates a representative dynamic spinal body device 28. The spinal body 28 is depicted as implanted or inserted into a human spine of which only a lower portion 20 of the spine is shown. The spinal device 28 is illustrated implanted between adjacent upper and lower vertebrae 22, 24 of the spine portion 20 in FIG. 1 (hence interbody or intervertebral). A spinal device 28 illustrated as body 28f is shown as implanted into a vertebra (hence intravertebral body) in FIGS. 57 and 58. Vertebrae 22 and 24 have portions that face anteriorly ("A", and from the right as viewed in FIG. 1) and portions that face posteriorly ("P", and from the left as viewed in FIG. 1).

Figure 2:
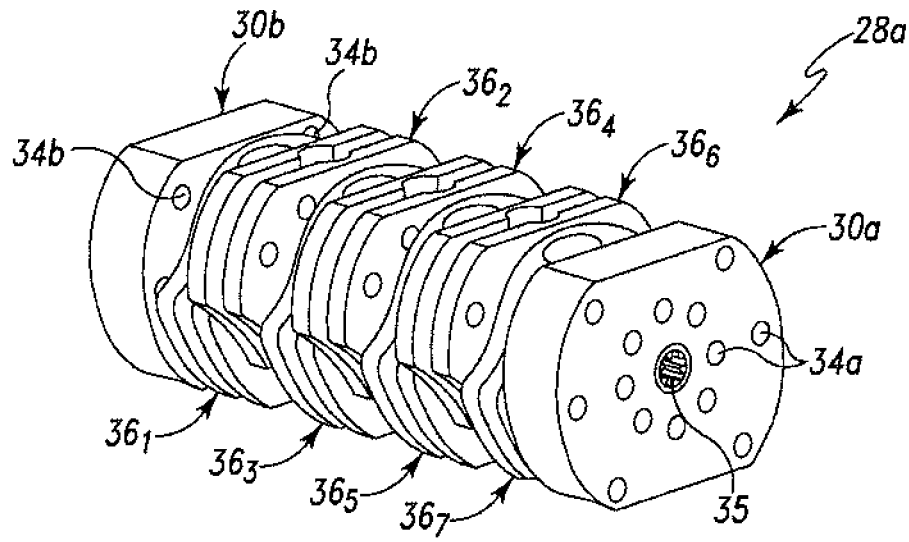
FIG. 2 is a perspective view of an exemplary embodiment of an expandable interbody/intravertebral body device in accordance with the present principles, the expandable interbody/intravertebral body device depicted in a pre-implant or unexpanded state.
Figure 3:
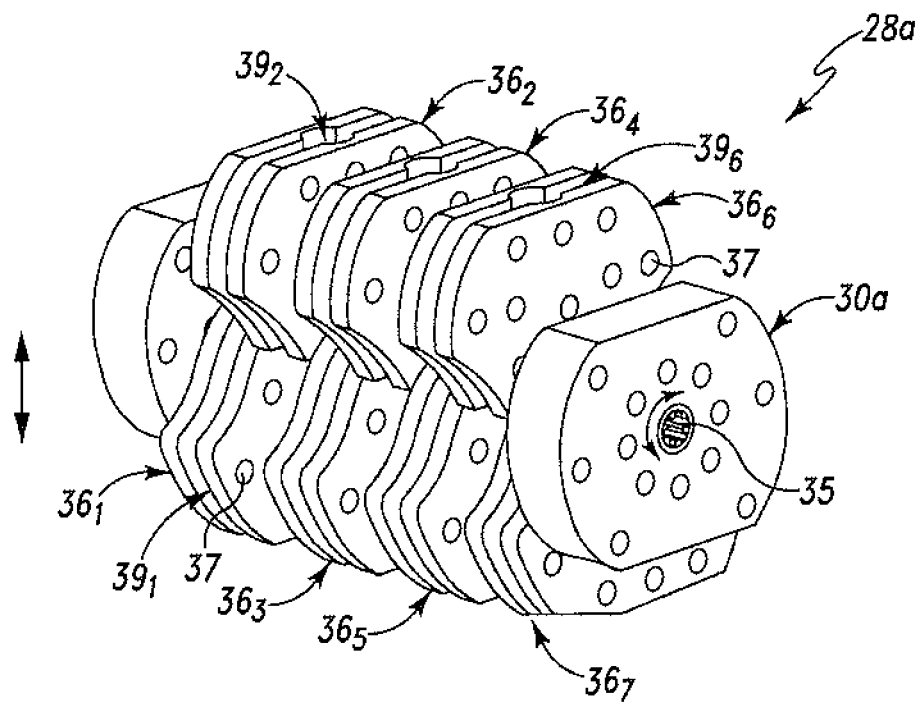
FIG. 3 is a perspective view of the expandable interbody/intravertebral body device of FIG. 2 depicted in a post-implant or expanded state.

Referring to FIGS. 2 and 3, there is depicted an embodiment of an expandable and retractable interbody/intravertebral body device generally designated 28a. FIG. 2 depicts the interbody/intravertebral body device 28a in a fully unexpanded or fully retracted position, while FIG. 3 depicts the interbody/intravertebral body device 28*a* in a fully expanded or fully un-retracted position. Of course, the interbody/intravertebral body device 28*a* may be positioned anywhere between the fully expanded to fully retracted positions.

The interbody/intravertebral body device 28*a* is a posterior (can be inserted in any direction) inserted interbody/intravertebral body device that provides controlled, vertical expansion within the intervertebral space 26 as well as vertical retraction within the intervertebral space 26. The interbody/intravertebral body device 28*a* includes identical end plates 30*a*, 30*b* each having holes or bores 34*a*, 34*b* therethrough. A central axis or shaft 35 has ends retained in each end plate 30*a*, 30*b* for rotation of the shaft 35. The ends of the shaft 35 are configured to receive a tool for rotation of the shaft and the expansion or retraction of a plurality of plates $36_1$, $36_2$, $36_3$, $36_4$, $36_5$, $36_6$, and $36_7$.

Each one of the plurality of plates 36 includes holes or bores 37. Additionally, each plate 36 is partially bifurcated creating a slot 39 in each plate. The plates 36 are connected to the shaft 35 such that one set of plates $36_1$, $36_3$, $36_5$, and $36_7$ move in one outward direction (expansion) upon shaft rotation in a first direction while another set of plates $36_2$, $36_4$, and $36_6$ move in another (opposite) outward direction (expansion) upon shaft rotation in the first direction. Shaft rotation in a second direction causes both sets of plates to retract. The adjustment of the expansion/retraction of the plates $36_1$, $36_2$, $36_3$, $36_4$, $36_5$, $36_6$, and $36_7$ is done in situ. The interbody/intravertebral body device 28*a* may also act as an artificial disk allowing movement.

Figure 4:
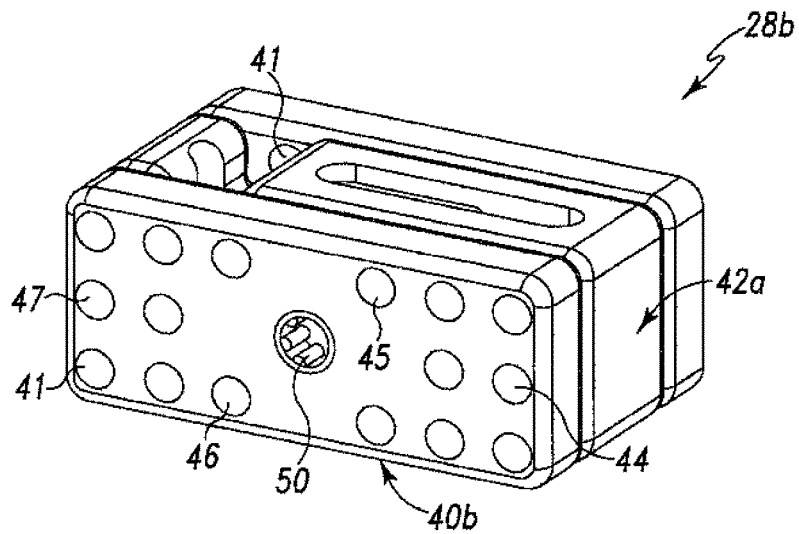
FIG. 4 is a perspective view of an exemplary embodiment of an expandable interbody/intravertebral body device in accordance with the present principles, the expandable interbody/intravertebral body device depicted in a pre-implant or unexpanded state.
Figure 5:
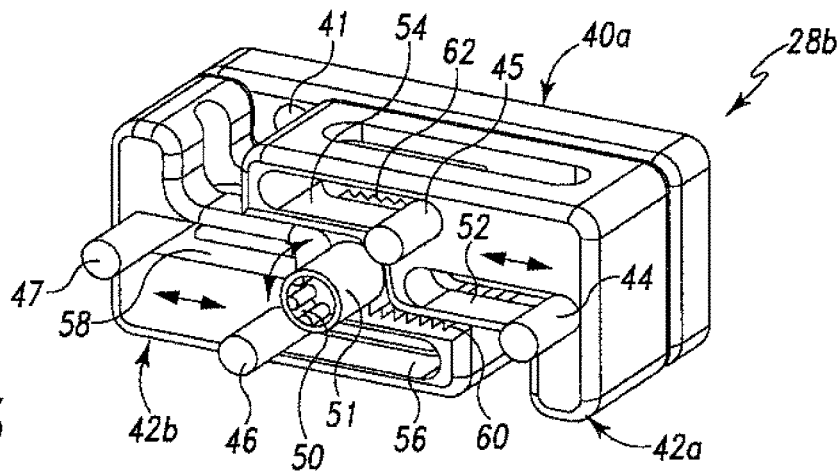
FIG. 5 is a perspective view of the expandable interbody/intravertebral body device of FIG. 4 depicted in the pre-implant or unexpanded state with a plate thereof removed for viewing of an expansion mechanism thereof.
Figure 6:
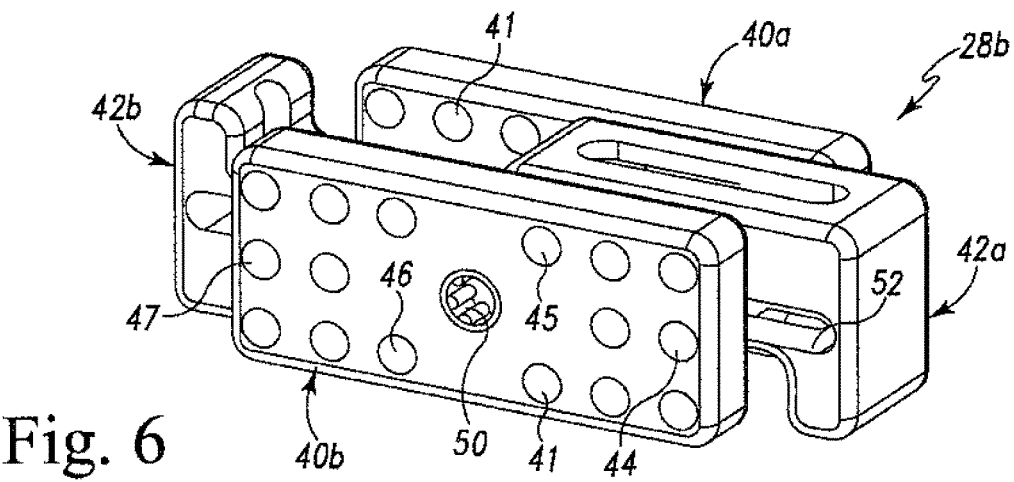
FIG. 6 is a perspective view of the expandable interbody/intravertebral body device of FIG. 4 depicted in a post-implant or expanded state.

Referring to FIGS. 4-6 there is depicted an embodiment of an expandable and retractable (dynamic) interbody/intravertebral body device generally designated 28*b*. FIG. 4 depicts the interbody/intravertebral body device 28*b* in a fully unexpanded or fully retracted position, while FIG. 6 depicts the interbody/intravertebral body device 28*b* in a fully expanded or fully un-retracted position. Of course, the interbody/intravertebral body device 28*b* may be positioned anywhere between the fully expanded to fully retracted positions. FIG. 5 depicts the manner in which the interbody/intravertebral body device 28*b* expands. Thus, in FIG. 5 the end plate 40*b* is removed for clarity in illustrating such expansion (and oppositely, contraction).

The interbody/intravertebral body device 28*b* is an anterior inserted interbody/intravertebral body device that provides controlled, horizontal expansion within the intervertebral space 26 as well as vertical retraction within the intervertebral space 26. The interbody/intravertebral body device 28*b* includes identical end plates 40*a*, 40*b* each having holes or bores 41 therein. The end plates 40*a*, 40*b* are joined together via posts 44, 45, 46 and 47. The posts 44, 45, 46 and 47 also provide a guide for the identical expansion/retraction members 42*a* and 42*b* that are retained between the end plates 40*a*, 40*b*.

Particularly, member 42*a* has a first slot 52 in which post 44 is situated, and a second slot 54 in which post 45 is situated. The slots and posts define the length of travel for the member 42*a* when the keyed shaft 50 is rotated. As well, the member 42*b* has a first slot 56 in which post 46 is situated, and a second slot 58 in which post 47 is situated. The slots and posts define the length of travel for the member 42*b* when the keyed shaft 50 is rotated.

The shaft 50 includes knurls or teeth 51 on an outside thereof that co-act with teeth 60 of member 42*a* and teeth 62 of the member 42*b*. Rotation of the shaft 50 in a first radial direction moves the members 42*a* and 42*b* in opposite and outward direction. Rotation of the shaft 50 in a second direction (opposite the first direction) moves the members 42*a* and 42*b* inwardly.

Referring to FIGS. 7-13 there is depicted another embodiment of an interbody/intravertebral body device generally designated 28*c*. The interbody/intravertebral body device 28*c* is shown in a pre-implant or unexpanded/collapsed state in FIGS. 7-10 and in a post-implant or expanded state in FIGS. 11-13. The interbody/intravertebral body device 28*c* is characterized by a body 70 having a first end plate 72 and a second end plate 75. The first end plate 72 includes a plurality of grips or spikes 73. The second end plate 74 also includes a plurality of grips or spikes 74. The spikes 73, 75 are shown as cone-shaped but may take on other forms. The spikes 73, 75 are designed to grip or extend into adjacent vertebrae.

The interbody/intravertebral body device 28*c* also includes a first side component 76 and a second side component 78. The first end plate 72 is pivotally connected at one side thereof to the first side component 76 by a first hinge component 93 via hinge plates 86 and 87 of the first hinge component 93, and pivotally connected at another side thereof to the second side component 78 by a second hinge component 94 via hinge plates 84 and 85 of the second hinge component 94. In like manner, the second end plate 74 is pivotally connected at one side thereof to the first side component 76 by a third hinge component 91 via hinge plates 82 and 83 of the third hinge component 91, and pivotally connected at another side thereof to the second side component 78 by a fourth hinge component 92 via hinge plates 80 and 81 of the fourth hinge component 92.

The interbody/intravertebral body device 28*c* further includes an expansion/contraction member (threaded shaft or screw) 90 that extends through a bore 88 of the second side component 78 and into the head 77 associated with the first side component 76. Expansion of the interbody/intravertebral body device 28*c* from the collapsed position as depicted in FIGS. 7-10 to the fully expanded position depicted in FIGS. 11-13 is accomplished by pushing the first and second side components 76 and 78 towards each other. As the threaded shaft 90 is rotated, the first and second side components 76, 78 are drawn towards one another. This pivots the first and second end plates 72 and 74 away from each other via the first, second, third and fourth hinge components 93, 94, 91, and 92 respectively.

The interbody/intravertebral body device 28*c* may be dimensioned as necessary. However, currently it has been found that an optimum implant footprint is approximately 6.35 mm by 9.00 mm. Moreover, the interbody/intravertebral body device 28*c* is preferably, but not necessarily, dimensioned to have an optimal distraction of 16.00 mm and a maximum distraction of 22.00 mm. As such, the interbody/intravertebral body device 28*c* is deliverable (implantable) via a minimally invasive tube delivery (e.g. 8 mm tube delivery). Furthermore, the expansion member (e.g. screw) is designed to be a torque limiting break-away screw.

Figure 14:
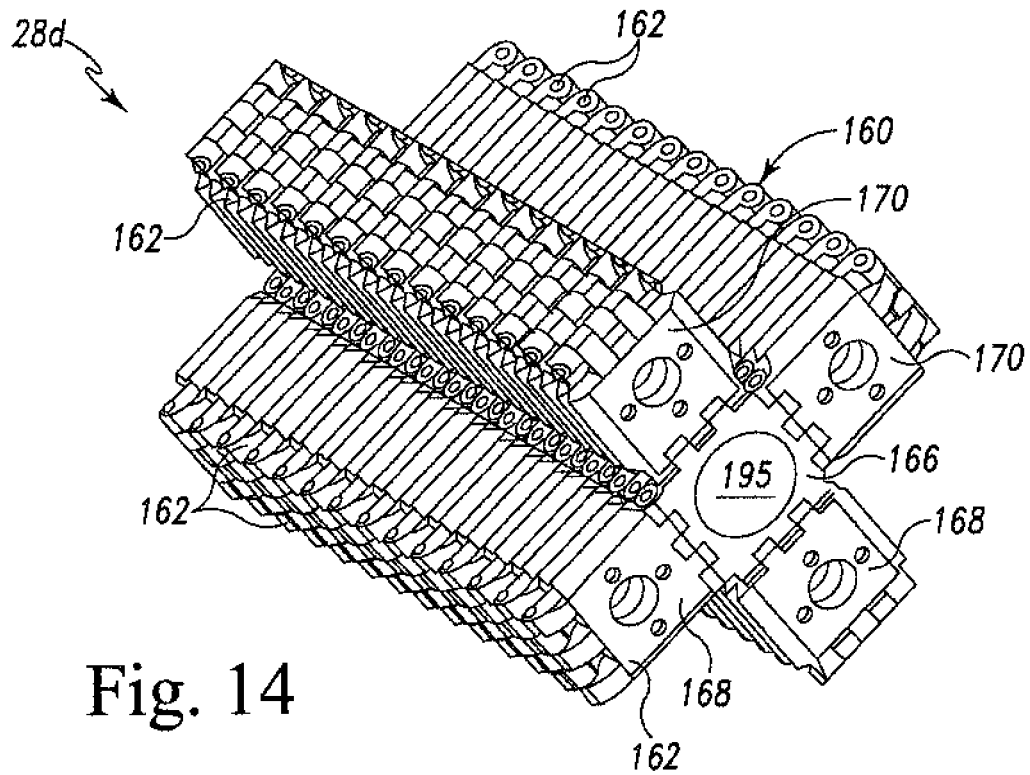
FIG. 14 is front a perspective view of an exemplary embodiment of an expandable interbody/intravertebral body device in accordance with the present principles, the interbody/intravertebral body device shown in a post-implant or expanded state.
Figure 15:
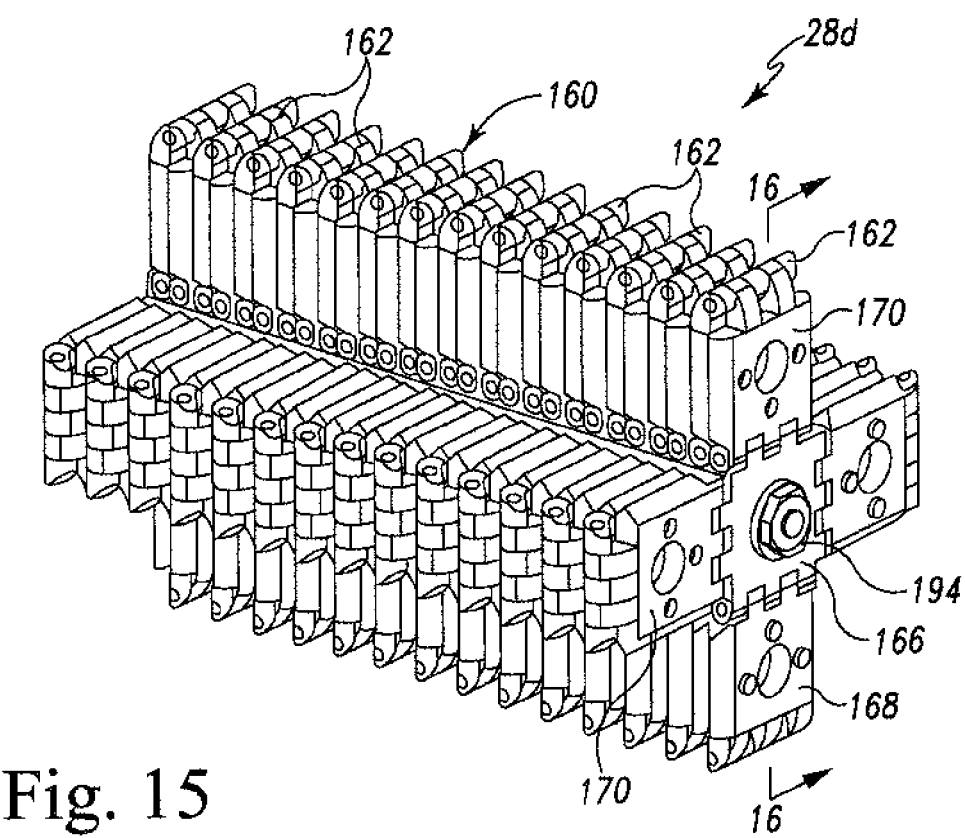
FIG. 15 is a rear perspective view of the expandable interbody/intravertebral body device of FIG. 14.
Figure 18:
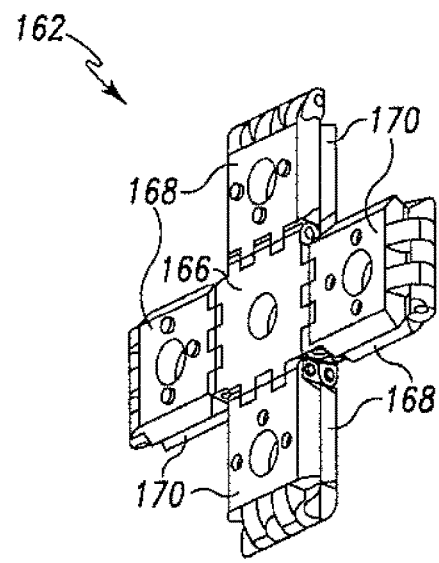
FIG. 18 is a perspective view of the single segment of FIG. 17.
Figure 19:
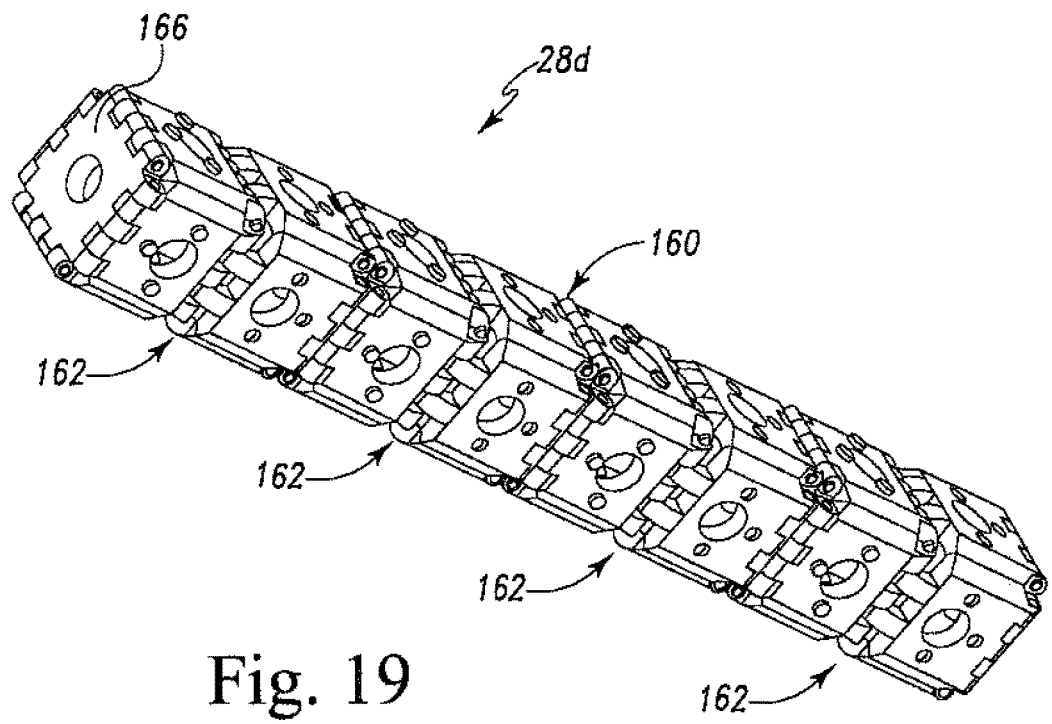
FIG. 19 is a perspective view of a plurality of expandable interbody/intravertebral body segments axially situated one to another forming an implant, the segments shown in a pre-implant or unexpanded state.

Referring to FIGS. 14-22 there is depicted another dynamic interbody/intravertebral body device generally designated 28*d*. The interbody/intravertebral body device 28*d* is characterized by a body structure 160 formed by a plurality of dynamic (expands and contracts) sections or portions 162. In FIGS. 14-16, the interbody/intravertebral body device 28*d* is shown in an expanded or (post) implanted state. In FIG. 19, the interbody/intravertebral body device 28*d* is shown in a collapsed, folded or pre implant state. In like manner, FIG. 18 depicts one section 162 in an expanded state Each section 162 is formed from three basic plates or components; i.e. an end plate 166 (see FIG. 20) used as a front plate and a back plate, a first inter-connect plate 168 (see FIG. 71) used as type I side plates, and a second inter-connect plate 170 (see FIG. 72) used as type II side plates. The various plates 166, 168 and 170 are pivotally or hingedly coupled to one another to form a section 162 such that the unexpanded box-like structure of each section collapses or folds into an expanded state.

Referring specifically to FIG. 20, end plate 166 is characterized by a rectangular and preferably, but not necessarily, generally square body 167 having a central bore 172. The body 167 includes a plurality of like hinge flanges 174 each having a hinge bore 175 therethrough for receiving a hinge pin. The body 167 includes a first side having three hinge flanges 174, a second side adjacent the first side and having three hinge flanges 174, a third side adjacent the second side (and opposite the first side) and having two hinge flanges 174, and a fourth side adjacent the third and first sides (and opposite the second side) and having two hinge flanges 174.

Referring specifically to FIG. 21, first inter-connect plate 168 is characterized by a rectangular and preferably, but not necessarily, generally square body 169 having a central bore 176. The body 169 includes two hinge flanges 178 of a first configuration each having a hinge bore 179 therethrough for receiving a hinge pin. The two hinge flanges 178 are disposed on one side of the body 169. The body 169 also includes three hinge flanges 180 of a second configuration each having a hinge bore 181 therethrough for receiving a hinge pin disposed on a side of the body 169 opposite the two hinge flange side. Additionally, the body 169 includes a plurality (here shown as three) semi-perf locaters 182 having a raised portion on one side and an indentation on the other side.

Referring specifically to FIG. 22 second inter-connect plate 170 is characterized by a rectangular and preferably, but not necessarily, generally square body 171 having a central bore 184. The body 171 includes two hinge flanges 186 of a first configuration each having a hinge bore 187 therethrough for receiving a hinge pin. The two hinge flanges 186 are disposed on one side of the body 171. The body 171 also includes three hinge flanges 188 of a second configuration each having a hinge bore 189 therethrough for receiving a hinge pin disposed on a side of the body 171 opposite the two hinge flange side. Additionally, the body 171 includes a plurality (here shown as three) semi-perf locaters 190 having a raised portion on one side and an indentation (seen in FIG. 22) on the other side. The semi-perf locaters help lock the parts together when the section is expanded. Holes and taper pins may also be used.

The expandable interbody/intravertebral body device 28d may be termed a quad directional interbody/intravertebral body device (e.g. fusion cage) or intervertebral device (e.g. interbody/intravertebral body) that is constructed with interlocking, hinged segments. The expandable interbody/intravertebral body device 28d has an implant footprint (distraction size) of 18.00 mm×18.00 mm (for a size 7 inner segment size). The expandable interbody/intravertebral body device 28d provides push action delivery. A minimally invasive (8 mm) tube delivery may be used. Segments or sections (262) may be added as needed. Preferably, the interbody/intravertebral body device 28d is fashioned from all titanium, but may be fashioned from other biocompatible material. When distracted, there is a 2 mm segment width. The interbody/intravertebral body device 28d may be provided in various sizes ranging from a size 1 through a size 7 with the size 1 having an inner segment size of 4.44 mm and distraction size of 12.00 mm, the size 2 having an inner segment size of 4.81 mm and distraction size of 13.00 mm, the size 3 having an inner segment size of 5.18 mm and distraction size of 14.00 mm, the size 4 having an inner segment size of 5.55 mm and distraction size of 15.00 mm, the size 5 having an inner segment size of 5.92 mm and distraction size of 16.00 mm, the size 6 having an inner segment size of 6.29 mm and distraction size of 17.00 mm, and the size 7 having an inner segment size of 6.66 mm and distraction size of 18.00 mm.

After insertion of the pre-implant structure, a threaded rod 192 having retained the pre-implant structure together during implantation via a head 195, is drawn out by a tool inserted into bore 193 to force the sections 162 to collapse and thus expand. A nut 194 is threadedly received on an exposed end of the rod 192 to retain the body 160 in the expanded state.

Referring to FIGS. 23-51 there is depicted another embodiment of an expandable vertebral interbody/intravertebral body device generally designated 28e. The expandable interbody/intravertebral body device 28e is radially expandable upon axial compression. Radial expansion provides vertical (co-spinal) height within a vertebral body area (see e.g. FIG. 1 area 26). Thus, the interbody/intravertebral body device 28e is characterized by the ability to be inserted or implanted into an open vertebral space in a folded or unexpanded, radially compact state or position and then be unfolded or expanded. The interbody/intravertebral body device 28e is formed of titanium, stainless steel or other biocompatible material, including composites, plastics and/or the like. Radiolucent materials may also be used and, the interbody/intravertebral body device 28e (as well as the other interbody/intravertebral body devices herein) may be formed entirely of a radiolucent material.

Figure 23:
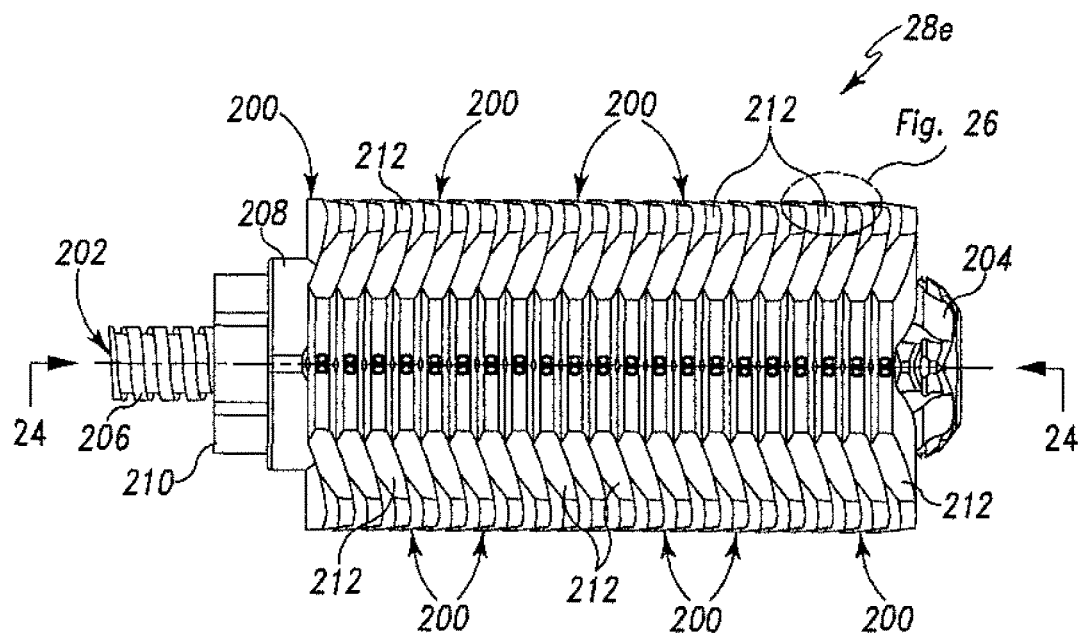
FIG. 23 is a side view of an exemplary embodiment of an expandable interbody/intravertebral body device in accordance with the present principles, the expandable interbody/intravertebral body device shown in a post-implant or expanded state.
Figure 24:
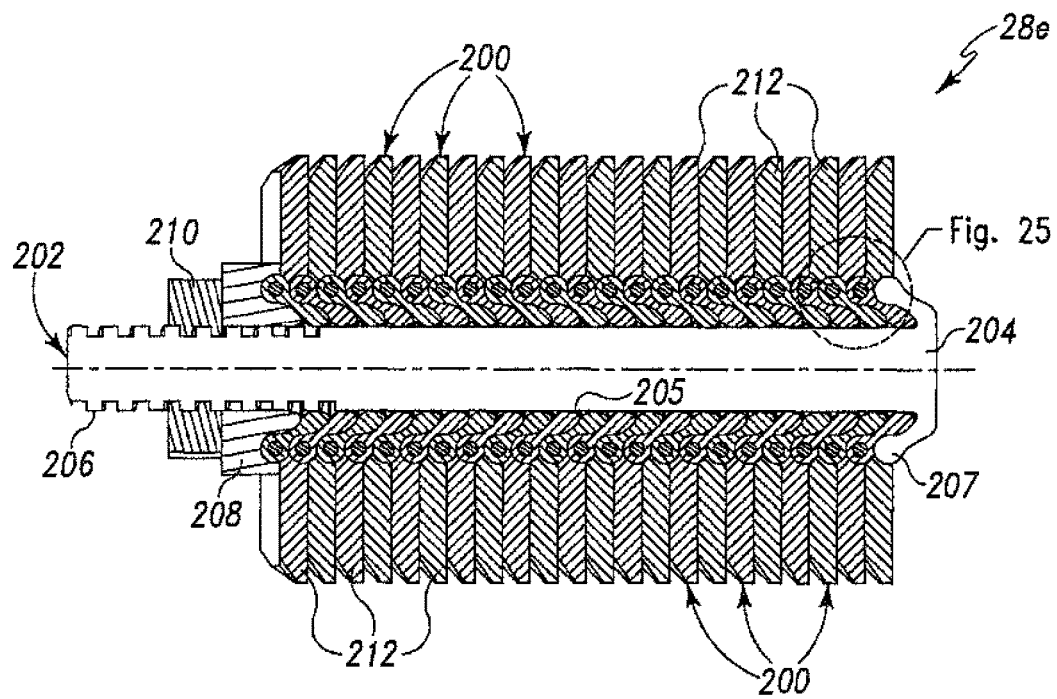
FIG. 24 is a cross-sectional view of the expandable interbody/intravertebral body device of FIG. 23 taken along line 24-24 thereof.
Figure 27:
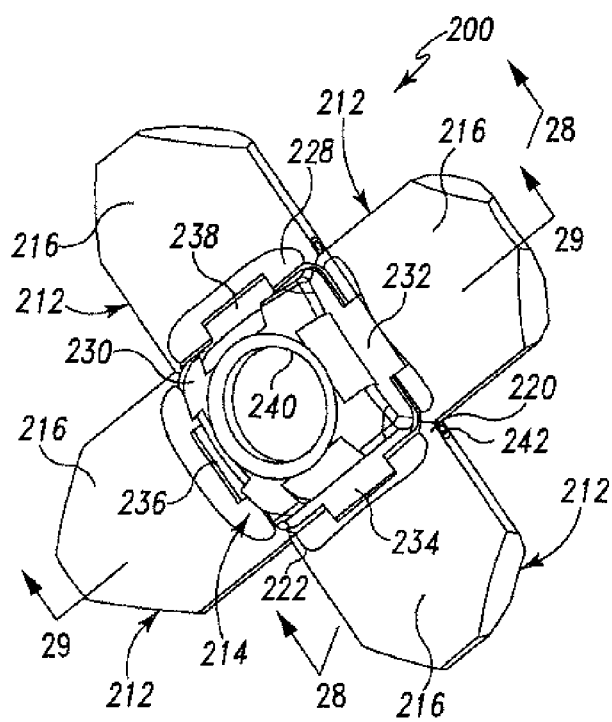
FIG. 27 is an enlarged perspective view of a segment or section of the expandable interbody/intravertebral body device of FIG. 23 in an expanded state.
Figure 30:
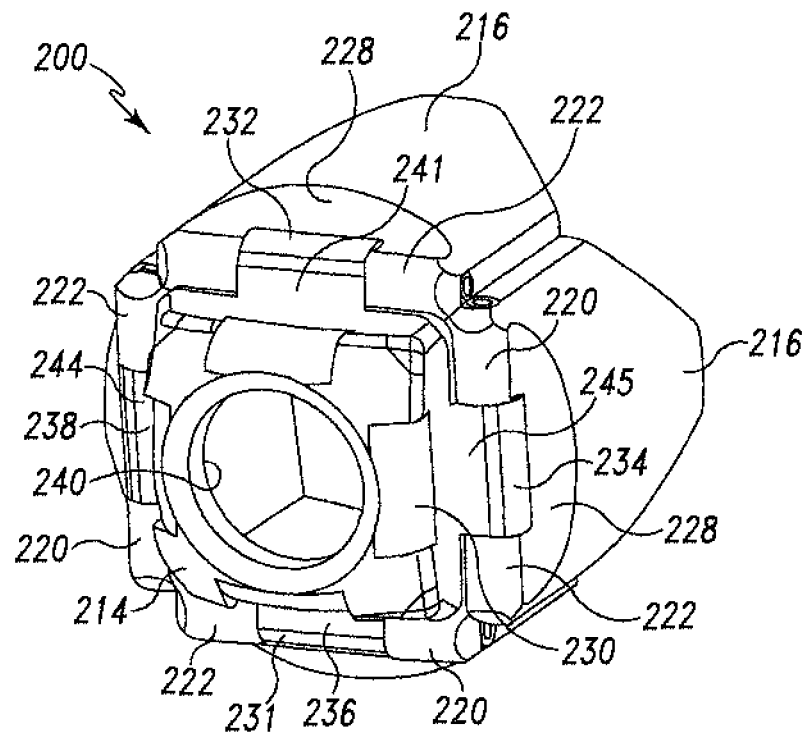
FIG. 30 is an enlarged perspective view of the interbody/intravertebral body segment of FIG. 27 shown in a folded or retracted state.

The interbody/intravertebral body device 28e is shown in an expanded position in FIGS. 23 and 24. The interbody/intravertebral body device 28e is characterized by a plurality of segments or sections 200 that each individually expand from a collapsed or unexpanded position into an extended or expanded position to form a vertebral interbody/intravertebral body device. FIG. 46 depicts the interbody/intravertebral body device 28e in a collapsed, folded or pre-deployment position such as after being assembled for introduction or insertion into a vertebral space. FIG. 27 depicts a segment 200 in an expanded or open position such as is seen in FIGS. 23 and 24. FIG. 30 depicts a segment 200 in a collapsed or folded position. The expandable vertebral interbody/intravertebral body device 28e is thus composed of a plurality of segments 200, the number and width thereof defining the overall axial length of the interbody/intravertebral body device 28e when expanded, with the number and axial length of leaves 212 (see, e.g. FIGS. 37-41) of the segments 200 defining the overall radial height of the interbody/intravertebral body device 28e when expanded.

The plurality of segments 200 is carried on an insertion and deployment rod 202. A deploy head or cap 204 is provided at the end of the rod 202 and is preferably integral therewith. The deploy head 204 is configured to engage, cooperate and interact with a central or middle deploy plate 214 of the segment 200. Particularly, a flange structure 207 of the rod 202 engages respective grooves (see FIG. 35 wherein three grooves 241, 244 and 245 of the four grooves of the deploy plate 214 are shown) of the deploy plate 214 (see also FIG. 25). The flange structure 207 represented in FIG. 24 is illustrated in FIGS. 42 and 43. The flange structure of the head 204 consists of four flanges 269, 270, 271 and 272 carried on a rectangular body 266. The four flanges are respectively received in the four grooves of the deploy plate 214. As described further below, axial compression of the deploy plate of the segment and the head of the rod causes the leaves 212 to pivot from an axial position to a position perpendicular to the axial position.

As best seen in FIG. 42, the rod 202 has a threaded shaft portion 206 and a non-threaded shaft portion 205. The non-threaded shaft portion 205 allows the segments 200 to axially slide during expansion of the segments 200. The threaded portion 206 threaded receives the nut 210 allows it to provide the axial force for axial compression of the segments 200 and the expansion thereof.

An end cap 208 is provided on the rod 202 distal from the head 204 of the rod 202 and between the nut 210 and the last (from left to right) deploy plate 214 of the last segment 200. The end cap 208 abuts against the central deploy plate 214 of the last segment 200. The nut 210 abuts the end cap 208. Particularly, the end cap 208 has four grooves 249, 251, 253 and 255 (see FIG. 33) that correspond to the four tubular flanges or hinge structures (which will be referred to as tubular hinge structures 232, 234, 236 and 238) of the central deploy plate 214. The tubular hinge structures of the deploy plate 214 are nested or received into the grooves of the end plate 208. Moreover, a threaded nut 210 is provided on the rod 202 to provide axial compression of the segments 200 when threadedly advanced toward the head 204 of the rod 202 to achieve radial expansion of the interbody/intravertebral body device 28e. This is done after proper placement of the interbody/intravertebral body device 28e into a vertebral space 26.

As seen in FIGS. 33 and 34, the end cap 208 is particularly characterized by a body 246 having a central or middle bore 247 that is sized to be received onto the rod 202. The body 246 defines four flanges 248, 250, 252 and 254 on sides thereof. The four flanges 248, 250, 252 and 254 each define a respective groove 249, 251, 253 and 255 and a respective contact surface 262, 256, 260 and 258. The grooves 249, 251, 253 and 255 providing a contact surface for the tubular hinge structures 232, 234, 236 and 238 of the deploy plate 214.

Figure 26:
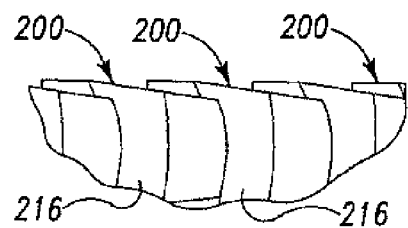
FIG. 26 is an enlarged portion of the side view of the expandable interbody/intravertebral body device of FIG. 23.
Figure 25:
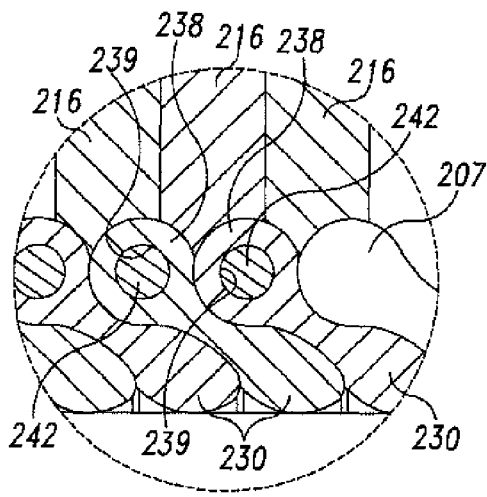
FIG. 25 is an enlarged portion of the sectional view of the expandable interbody/intravertebral body device of FIG. 24.
Figure 28:
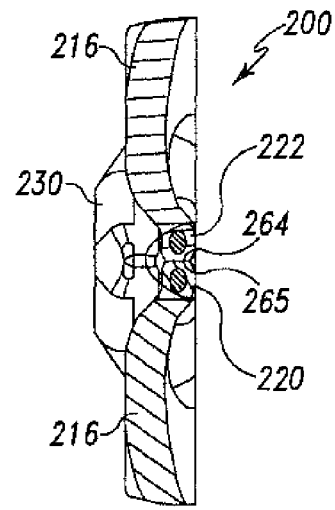
FIG. 28 is a sectional view of the interbody/intravertebral body segment of FIG. 27 taken along line 28-28 thereof.
Figure 29:
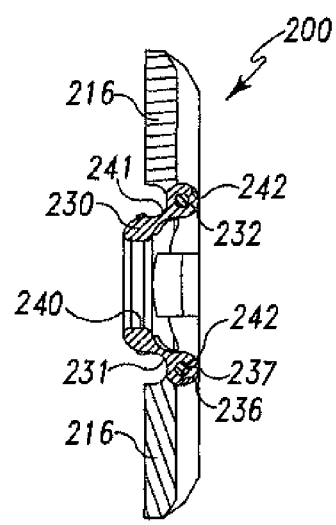
FIG. 29 is a sectional view of the interbody/intravertebral body segment of FIG. 28 taken along line 29-29 thereof.
Figure 31:
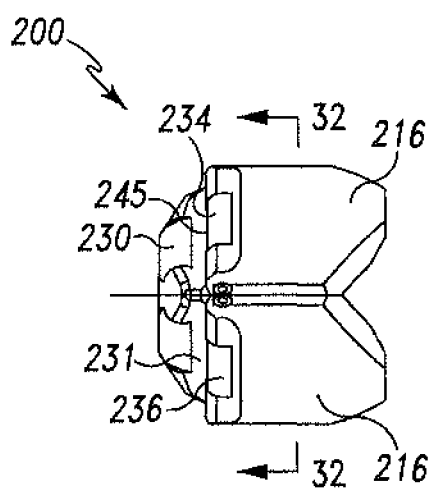
FIG. 31 is a side view of the folded interbody/intravertebral body segment.
Figure 32:
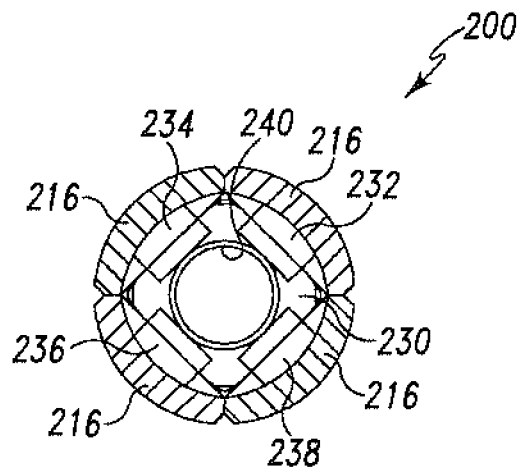
FIG. 32 is a sectional view of the folded interbody/intravertebral body segment of FIG. 31 taken along line 31-31 thereof.
Figure 37:
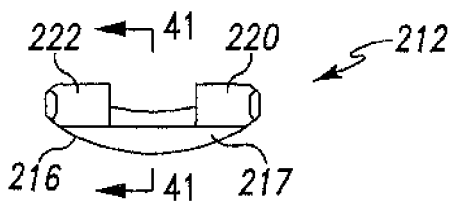
FIG. 37 is a front view of a leaf of the interbody/intravertebral body segment.
Figure 38:
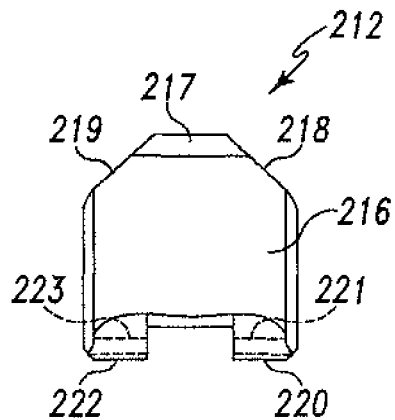
FIG. 38 is a bottom view of the leaf of the interbody/intravertebral body segment.
Figure 39:
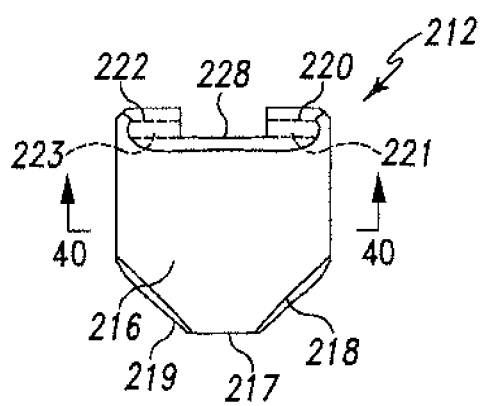
FIG. 39 is a top view of the leaf of the interbody/intravertebral body segment.
Figure 40:
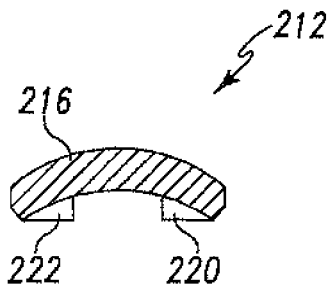
FIG. 40 is a sectional view of the leaf of the interbody/intravertebral body segment taken along line 40-40 of FIG. 39.
Figure 41:
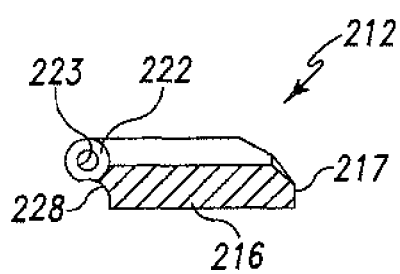
FIG. 41 is a sectional view of the leaf of the interbody/intravertebral body segment taken along line 41-41 of FIG. 37.
Figure 48:
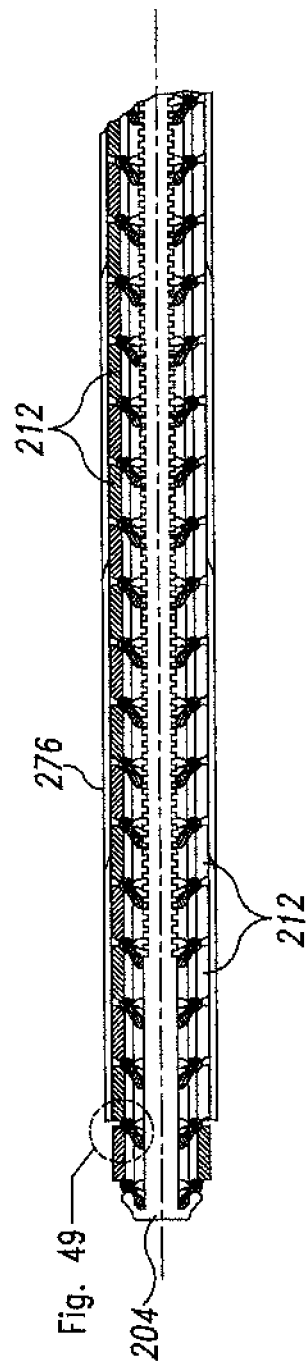
FIG. 48 is a sectional view of FIG. 47 taken along line 48-48 thereof.

As seen in FIGS. 27-32, the segments 200 include the middle or central deploy plate 214 (see FIG. 33) to which are pivotally, hingedly or swingably attached a plurality (here, four) leaf structures 212. The leaf structures 212 are pivotally attached to the deploy plate 214 by hinge pins 242 and are structured to provide a collapsed or folded position as seen in FIGS. 30-32 wherein a longitudinal axis of each leaf structure 212 is essentially co-axial with the rod 202, and an expanded or open position as seen in FIGS. 27-29 where the longitudinal axis of each leaf structure 212 is essentially perpendicular to the longitudinal axis of the rod 202. The folded position of the segments 200 provide a small diameter device, while the expanded position of the segments 200 provides a larger diameter device constrained by the length of the leaf structures 212. As illustrated in FIG. 26, the leaf bodies 216 of the segments 200 form a toothed, stepped or jagged profile.

Referring to FIGS. 35 and 36, the deploy plate 214 of a segment 200 is particularly shown. The deploy plate 214 is characterized by a generally rectangular body 230 having a central or middle bore 240. The bore 240 is sized to be received onto the rod 202. Four cylindrical or tubular hinge structures 232, 234, 236 and 238 extend from the four sides of the body 230. Each tubular hinge structure 232, 234, 236 and 238 has a bore 233, 235, 237 and 239 respectively for receipt of a pivot pin 242. The body 230 also defines four grooves 241, 245, 231, and 244 adjacent the four hinge structures 232, 234, 236 and 238 respectively.

Referring to FIGS. 37-41 the leaf structure 212 of a segment 200 is particularly shown. A leaf structure 212 consists of a leaf body 216 having a generally "home-plate" shape (see e.g., FIGS. 38, 39) with an arched profile (see e.g., FIGS. 37, 40). As such, the body 216 includes a front 217 and two angled portions 218, 219. First and second tubular or cylindrical pivot flanges 220, 222 are provided on one side 228 of the body 216. The first flange 220 includes a bore 221 for receipt of a pivot pin 242. The second flange 222 includes a bore 223 for receipt of a pivot pin 242. The two flanges 220 and 222 are spaced from one another so as to receive a tubular flange (e.g. hinge structure 232) of the deploy plate body 230 such that the two flanges 220, 222 of the leaf body 216 straddle or are on opposite axial sides of the respective deploy plate tubular flange. In this manner a pivot pin 242 may extend through the flange 220 of the leaf body 216, the tubular flange of the deploy plate body 230, and though the flange 222 of the leaf body 216. When four leaf structures 212 are connected to the middle body 230, the leaf bodies 216 can pivot between a closed, folded or collapsed position (FIG. 30) and an open, extended or expanded position (FIG. 27).

As best seen in FIG. 28, when the leaf structures 212 are expanded, the rounded flanges 220 and 222 and flats 264 and 265 on ends of the flanges 220 and 222 of the leaf body 216 coact to provide a positive or snap feature to lock the leaf structures 212 in the expanded position.

The interbody/intravertebral body/intervertebral body device 28e, like the other interbody/intravertebral body device described herein, are designed to be delivered, installed, implanted or positioned in a patient via a cannula or tube. Such a cannula 274 is illustrated in FIGS. 44 and 45. The cannula 274 is defined by a tubular body 276 having an inner or inside surface 278. Four prongs or protrusions 280, 281, 282 and 283 are provided on the inside surface 278. These serve to guide, orient and allow expansion of the interbody/intravertebral body device 28 during implantation.

Figure 49:
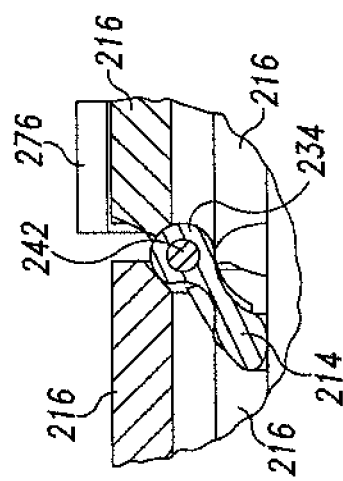
FIG. 49 is an enlarged, sectional portion of FIG. 48.

FIGS. 46-49 provide an illustration of the interbody/intravertebral body device 28e assembled for being implanted in a vertebral space. FIG. 46 shows an interbody/intravertebral body device 28e assembled and in a collapsed position. The number of segments 200 determines the overall axial length of the resulting expanded device. The assembled and collapsed interbody/intravertebral body device is provided in the cannula 274 in FIG. 47. A sectional view of FIG. 47 is provided in FIG. 48. FIG. 49 particularly depicts the juncture of the end of the cannula 274 and a segment 200 of the interbody/intravertebral body device 28e. At this point, a first segment may be deployed (expanded).

Figure 51:
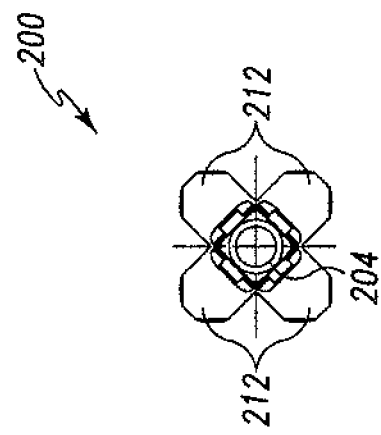
FIG. 51 is an end view of the interbody/intravertebral body device of FIG. 50 taken along line 51-51 thereof.
Figure 50:
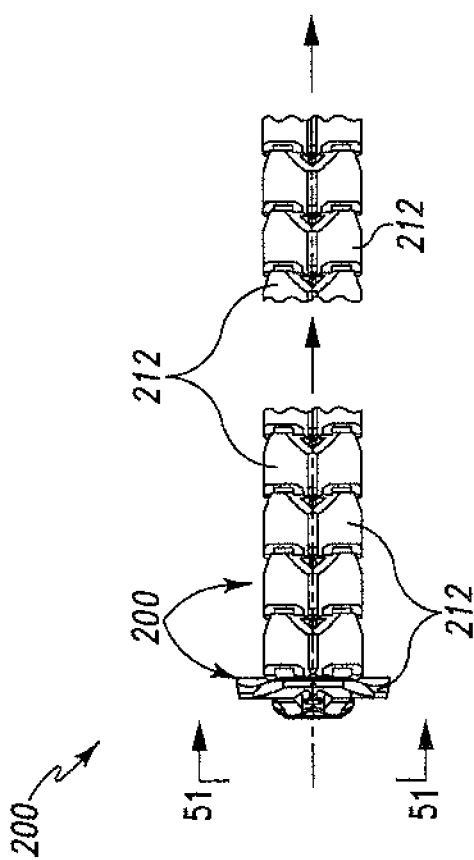
FIG. 50 is a side view of the folded expandable interbody/intravertebral body device of FIG. 46 illustrating deployment thereof.

FIGS. 50 and 51 particularly illustrate how axial compression (represented by the arrows) causes the segments 200 to expand. Particularly, axially compression causes a first segment 200 to expand. Thereafter, each successive segment expands in a somewhat "domino" effect as more axial compression is applied. In this embodiment, axial compression is provided by the nut 210. Thus, when the interbody/intravertebral body device 28e is properly placed, the nut 210 is rotated to provide axial compression until all of the segments 200 are expanded.

Figure 52:
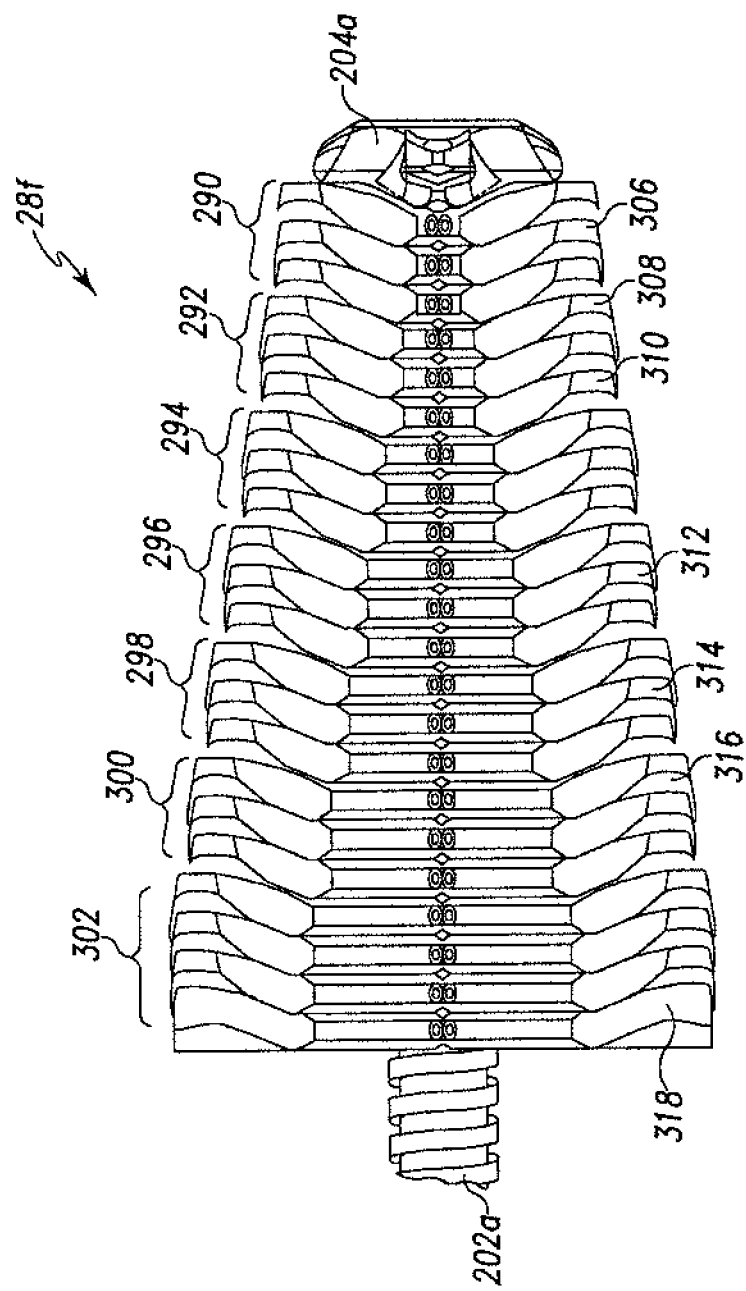
FIG. 52 is a perspective view of an exemplary embodiment of an expandable interbody/intravertebral body device in accordance with the present principles, the interbody/intravertebral body device shown in a post-implant or expanded position.
Figure 53:
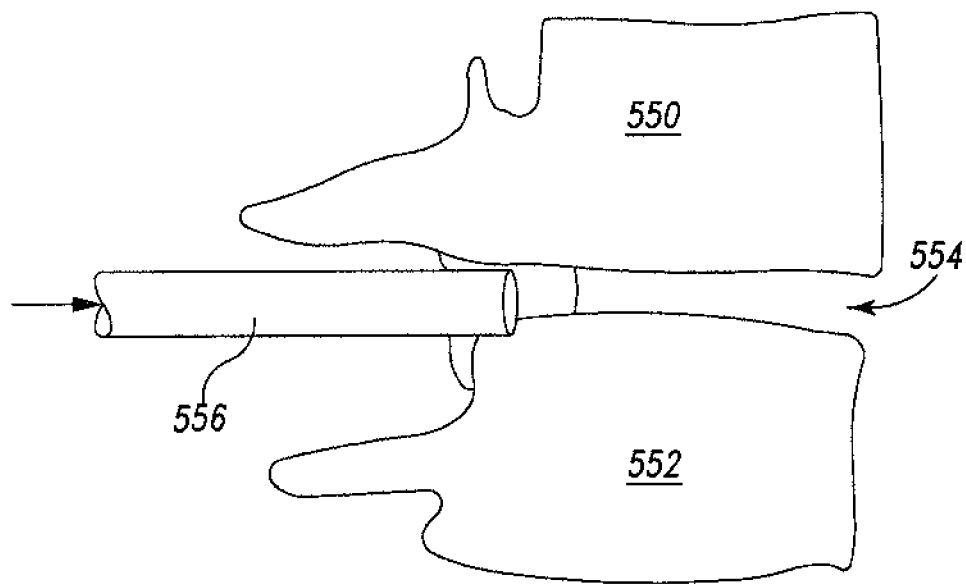
FIG. 53 is a side view of adjacent vertebrae with a cannula (insertion and deployment tube) used to introduce or implant an expandable interbody/intravertebral body device as provided herein.
Figure 54:
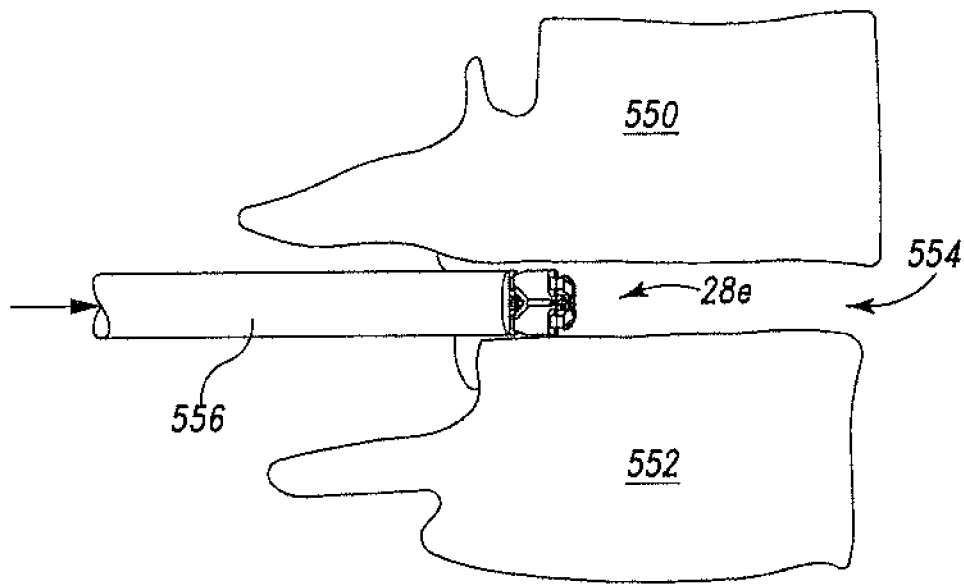
FIG. 54 is the view of FIG. 63 wherein an expandable interbody/intravertebral body device is being inserted between vertebrae.

FIG. 52 depicts an alternative embodiment or variation of the interbody/intravertebral body device 28e illustrating how different radial profiles may be created by using segments of various sizes (dimensions). In FIG. 52 there is depicted a frusto-conically shaped interbody/intravertebral body device generally designated 28f. The interbody/intravertebral body device 28f is shown in a post-implant or expanded state. The interbody/intravertebral body device 28f includes a plurality 290, 292, 294, 296, 298, 300 and 302 of groups of interbody/intravertebral body segments each group of segments 290, 292, 294, 296, 298, 300 and 302 having respective leaves 306, 308, 310, 312, 314, 316 and 318 of different radial height. As can be appreciated, the axial length of any group 290, 292, 294, 296, 298, 300 and 302 is determined by the number of segments in the group. The radial height or profile of each group 290, 292, 294, 296, 298, 300 and 302 is determined by the radial height of the leaf structures (and the middle plate) of the segments. A multitude of radial profiles may be created.

It should be appreciated that the segments 200 of the various interbody/intravertebral body devices may or may not be at least limitedly movable relative to one another. In one case, the segments 200 are fixed relative to each other and therefore no movement can occur between the segments. In another case, the segments 200 are at least limitedly movable radially with respect to another segment 200 such that the interbody/intravertebral body is dynamic. This allows for limited movement within the interbody/intravertebral body device itself.

Figure 55:
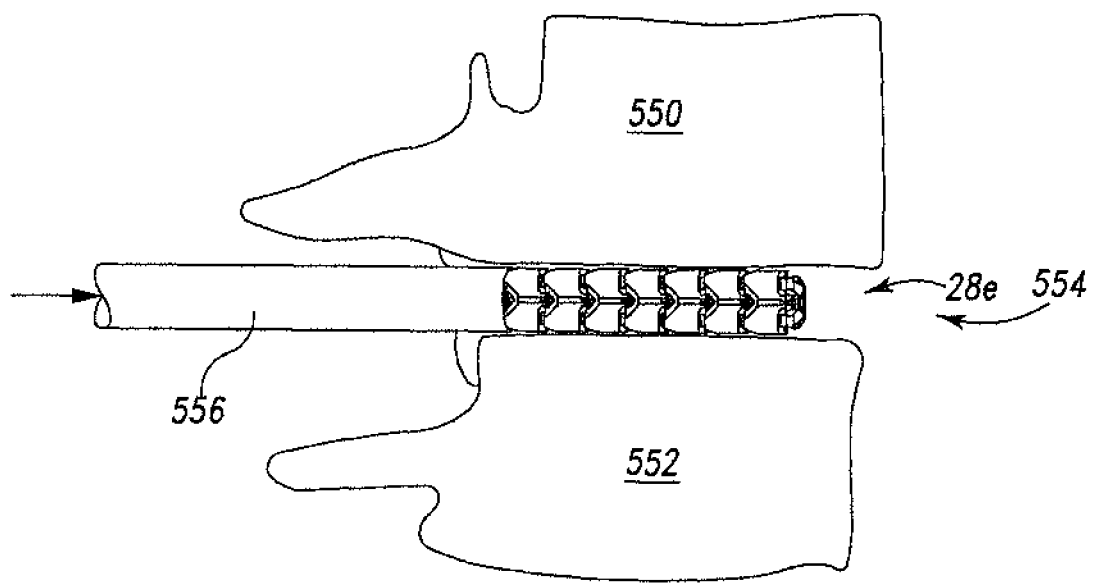
FIG. 55 is the view of FIG. 63 wherein the expandable interbody/intravertebral body device has been properly positioned for expansion/deployment.
Figure 56:
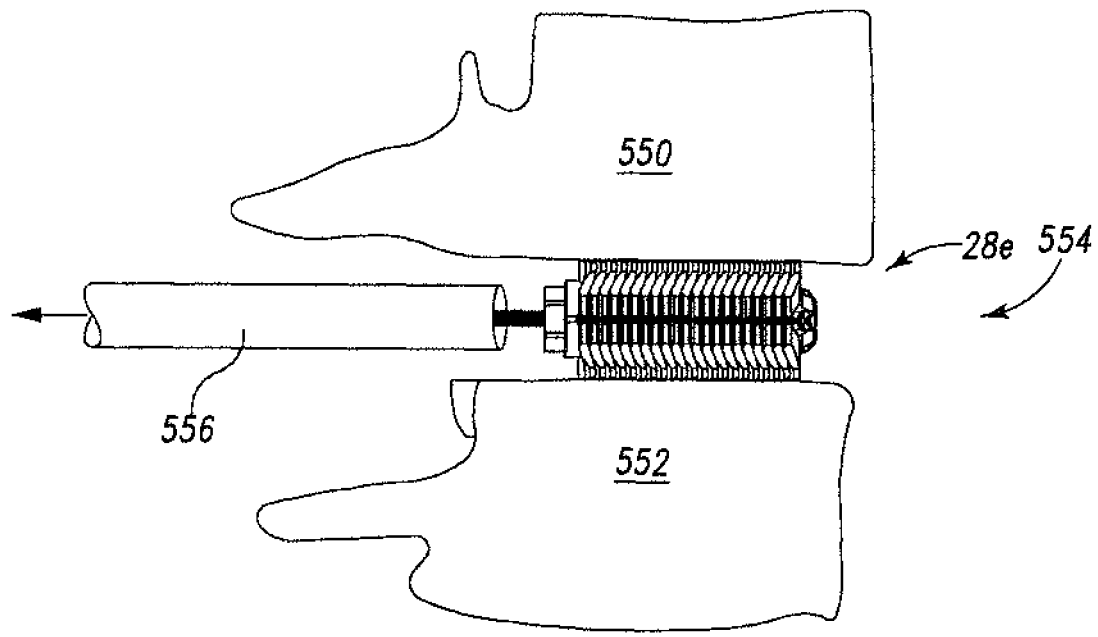
FIG. 56 is the view of FIG. 63 wherein the expandable interbody/intravertebral body device has been fully expanded or deployed.

Referring lastly to FIGS. 53-56, there is illustrated a manner of implanting the interbody/intravertebral body devices 28a-28f. Particularly, but without restriction or being necessarily so, the various interbody/intravertebral body devices 28a-28f are percutaneously implanted via a cannula 556. The end of the cannula 556 is positioned proximate an intervertebral space 554 between a first vertebra 550 and a second vertebra 552. The particular interbody/intravertebral body device (here, interbody/intravertebral body device 28e is shown) is then inserted into the cannula 556 as represented by the arrow. Once the particular interbody/intravertebral body device is appropriately placed in the intervertebral space 554, the interbody/intravertebral body device is expanded via an appropriate instrument through the cannula 556. As shown in FIG. 55 the interbody/intravertebral body device 28e is received in the vertebral space 554. In FIG. 56, the interbody/intravertebral body device 28e has been radially expanded to vertically fill the vertebral space 554 through axial compression of the segments 200 of the interbody/intravertebral body device 28e.

Figure 57:
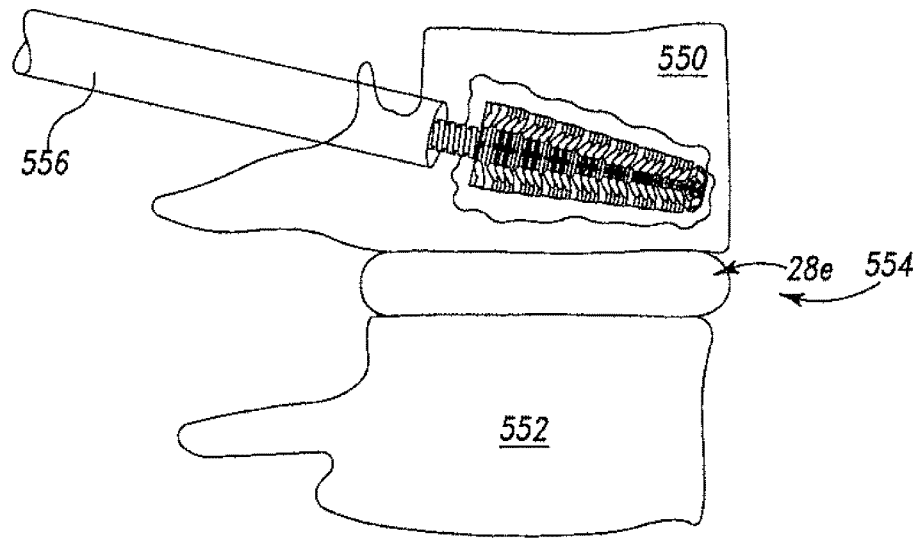
FIG. 57 is side view of a portion of a spinal column showing two adjacent vertebrae with a cannula (insertion and deployment tube) used to introduce or implant an expandable interbody/intravertebral body device as an intravertebral body device, the expandable intravertebral body device shown in an unexpanded position.
Figure 58:
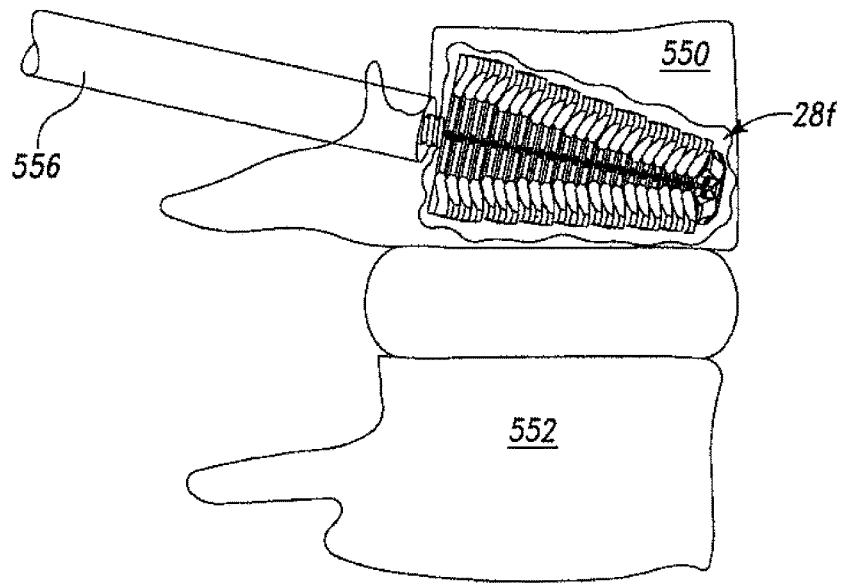
FIG. 58 is the view of FIG. 57 wherein the expandable intravertebral device is shown in an expanded position within the vertebra.

FIGS. 57 and 58 illustrate use of a spinal body 28 as an intravertebral body device. Particularly interbody/intravertebral body 28f is shown in FIG. 57 as implanted via cannula 556 into vertebra 550 (intravertebral). The intravertebral device 28f is initially unexpanded. In FIG. 58, the intravertebral device 28f has been expanded within the vertebra. This use is applicable to treat vertebral compression fractures and/or the like.

It should be appreciated that each interbody/intravertebral body device 28a through 28e may be scaled to any size necessary. Additionally, each interbody/intravertebral body device 28a-28e is manufactured from a bio-compatible material such as a titanium-based metal. Variations are also contemplated.

Referring now to FIGS. 59-74, a radially expandable implant 610 (e.g., an interbody device, and intrabody device, etc.) is shown according to an exemplary embodiment. Implant 610 is usable, for example, between and/or within vertebral bodies of the spine, and may share many of the features of the other inter/intra-body implants discussed elsewhere herein. However, it should be understood that implant 610 may have other uses in other portions of a patient's body (e.g., inside or around bone, such as a femur, as a cement restrictor, etc.). All such applications are understood to be within the scope of the present disclosure.

Figure 61:
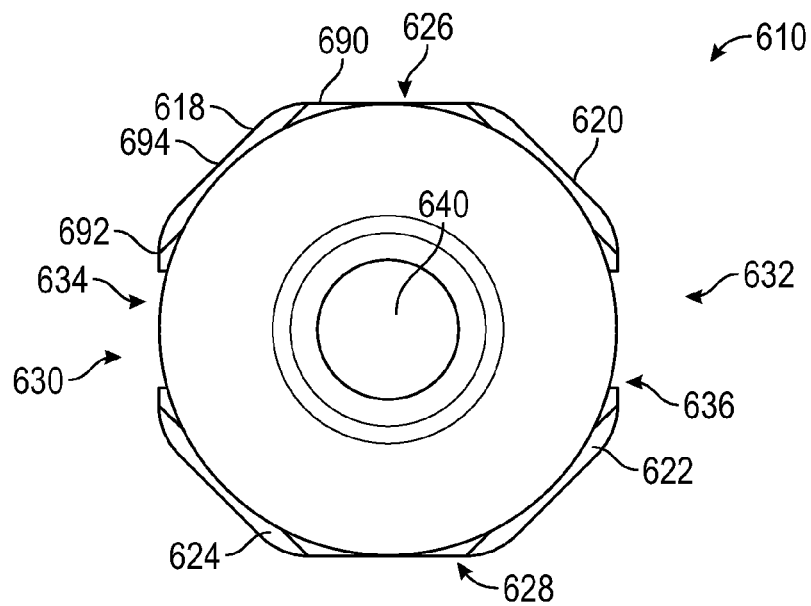
FIG. 61 is a front view of the implant of FIG. 59 according to an exemplary embodiment.

According to an exemplary embodiment, implant 610 includes a first portion 612 (e.g., a front member or portion, a narrowing member, a rounded member, etc.), a second portion 614 (e.g., a rear member or portion, a moveable member, etc.), and a third portion or control member 616 (e.g., a control rod or member, an intermediate member, a coupling member, etc.). First and second portions 612, 614 and control member 616 form a body assembly for implant 610 that extends along a longitudinal axis 688. A plurality of supports 618, 620, 622, 624 (e.g., moveable supports, elongated members, wings, etc.) are coupled to the body assembly and extend generally parallel to longitudinal axis 688. In one embodiment, as shown in FIG. 61, supports 618, 620, 622, 624 define a top and bottom 626, 628, and first and second sides 630, 632, of implant 610. Top and bottom 626, 628 define a height of implant 610, and first and second sides 630, 632 define a width of implant 610. First and second sides 630, 632 include longitudinal extending gaps, or spaces, 634, 636.

Figure 59:
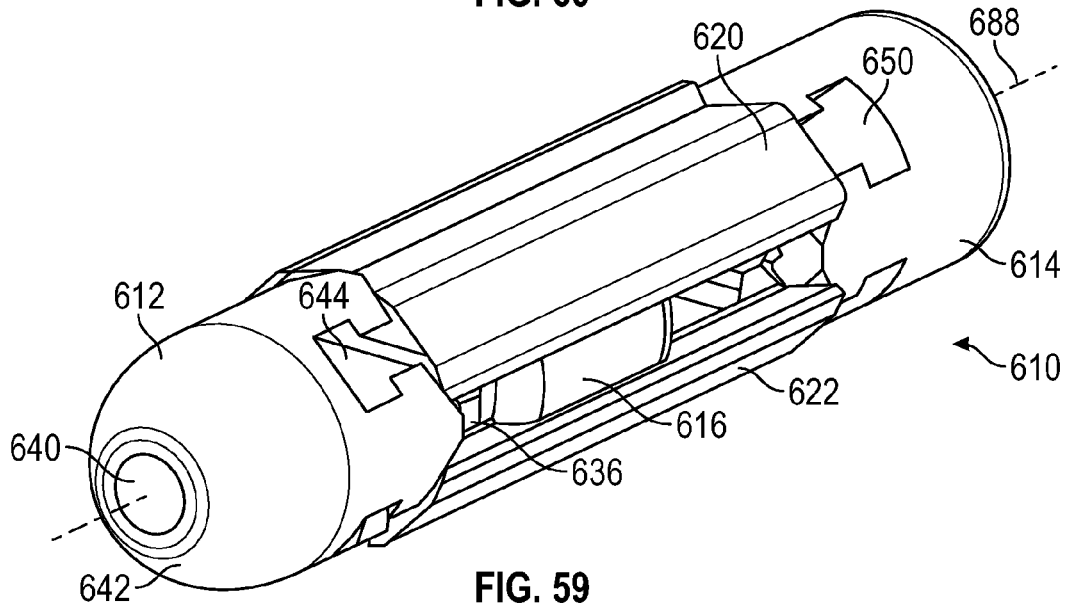
FIG. 59 is a perspective view of an implant in a collapsed configuration according to an exemplary embodiment.
Figure 68:
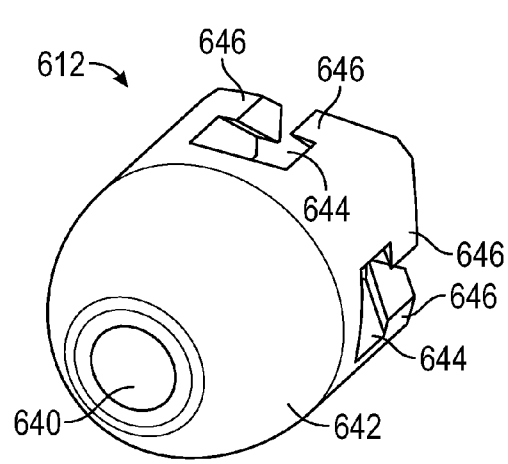
FIG. 68 is a perspective view of a front portion of the implant of FIG. 59 according to an exemplary embodiment.
Figure 69:
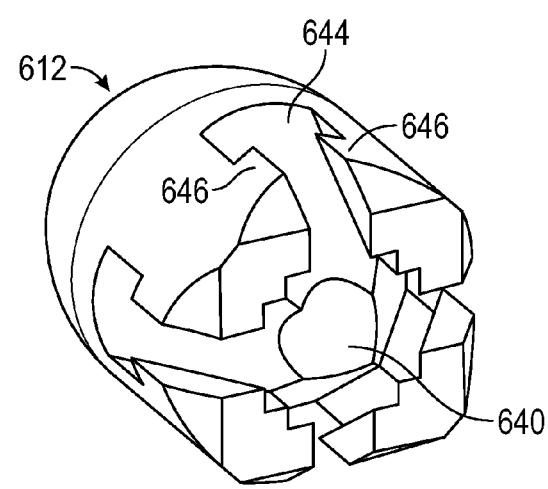
FIG. 69 is another perspective view of the front portion of FIG. 68 according to an exemplary embodiment.

As shown in FIGS. 59 and 68-69, first portion 612 includes a central bore 640 that receives control member 616. In some embodiments, first member 612 may threadingly receive control member 616. In other embodiments, first portion 612 and control member 616 may be integrally formed, welded, or coupled using any other suitable joining method. In some embodiments, first portion 612 may be rotationally and longitudinally fixed relative to control member 616. In other embodiments, first portion 612 may be longitudinally and/or rotationally moveable relative to control member 616.

First portion 612 further includes a tip portion 642 that may be rounded, bull-nosed, or otherwise have a contoured forward portion configured to facilitate insertion of implant 610 into a desired location with a patient (e.g., in a spinal space, etc.). First portion 612 may be generally cylindrical in shape rearward of tip portion 642, and may include a plurality of guide channels 644 configured to receive portions (e.g., first ends) of supports 618, 620, 622, 624. According to an exemplary embodiment, guide channels 644 are generally T-shaped and are formed in part by a pair of projections 646. In one embodiment, one guide channel 644 is provided for each support 618, 620, 622, 624, and guide channels 644 are equally spaced about the circumference of first portion 612. In other embodiments, more or fewer guide channels 644 may be provided, and the shape, location, and/or spacing of the guide channels may be varied.

Figure 67:
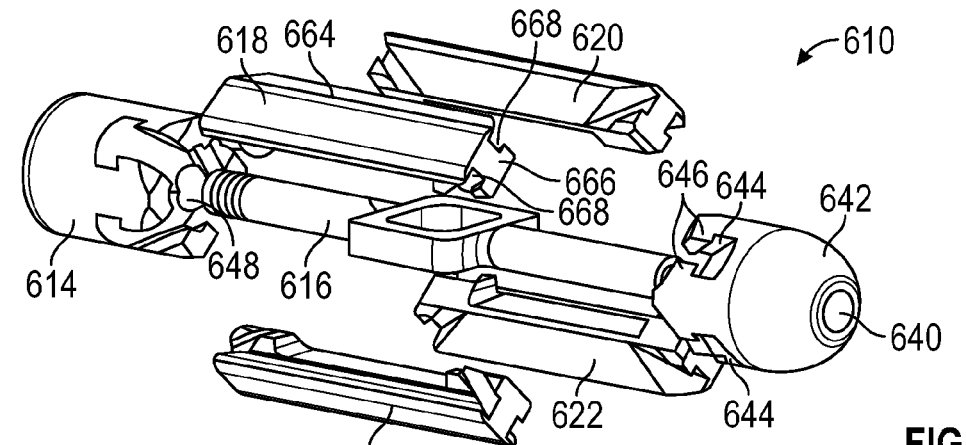
FIG. 67 is another perspective view of the implant of FIG. 59 according to an exemplary embodiment.
Figure 70:
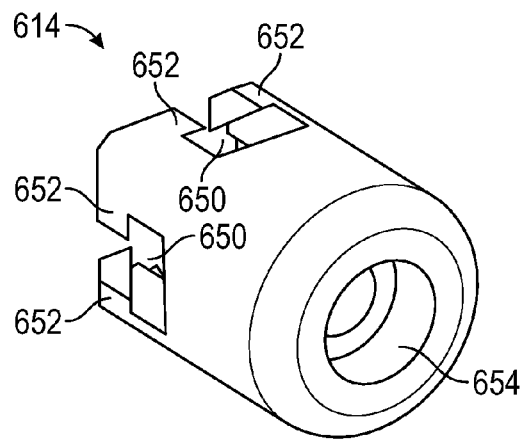
FIG. 70 is a perspective view of a rear portion of the implant of FIG. 59 according to an exemplary embodiment.
Figure 71:
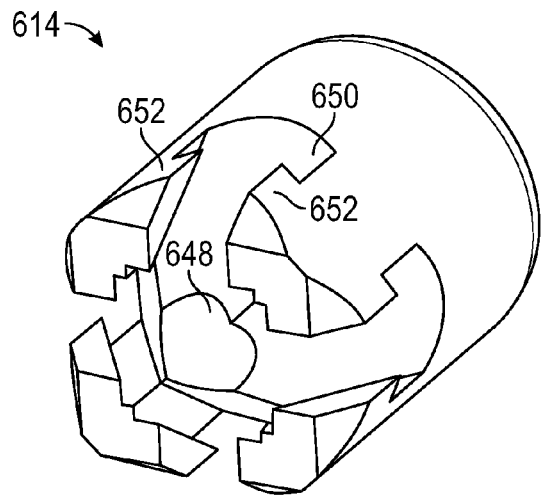
FIG. 71 is another perspective view of the rear portion of FIG. 70 according to an exemplary embodiment.

As shown in FIGS. 67 and 70-71, second portion 614 includes a central bore 648 that receives control member 616. In some embodiments, second portion 614 may be longitudinally moveable relative to control member 616 so as to vary the distance between first portion 612 and second portion 614. Second portion 614 may be generally cylindrical in shape rearward of tip portion 642, and may include a plurality of guide channels 650 configured to receive portions (e.g., second ends) of supports 618, 620, 622, 624. According to an exemplary embodiment, guide channels 650 are generally T-shaped and are formed in part by a pair of projections 652. In one embodiment, one guide channel 650 is provided for each support 618, 620, 622, 624, and guide channels 650 are equally spaced about the circumference of second portion 614. In other embodiments, more or fewer guide channels 650 may be provided, and the shape, location, and/or spacing of the guide channels may be varied.

According to an exemplary embodiment, the rearward end of second portion 614 includes a counterbore 654 configured to receive a collar 638 (e.g., a threaded collar, etc.). Collar 638 is configured to be received at least partially within counterbore 654 and be threadingly received on a threaded end 696 of control member 616. As the position of collar 638 changes longitudinally along control member 616, the position of second portion 614 relative to first portion 612 changes. As discussed in further detail below, rotation of collar 638 about control member 616 may be usable to control the distance between first and second portions 612, 614, and in turn the amount of radial expansion of supports 618, 620, 622, 624.

Figure 60:
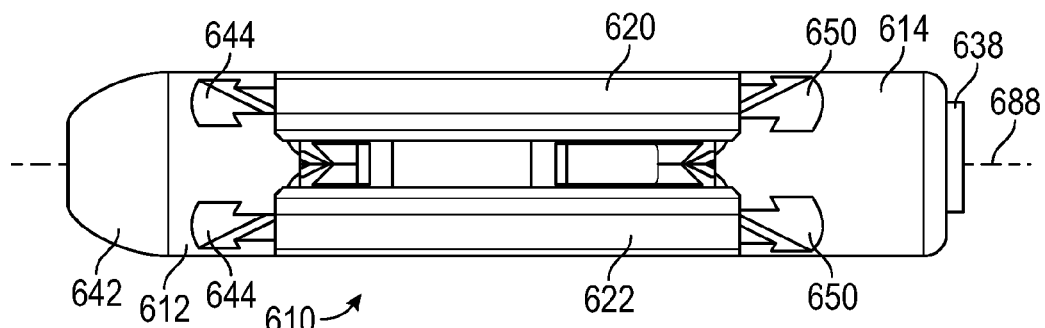
FIG. 60 is a side view of the implant of FIG. 59 according to an exemplary embodiment.
Figure 64:
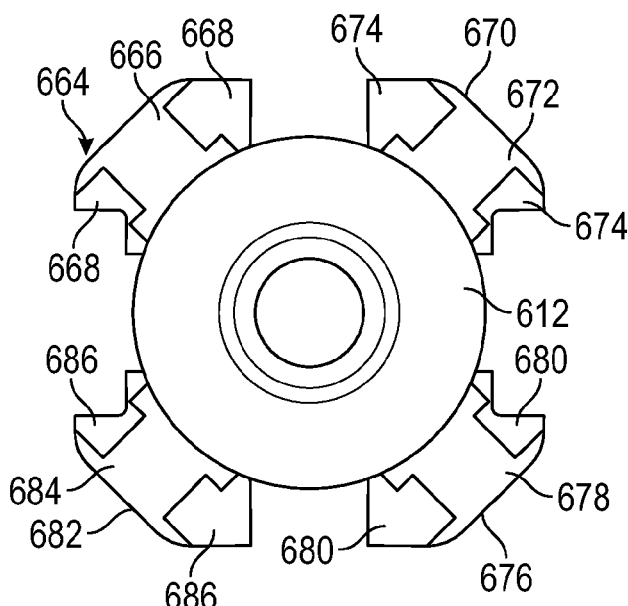
FIG. 64 is a front view of the implant of FIG. 59 in an expanded configuration according to an exemplary embodiment.
Figure 63:
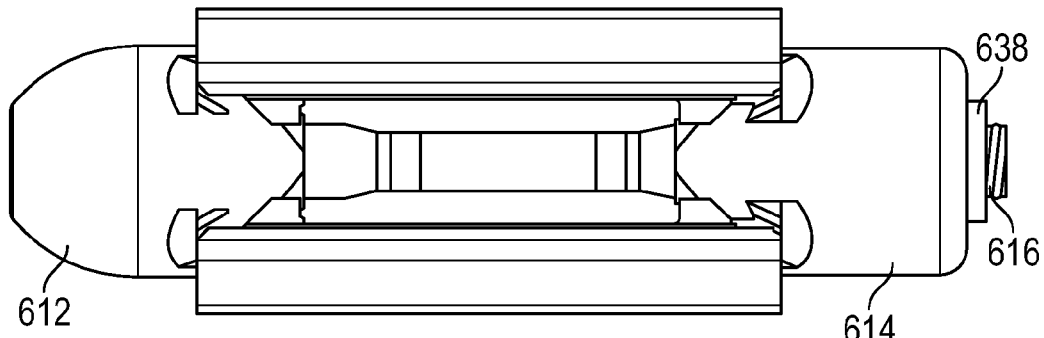
FIG. 63 is a side view of the implant of FIG. 59 is an expanded configuration according to an exemplary embodiment.
Figure 62:
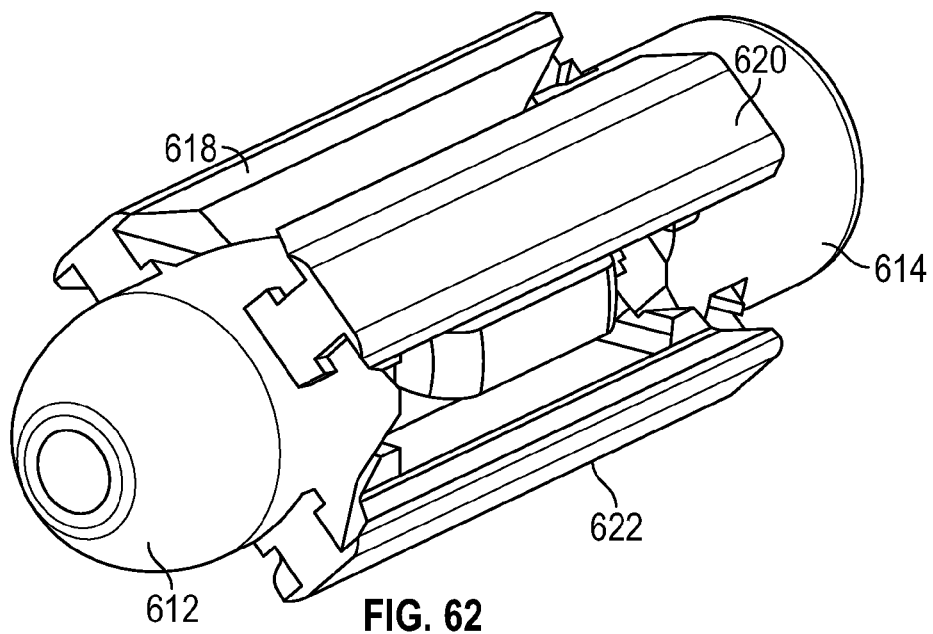
FIG. 62 is a perspective view of the implant of FIG. 59 in an expanded configuration according to an exemplary embodiment.

In one embodiment, supports 618, 620, 622, 624 are configured to be moveable relative to the body assembly (e.g., first and second portions 612, 614 and control member 616) in a radially outward direction (e.g., generally perpendicular to longitudinal axis 688) such that implant 610 is reconfigurable between a first configuration (e.g., a retracted, collapsed, or minimal configuration) as shown in FIGS. 59-61, and a second configuration (e.g., an expanded or maximum configuration), as shown in FIGS. 62-64.

Figure 66:
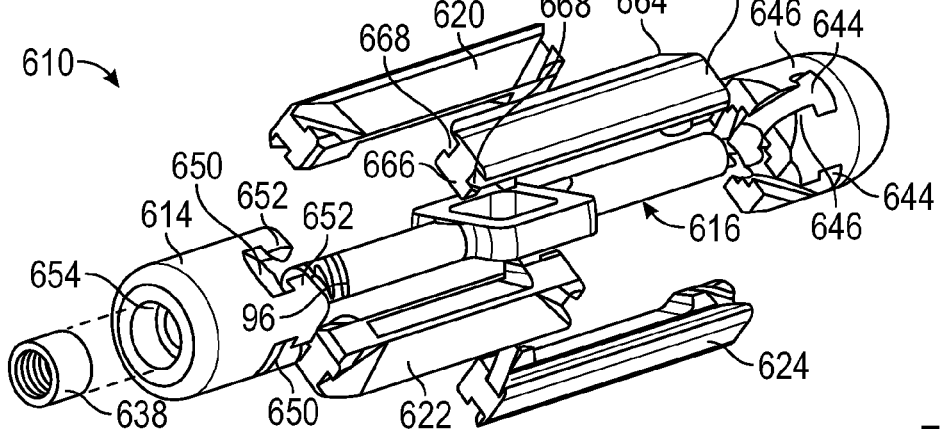
FIG. 66 is another perspective view of the implant of FIG. 59 according to an exemplary embodiment.
Figure 65:
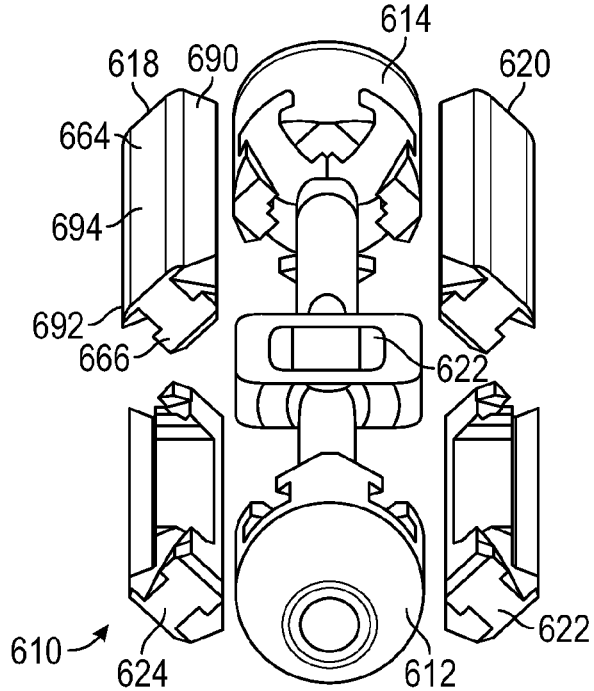
FIG. 65 is a perspective view of the implant of FIG. 59 according to an exemplary embodiment.

Referring to FIGS. 65-67, according to an exemplary embodiment, first portion 612 is fixedly coupled to control member 616, and second portion 614 is moveably coupled to control member 616. For example, in one embodiment, second portion 614 is slidable along at least a portion of control member 616 (e.g., by rotation of collar 638) such that the longitudinal distance between first and second portions 612, 614 is adjustable. Supports 618, 620, 622, 624 are coupled to first and second portions 612, 614 such that supports 618, 620, 622, 624 are moveable between expanded and collapsed positions by moving second portion 614 toward or away from first portion 612 along control member 616.

According to an exemplary embodiment shown in FIGS. 61-62, 65, and 67, supports 618, 620, 622, 624 and first and second portions 612, 614 have corresponding geometry that causes the longitudinal displacement of second portion 614 relative to first portion 612 to result in inward or outward radial movement of support 618, 620, 622, 624. For example, in one embodiment, as second portion 614 moves toward first portion 612 (e.g., as the distance between first and second portions 612, 614 decreases), supports 618, 620, 622, 624 move radially outward, and as second portion 614 moves away from first portion 612 (e.g., as the distance between first and second portions 612, 614 increases), supports 618, 620, 622, 624 move radially inward. In one embodiment, support 618 is located opposite from and moves in an opposite radial manner relative to support 622, and support 620 is located opposite from and moves in an opposite radial manner relative to support 624. Furthermore, support 618, 622 are generally perpendicularly arranged relative to supports 620, 624, and supports 618, 622 move in perpendicular directions relative to supports 620, 624.

According to one embodiment, supports 618, 620, 622, 624 have similar structures to each other and are moveably coupled to first and second portions 612, 614 in similar fashions. For example, referring to FIGS. 72-74, support 618 is a generally elongated member that extends at least partially between first and second portions 612, 614. In one embodiment, support 618 includes an outer surface 664, and may be configured such that all or a portion of outer surface 664 extends longitudinally beyond first portion 612 and/or second portion 614 when implant 610 is in the first or collapsed configuration.

Figure 74:
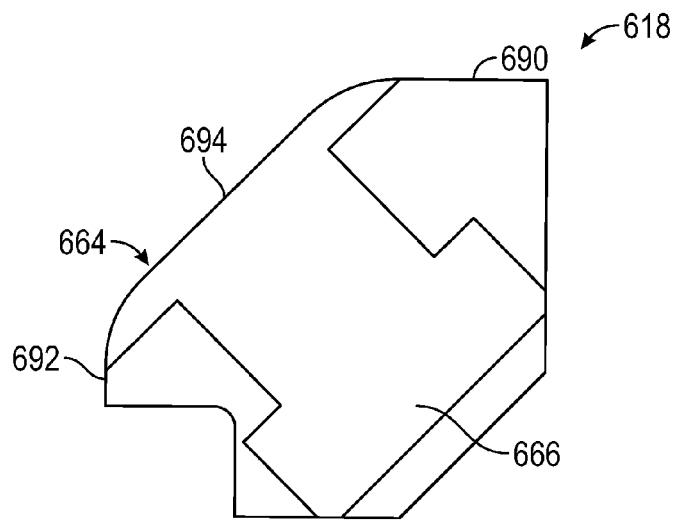
FIG. 74 is a front view of the support member of FIG. 72 according to an exemplary embodiment.
Figure 72:
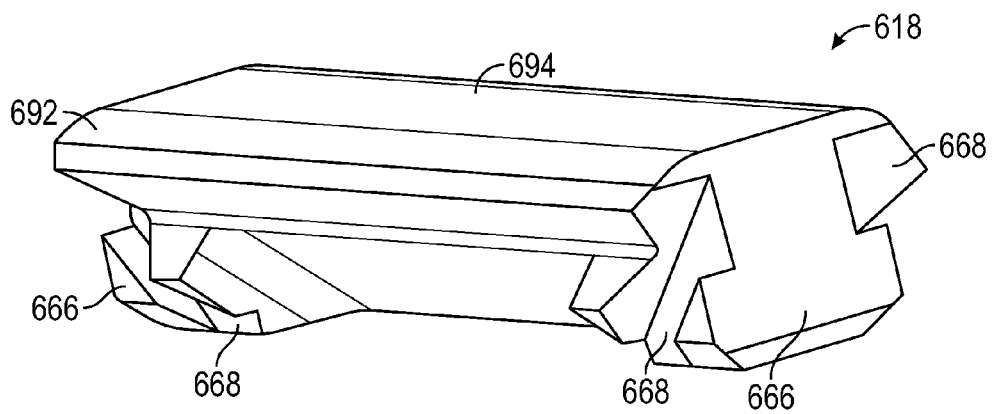
FIG. 72 is a perspective view of a support member of the implant of FIG. 59 according to an exemplary embodiment.
Figure 73:
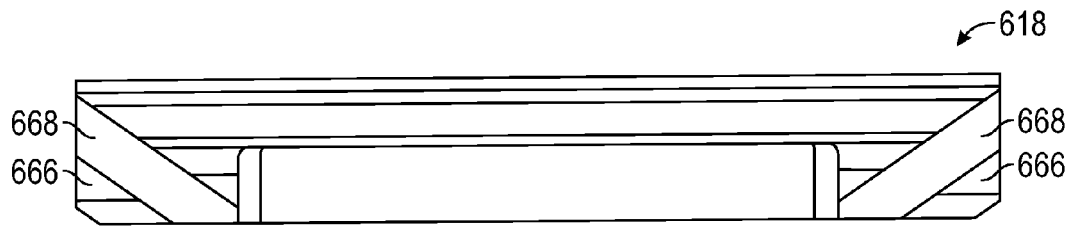
FIG. 73 is a side view of the support member of FIG. 72 according to an exemplary embodiment.
Figure 75:
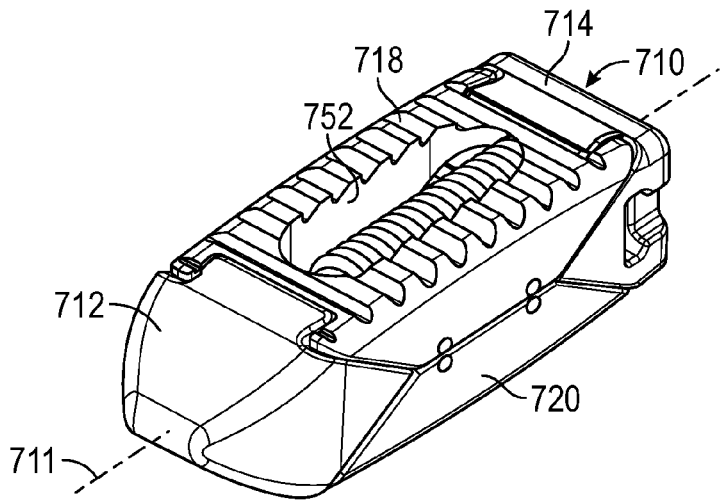
FIG. 75 is a perspective view of an expandable implant in a retracted configuration according to another exemplary embodiment.
Figure 77:
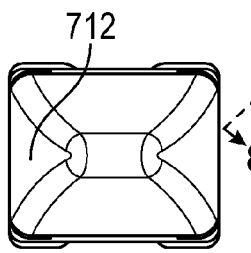
FIG. 77 is a front view of the expandable implant of FIG. 75 according to an exemplary embodiment.
Figure 76:
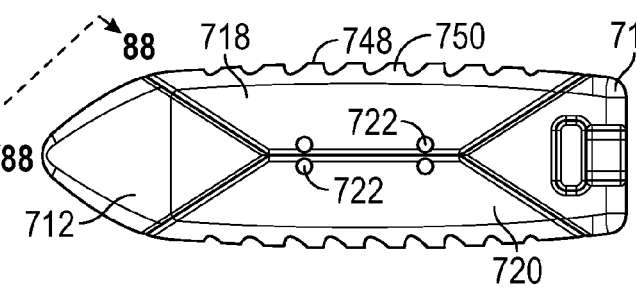
FIG. 76 is a side view of the expandable implant of FIG. 75 according to an exemplary embodiment.
Figure 78:
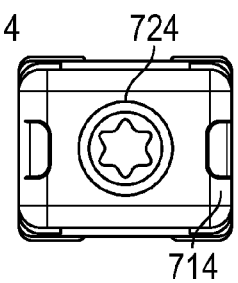
FIG. 78 is a rear view of the expandable implant of FIG. 75 according to an exemplary embodiment.
Figure 79:
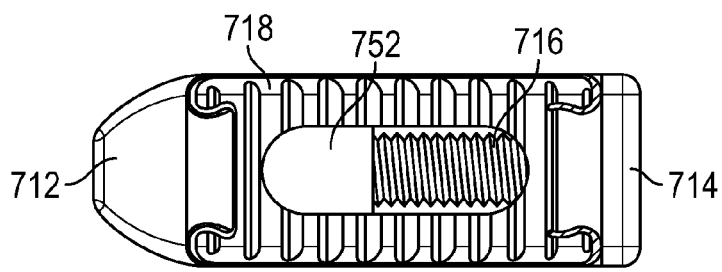
FIG. 79 is a top view of the expandable implant of FIG. 75 according to an exemplary embodiment.
Figure 80:
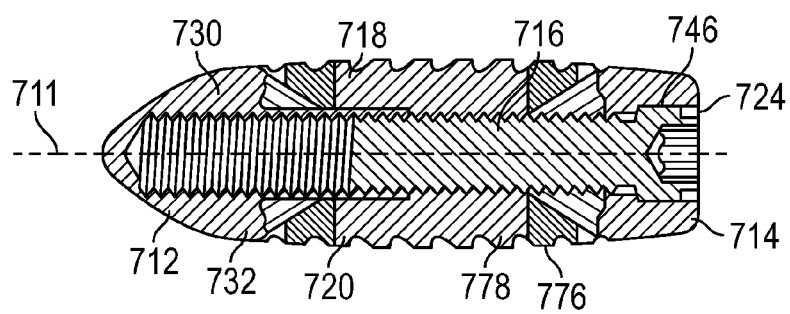
FIG. 80 is a cross-sectional view of the expandable implant of FIG. 75 according to an exemplary embodiment.
Figure 81:
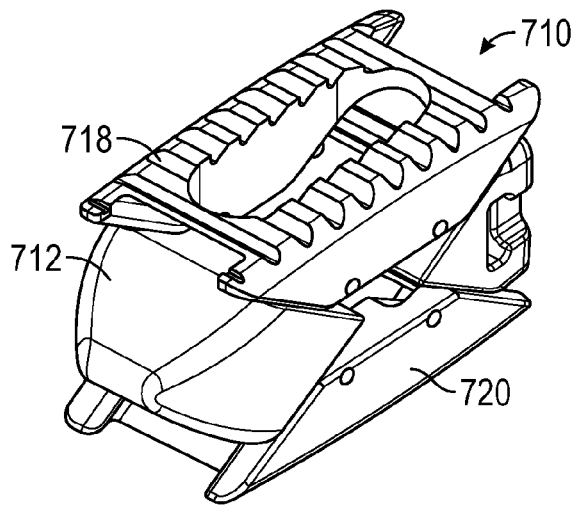
FIG. 81 is a perspective view of the expandable implant of FIG. 75 in an expanded configuration according to an exemplary embodiment.
Figure 83:
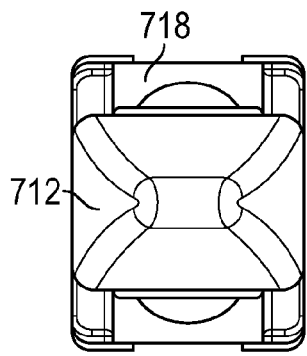
FIG. 83 is a front view of the expandable implant of FIG. 75 in an expanded configuration according to an exemplary embodiment.
Figure 82:
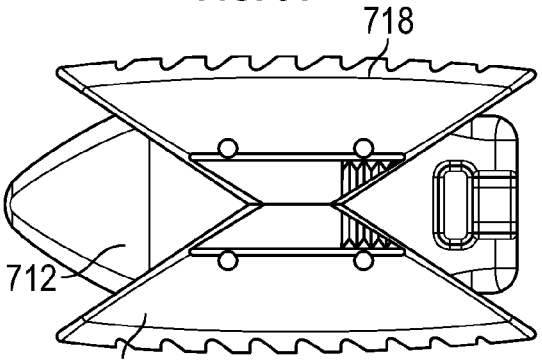
FIG. 82 is a side view of the expandable implant of FIG. 75 in an expanded configuration according to an exemplary embodiment.
Figure 84:
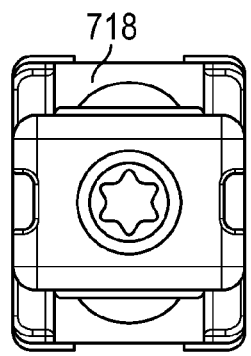
FIG. 84 is a rear view of the expandable implant of FIG. 75 in an expanded configuration according to an exemplary embodiment.
Figure 85:
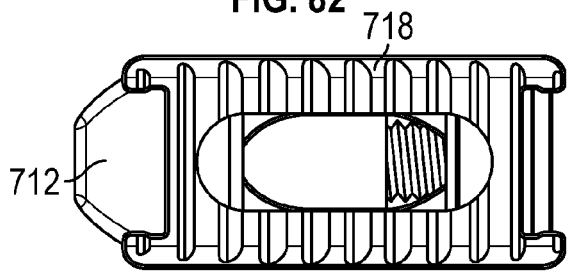
FIG. 85 is a top view of the expandable implant of FIG. 75 in an expanded configuration according to an exemplary embodiment.
Figure 86:
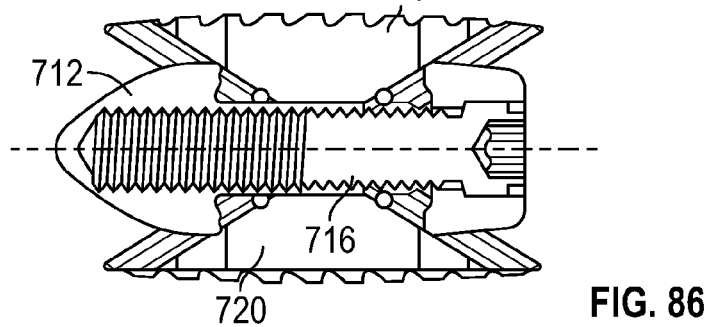
FIG. 86 is a cross-sectional view of the expandable implant of FIG. 75 in an expanded configuration according to an exemplary embodiment.

According to an exemplary embodiment shown in FIGS. 72-74, support 618 includes an outer surface 664, a portion 690 of which defines top 626 of implant 610 and a portion 692 of which defines first side 630 of implant 610. Portions 690, 692 are generally perpendicular relative to one another and are joined by a middle surface 694 (e.g., FIG. 74). In some embodiments, surface portions 690, 692 each extend from middle portion 694 at an obtuse angle (e.g., an angle of approximately 135 degrees), while in other embodiments the angular relationships between surface portions 690, 692, 694 may be of other angular values. As shown in the FIGURES, surface portions 690, 692, 694 are generally planar surfaces that extend in a parallel fashion relative to longitudinal axis 688. In other embodiments, surface portions 690, 692, 694 may be non-planar (e.g., curved, concave, convex, irregularly contoured, etc.) and/or be non-parallel relative to longitudinal axis 688. Furthermore, surface portions 690, 692, 694 may be smooth, textured, provided with ridges, teeth, projections (e.g., for gripping adjacent bone material), and the like.

Support 618 includes a guide portion 666 (e.g., a projection, etc.) provided at each end of support 618. Guide portion 666 may be generally T-shaped and may be formed by a pair of channels 668 that extend at an angle (e.g., 45 degrees, etc.) relative to longitudinal axis 688. While guide portion 666 is shown as having a general T-shape, according to various alternative embodiments, guide portion 666 may take any suitable shape. Guide portions 666 are slidably received within guide channels 644, 650 of first and second portions 612, 614, respectively, so as to adjustably couple support 618 to first and second portions 612, 614. According to one embodiment, guide portions 666 and guide channels 644, 650 include mating sliding surfaces that extend at an angle of approximately 45 degrees relative to longitudinal axis 688. According to various alternative embodiments, the mating sliding surfaces of guide portions 666 and guide channels 644, 650 may extend at other angles relative to longitudinal axis 688 (e.g., at angles of more or less than 45 degrees).

Supports 620, 622, 624 include similar features to support 618. For example, support 620 includes an outer surface 670, guide portions 672, and guide channels 674. Support 622 includes an outer surface 676, guide portions 678, and guide channels 680. Support 624 includes an outer surface 682, guide portions 684, and guide channels 686. Supports 620, 622, 624 are coupled to and move relative to first and second portions 612, 614 in the same manner as support 618. According to one embodiment, supports 618 and 622 are substantially identical in structure and are mirror images of supports 620, 624. In other embodiments, each support may have a different structure.

According to an exemplary embodiment, control member 616 is an elongated member that extends between first and second portions 612, 614. Control member 616 includes a cavity, or graft chamber 662 located generally at the midpoint of control member 616. Chamber 662 is configured to receive bone growth or other materials to facilitate growth of bone, etc. in and around implant 610. Chamber 662 is in one embodiment generally rectangular in shape, while in other embodiments, chamber 662 may take other shapes, including square, circular, oval, irregular shapes, etc. In some embodiments, control member 616 may be generally cylindrical in shape to either side of chamber 662, and one or both ends of control member 616 may be threaded to facilitate coupling of control member 616 to collar 638 and/or first portion 612.

Referring to FIGS. 59-61, in one embodiment, outer surfaces 664, 670 of supports 618, 620 and surfaces 676, 682 of supports 620, 622 are generally adjacent one another to form continuous top and bottom surfaces for implant 610 when implant 610 is in the first or collapsed configuration. To accommodate chamber 662, supports 618, 620, 622, 624 define side gaps, or spaces 634, 636 that are sized to accommodate chamber 662 and facilitate the introduction of bone growth or other material into the interior of chamber 662.

In use, implant 610 may initially be in the first or retracted configuration, as shown in FIGS. 59-61. Implant 610 may be inserted into a patient in a desired position (e.g., into or adjacent a vertebral body, etc.) using a suitable installation tool. Once in a desired position, implant 610 may be radially expanded to an expanded configuration, as shown in FIGS. 62-64. To expand/collapse implant 610, a tool (e.g., a screw driver, wrench, etc.) may be used to rotate collar 638 about control member 616 to move collar 638 and second portion 614 along control member 616 and adjust the longitudinal spacing between first and second portions 612, 614 (e.g., closer or further apart) and the radial expansion of supports 618, 620, 622, 624 (expansion and retraction).

In some embodiments, the angular relationships between the outer surfaces 664, 670, 676, 682 of supports 618, 620, 622, 624 remains constant as the supports are expanded/collapsed. In other embodiments, supports 618, 620, 622, 624 move linearly and radially outward, such that supports 618, 620, 622, 624 do not rotate relative to axis 688 when moving between the collapsed and expanded configurations.

In the expanded configuration, supports 618, 620, 622, 624 may be positioned so as to form a generally X-shaped support. This configuration may reduce the chance of the implant tipping over relative to other-shaped implants (e.g., circular or oval). Furthermore, as shown in FIG. 64, both the height and width of implant 610 are increased during expansion of implant 610, providing a benefit over many conventional expandable implants that may expand only in height. In other embodiments, supports 618, 620, 622, 624 may form other shapes in the expanded configuration. Furthermore, while the FIGURES generally illustrate implant 610 in either a fully collapsed or fully expanded configuration, it should be understood that implant 610, through rotation of collar 638 or another suitable adjustment mechanism, may be expanded to any intermediate level of expansion. Further yet, in some embodiments, implant 610 may be expandable to approximately double a height and width of implant 610.

According to various exemplary embodiments, the components of implant 610 may be made of any suitable material(s), including a variety of metals, plastics, composites, or other suitable bio-compatible materials. In some embodiments, one or more components of implant 610 may be made of the same material, while in other embodiments, different materials may be used for different components of implant 610.

Referring now to FIGS. 75-88, an expandable implant 710 is shown according to an exemplary embodiment. Implant 710 is usable, for example, between and/or within vertebral bodies of the spine, and may share many of the features of the other inter/intra-body implants discussed elsewhere herein. It should be understood that implant 710 may in some embodiments be usable in other portions of the body in addition to the spine, and all such applications are to be understood to be within the scope of the present disclosure.

According to an exemplary embodiment, implant 710 includes a first, or front portion 712, a second, or rear portion 714, and a third, intermediate, or control member or portion 716, which collectively form a body assembly that extends along a longitudinal axis 711 of implant 710. A first, or upper support 718 (e.g., an upper plate or support member, etc.) and a second, lower support 720 (e.g., a lower plate or support member), are coupled to the body assembly and extend generally between front and rear portions 712, 714. According to an exemplary embodiment, first and second supports 718, 720 define a height of implant 710 extending between outer or top surface 748 of first support 718 and outer or lower surface 776 of second support 720.

In one embodiment, front portion 712 includes a rounded, or bull nose portion intended to facilitate insertion of implant 710 into a patient. Front portion 712 also includes ramped surfaces 726, 728 and projections 730, 732 that facilitate controlled sliding movement between front portion 712 and first and second supports 718, 720. An aperture 734 may be threaded to receive control member 716 to provide an adjustable control mechanism for implant 710.

Figure 87:
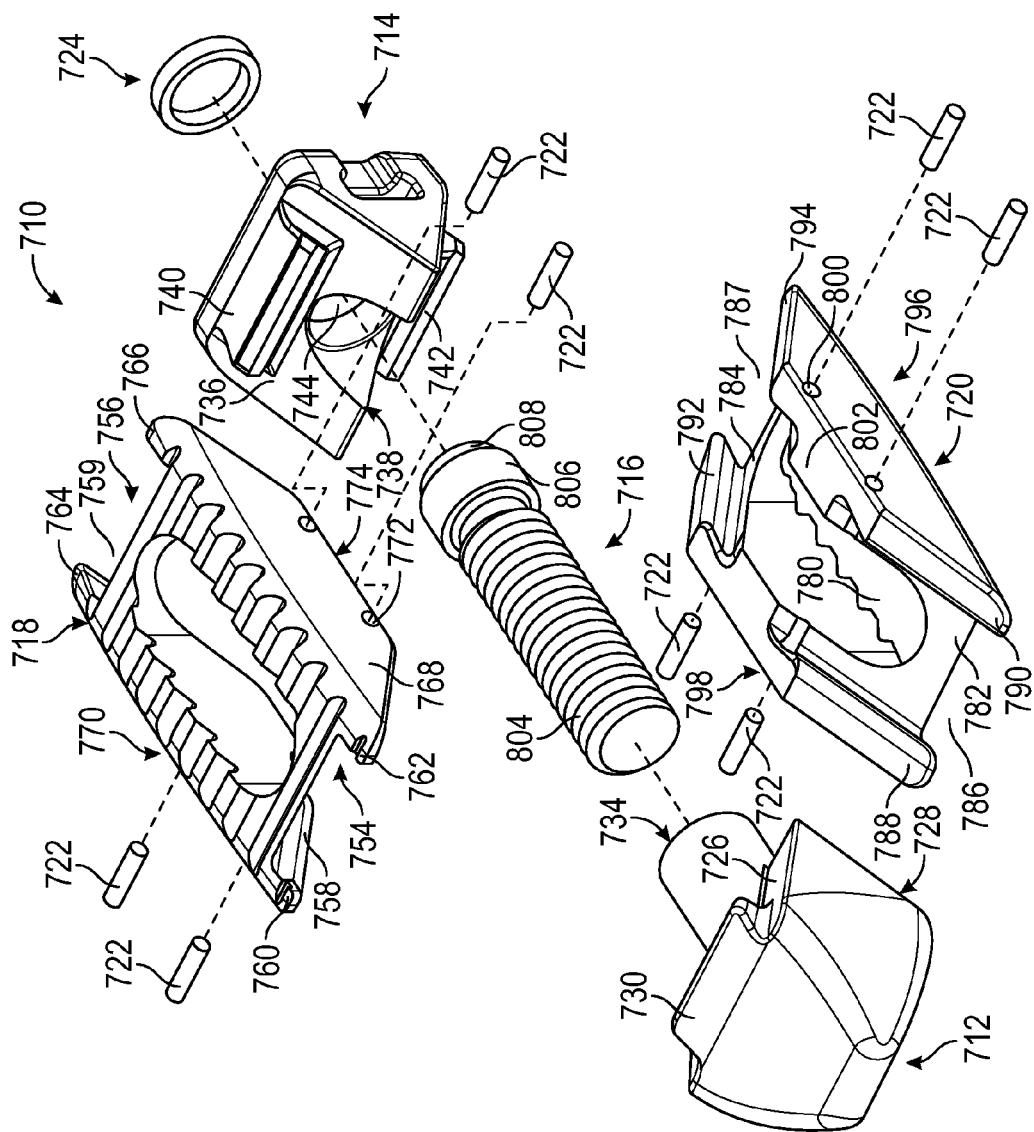
FIG. 87 is an exploded perspective view of the expandable implant of FIG. 75 according to an exemplary embodiment.
Figure 88:
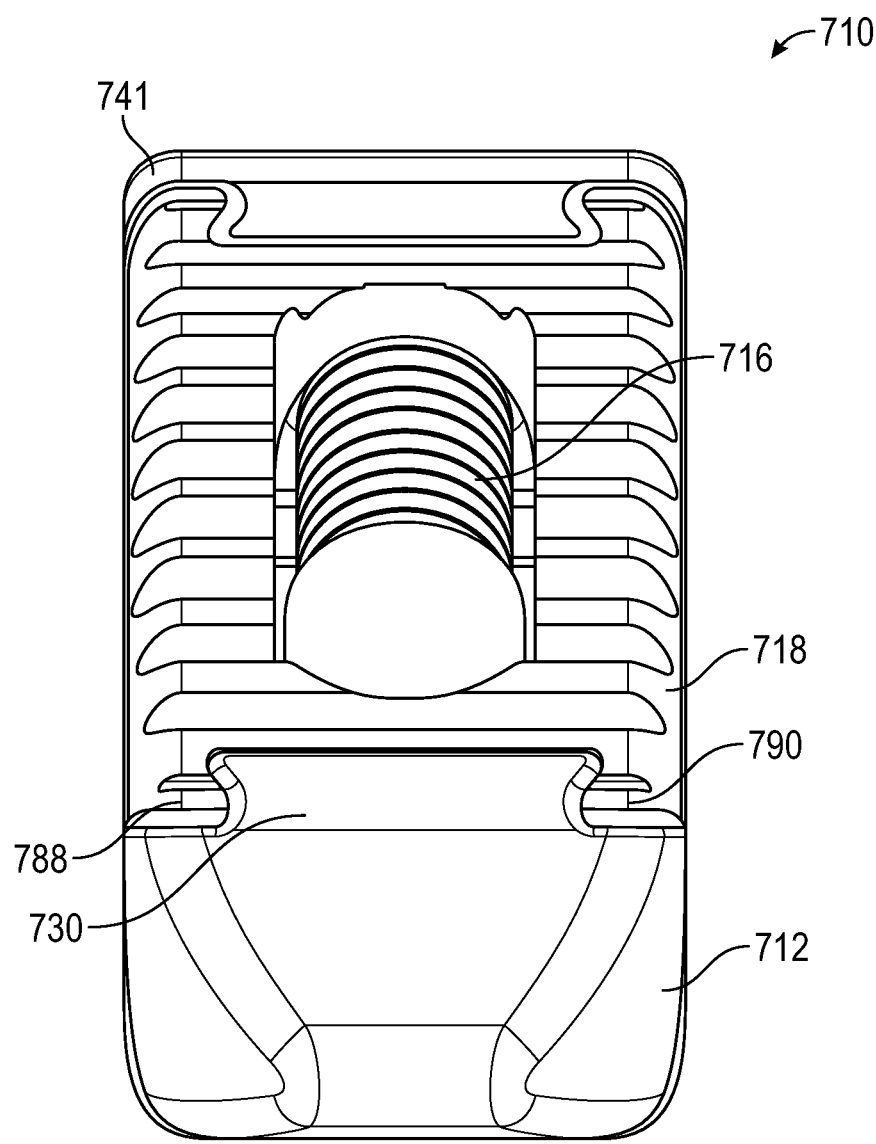
FIG. 88 is a perspective view of the expandable implant of FIG. 75 taken along line A-A shown in FIG. 76 according to an exemplary embodiment.

Referring to FIG. 87, ramped surface 726 extends at an angle relative to axis 711, and projection 730 extends upward relative to ramped surface 726. Ramped surface 726 is a generally flat surface configured to engage a correspondingly ramped surface (surface 754) on first support 718. Projection 730 extends laterally across front portion 712. In some embodiments, projection 730 may have a dovetail shape, while in other embodiments, projection 730 may take other shapes, including having an undercut portion etc. The dovetail shape provides a relatively larger top portion and an undercut lower portion such that front portion 712 and first support 718 can slide relative to one another, but the parts cannot be separated, for example, by merely lifting first support 718 away from front portion 712 (e.g., in an upward direction generally perpendicular to axis 711).

Ramped surface 728 and projection 732 share similar features to ramped surface 726 and projection 730, except that ramped surface 728 and projection 732 interface with corresponding surfaces on second support 720, rather than first support 718. It should be noted that ramped surfaces 726, 728 may be inclined relative to axis 711 to provide any desirable adjustment features, as changing the incline of the ramped surfaces will change the rate at which the first and second support members move up/down.

Referring further to FIG. 87, according to an exemplary embodiment, rear portion 714 includes ramped surfaces 736, 738, projections 740, 742, an aperture, or through-hole 744, and a counterbore 746. Rear portion 714 may define a generally flat rearward-most surface being generally rectangular in shape. In other embodiments, the shape of rear portion 714 may be varied to suit a particular application.

Ramped surface 736 extends at an angle relative to axis 711, and projection 740 extends upward relative to ramped surface 736. Ramped surface 736 is a generally flat surface configured to engage a correspondingly ramped surface (surface 756) on first support 718. Projection 740 extends laterally across rear portion 714. In some embodiments, projection 740 may have a dovetail shape (see, e.g., FIG. 88), while in other embodiments, projection 740 may take other shapes, including having an undercut portion etc. The dovetail shape provides a relatively larger top portion and an undercut lower portion such that rear portion 714 and first support 718 can slide relative to one another, but the parts cannot be separated, for example, by merely lifting first support 718 away from rear portion 714 (e.g., in an upward direction generally perpendicular to axis 711).

Ramped surface 738 and projection 742 share similar features to ramped surface 736 and projection 740, except that ramped surface 738 and projection 742 interface with corresponding surfaces on second support 720, rather than first support 718. It should be noted that ramped surfaces 736, 738 may be inclined relative to axis 711 to provide any desirable adjustment features, as changing the incline of the ramped surfaces will change the rate at which the first and second support members move up/down.

According to an exemplary embodiment, first and second supports 718, 720 are configured to be moveable relative to the body assembly (e.g., front and rear portions 712, 714 and control portion 716) such that implant 710 is reconfigurable between a first configuration (e.g., a retracted, collapsed, or minimal configuration), as shown in FIGS. 75-80, and a second configuration (e.g., an expanded or maximum configuration), as shown in FIGS. 81-86 and any intermediate position therebetween. Control member 716 is rotatable and threadingly received by front portion 712 such that rotation of control member 716 in a first (e.g., clockwise) direction causes front and rear portions 712, 714 to move toward each other, thereby causing first and second supports 718, 720 to move outward toward the expanded configuration. Conversely, rotation of control member 716 in a second (e.g., counter-clockwise) direction causes front and rear portions 712, 714 to move away from each other, thereby causing first and second supports 718, 720 to move inward toward the collapsed configuration. It should be noted that in use, control member 716 may be adjusted so as to maintain first and second supports 718, 720 in a fully collapsed configuration, a fully expanded configuration, or any desired configuration or intermediate position therebetween.

First and second supports 718, 720 and front and rear portions 712, 714 have corresponding geometric features (e.g., correspondingly ramped surfaces) such that displacement of front portion 712 relative to rear portion 714 along axis 711 causes relative planar and/or linear displacement of first and second supports 718, 720. As discussed above, the geometric features of the various components may be varied to provide for varying adjustment features for first and second supports 718, 720.

In one embodiment, first and second supports 718, 720 are generally similar in structure. Referring to FIG. 87, first support 718 includes outer, or top surface 748, ramped surfaces 754, 756, channels 758, 759, and two pairs of opposing projections—projections 760, 762, and projections 764, 766, First support 718 further includes sidewalls 768, 770, pin or retaining member apertures 772, and inner, or bottom surface 774. Top surface 748 includes a number of ridges, or projections 750, intended to provide a gripping surface for adjacent vertebrae, and a bone graft cavity, or window 752 intended to provide a space to receive bone graft material.

In use, control member 716 extends through through-hole 744 in rear portion 714 and into front portion 712. Head portion 806 of control member 716 seats in counterbore 746 of rear portion 714, and threaded portion 804 threadingly engages aperture 734 of front portion 712. Head portion 806 may include an annular recess configured such that a collar 724 can be positioned (e.g., press-fit, welded, etc.) into counterbore 746 rearward of head portion 806 to retain control member 716 in place. As a user rotates control member 716, front portion 712 and rear portion 714 move toward/away from each other (depending on the direction of rotation), and first and second supports 718, 720 in turn move away from/toward each other.

As shown in FIG. 87, opposing projections 760, 762 on first support 718 form a recess, or channel 758. In one embodiment, channel 758 has a dovetail shape corresponding in shape to projection 730 on front portion 712. Likewise, projections 764, 766 in first support 718 form channel 759 having a dovetail shape similar in shape to projection 740 on rear portion 714. Projections 730, 740 slide within channels 758, 759 as first support 718 moves up/down. Retaining members or pins 722 extend through first and second supports 718, 720 and act to limit the range of movement of first and second supports 718, 720 relative to front and rear portions 712, 714, and prevent first and second supports 718, 720 from being completely removed from front and rear portions 712, 714.

Second support 720 is similar to first support 718 and includes outer, or bottom surface 776, ramped surfaces 782, 784, channels 786, 787, and two pairs of opposing projections—projections 788, 790, and projections 792, 794, Second support 720 further includes sidewalls 796, 798, pin or retaining member apertures 780, and inner, or top surface 802. Bottom surface 776 includes a number of ridges, or projections 778, intended to provide a gripping surface for adjacent vertebrae, and a bone graft cavity, or window 780 intended to provide a space to receive bone graft material. In one embodiment, the components of second support 720 are similar in structure and function to the corresponding components of first support 718. In other embodiments, the components of second support 720 may provide additional and/or different structural and/or functional features relative to the corresponding components of first support 718.

It should be noted that implant 710 may share various features with the other implants described herein, and be made of the same, similar, or different materials. For example, various components of implant 710 may be made of metal, plastic, composites, or other suitable bio-compatible materials. Further, implant 710 may be usable in connection with the spine or other parts of the body.

Figure 89:
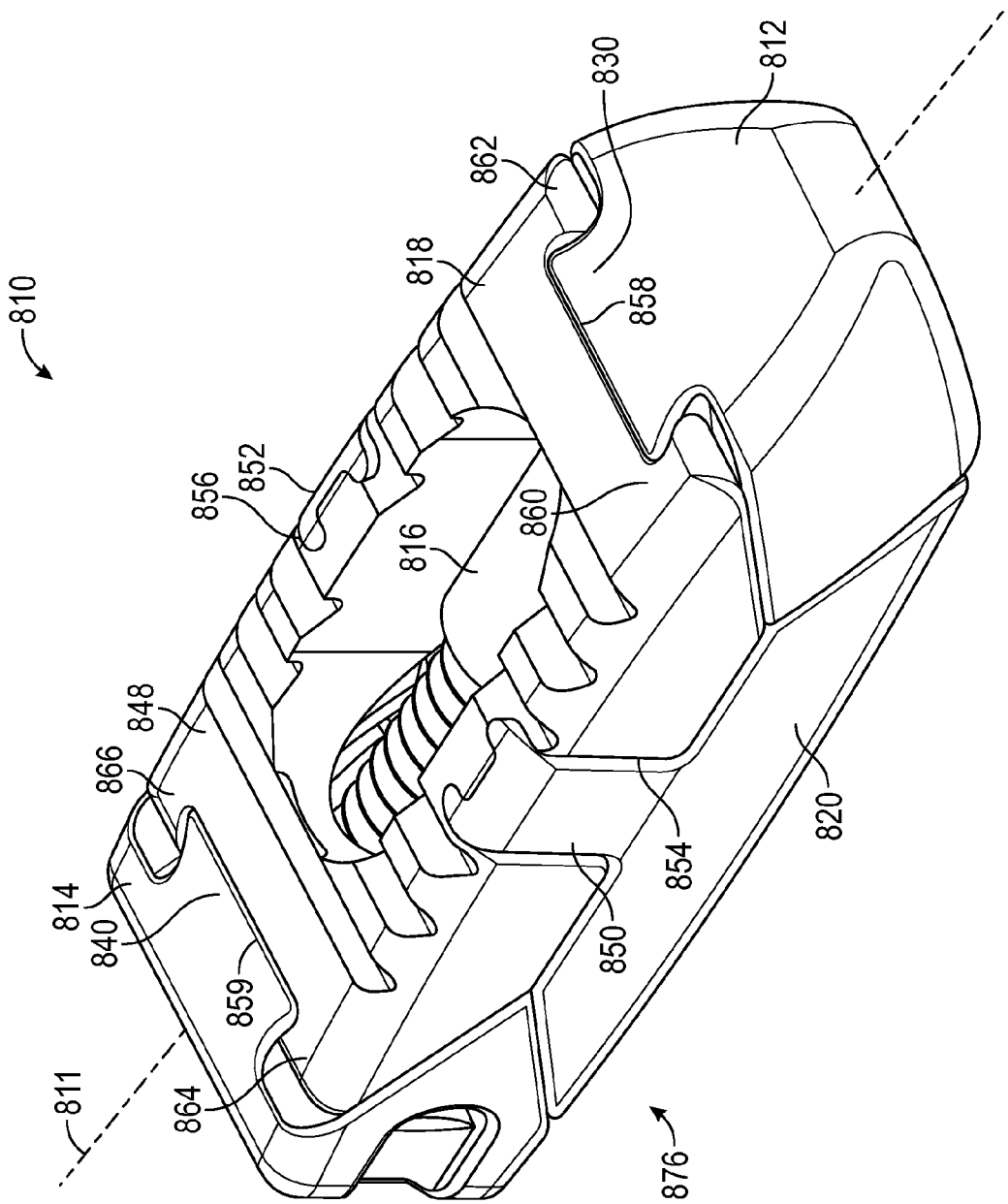
FIG. 89 is a perspective view of an expandable implant in a contracted configuration according to another exemplary embodiment.

Referring now to FIG. 89, an expandable implant 810 is shown according to an exemplary embodiment. Implant 810 is usable, for example, between and/or within vertebral bodies of the spine, and may share many of the features of the other inter/intra-body implants discussed elsewhere herein. It should be understood that implant 810 may in some embodiments be usable in other portions of the body in addition to the spine, and all such applications are to be understood to be within the scope of the present disclosure. Implant 810 is generally similar to implant 710 in structure and function except with respect to the additional alignment features discussed below.

According to an exemplary embodiment, implant 810 includes a first, or front portion 812, a second, or rear portion 814, and a third, intermediate, or control member or portion 816, which collectively form a body assembly that extends along a longitudinal axis 811 of implant 810. A first, or upper support 818 (e.g., an upper plate or support member, etc.) and a second, lower support 820 (e.g., a lower plate or support member), are coupled to the body assembly and may extend generally between front and rear portions 812, 814. According to an exemplary embodiment, first and second supports 818, 820 define a height of implant 810 extending between outer or top surface 848 of first support 818 and outer or lower surface 876 of second support 820.

In one embodiment, front portion 812 includes a rounded, or bull nose portion intended to facilitate insertion of implant 810 into a patient. Front portion 812 also includes ramped surfaces and projections (e.g., similar to ramped surfaces 726, 728 and projections 730, 732) that facilitate controlled sliding movement between front portion 812 and first and second supports 818, 820. An aperture may be threaded to receive control member 816 to provide an adjustable control mechanism for implant 810.

As shown in FIG. 89, the ramped surfaces extend at an angle relative to axis 811, and the projections extend upward/downward relative to the ramped surfaces. The ramped surfaces are generally flat surfaces configured to engage a correspondingly ramped surface on first support 818. The projections extend laterally across front portion 812. In some embodiments, the projections may have a dovetail shape, while in other embodiments, the projections may take other shapes, including having an undercut portion, etc. The dovetail shape provides a relatively larger top portion and an undercut lower portion such that front portion 812 and first support 818 can slide relative to one another, but the parts cannot be separated, for example, by merely lifting first support 818 away from front portion 812 (e.g., in an upward direction generally perpendicular to axis 811). It should be noted that similar to implant 710, implant 810 includes front and rear, upper and lower ramped surfaces and projections configured to provide the interface between front and rear portions 812, 814 and first and second supports 818, 820.

As with implant 710, according to an exemplary embodiment, first and second supports 818, 820 and front and rear portions 812, 814 have corresponding geometric features (e.g., correspondingly ramped surfaces) such that displacement of front portion 812 relative to rear portion 814 along axis 811 causes relative planar and/or linear displacement of first and second supports 818, 820. As discussed above, the geometric features of the various components may be varied to provide for varying adjustment features for first and second supports 818, 820.

In use, control member 816 extends through a through-hole in rear portion 814 and into front portion 812. The head portion of control member 816 seats in a counterbore of rear portion 814, and the threaded portion threadingly engages an aperture of front portion 812. The head portion may include an annular recess (similar to head portion 806 of implant 710) configured such that a collar can be positioned (e.g., press-fit, welded, etc.) into the counterbore rearward of the head portion to retain control member 816 in place. As a user rotates control member 816, front portion 812 and rear portion 814 move toward/away from each other (depending on the direction of rotation), and first and second supports 818, 820 in turn move away from/toward each other.

Opposing projections 860, 862 on first support 818 form a recess, or channel 858. In one embodiment, channel 858 has a dovetail shape corresponding in shape to projection 830 on front portion 812. Likewise, projections 864, 866 in first support 818 form channel 859 having a dovetail shape similar in shape to projection 840 on rear portion 814. Projections 830, 840 slide within channels 858, 859 as first support 818 moves up/down. In some embodiments, retaining members or pins (e.g., similar to pins 722) extend through first and second supports 818, 820 and act to limit the range of movement of first and second supports 818, 820 relative to front and rear portions 812, 814, and prevent first and second supports 818, 820 from being completely removed from front and rear portions 812, 814. Second support 820 includes similar features such as an outer, or bottom surface, ramped surfaces, channels, and two pairs of opposing projections.

In addition to including various features of implant 710, implant 810 further includes an alignment feature intended to maintain alignment between first and second supports 818, 820 during use. In one embodiment, second support 820 includes one or more alignment members 850, 852 (e.g., extensions, projections, etc.) that extend generally upward as shown in FIG. 89 (e.g., in a direction generally perpendicular to axis 811). Members 850, 852 are received in recesses 854, 856 (e.g., channels, grooves, slots, etc.), respectively, formed in first support 818. Members 850, 852 and recesses 854, 856 have corresponding geometric features to ensure a snug fit between components. For example, as shown in FIG. 89, members 850, 852 are generally U-shaped in cross-section, and recesses 854, 856 is shaped to receive the U-shaped members. The alignment features prevent relative "rocking" of the supports, and in some embodiments serve to maintain a generally parallel relationship between the supports. In some embodiments, spaces or gaps may be provided between members 850, 852 and recesses 854, 856 to enable a predetermined amount of angular offset between the supports.

In one embodiment members 850, 852 are formed so as to be generally flush with the exterior surface of first support 818 (e.g., along a side or top surface). In other embodiments, members 850 may be recessed from, or alternatively protrude beyond, the exterior surface of first support 818. Further, while FIG. 89 shows two alignment members 850, 852, in various alternative embodiments fewer or more alignment members and/or recesses may be utilized (e.g., 1, 3, 4, etc.). Further yet, members 850, 852 may be integrally formed with, or removably coupled to, a remainder portion of second support 820. In further embodiments, the relative positions of alignment members 850, 852 and recesses 854, 856 are reversed (e.g., such that members 850, 852 are provided on first support 818 and recesses 854, 856 are provided on second support 820). Other variations in the size, number, and placement of members 850, 852 and recesses 854, 856 may be made according to various embodiments.

It should be noted that implant 810 may share various features with the other implants described herein, and be made of the same, similar, or different materials. For example, various components of implant 810 may be made of metal, plastic, composites, or other suitable bio-compatible materials. Further, implant 810 may be usable in connection with the spine or other parts of the body.

Figure 90:
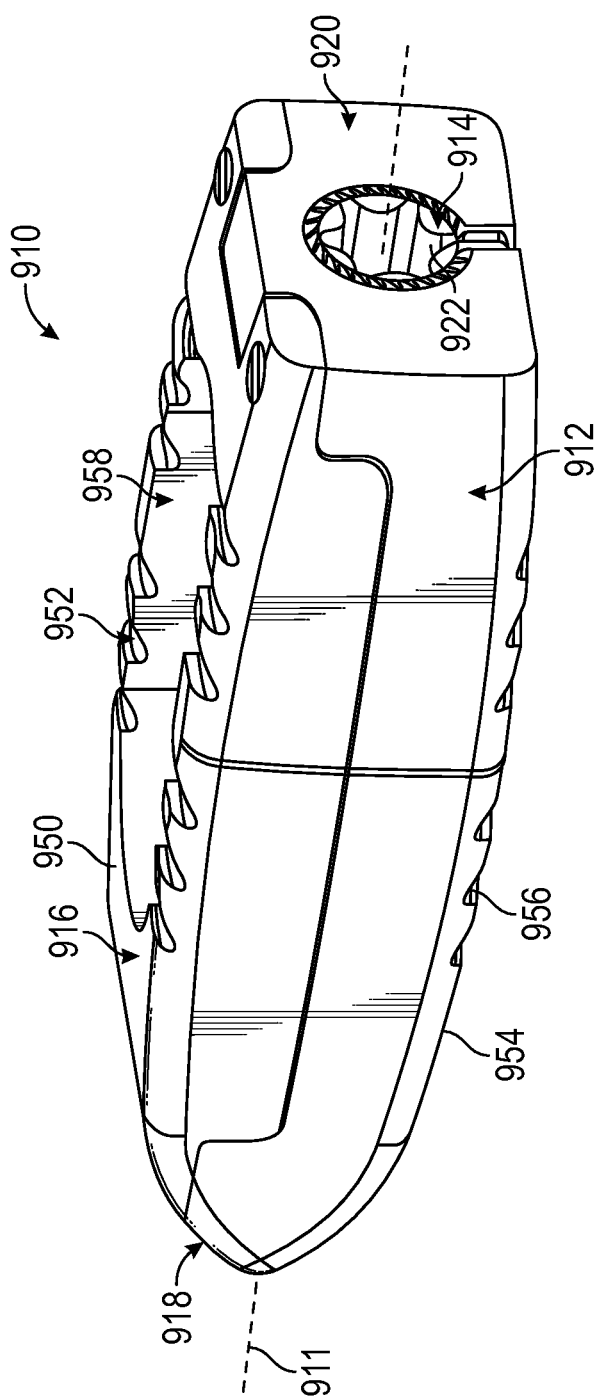
FIG. 90 is a perspective view of an expandable implant in a contracted configuration according to another exemplary embodiment.
Figure 91:
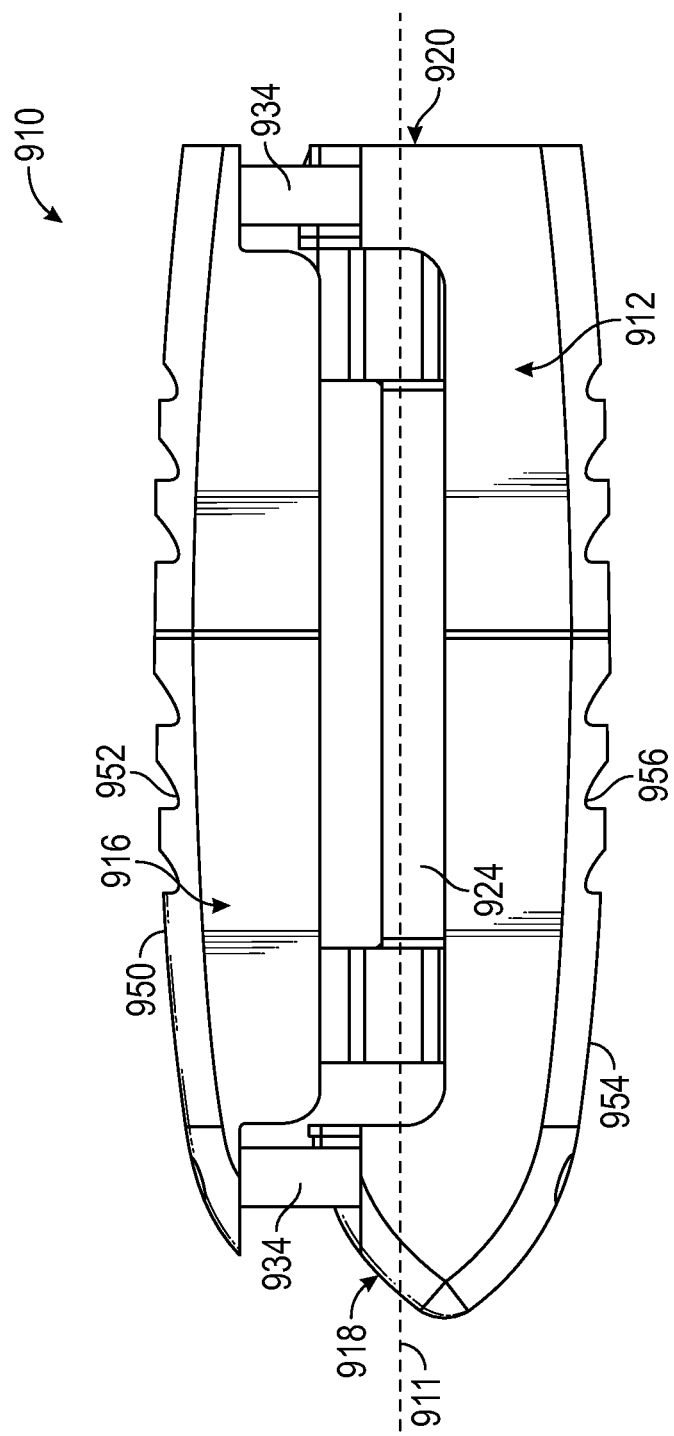
FIG. 91 is a side view of the expandable implant of FIG. 90 in an expanded configuration according to an exemplary embodiment.
Figure 92:
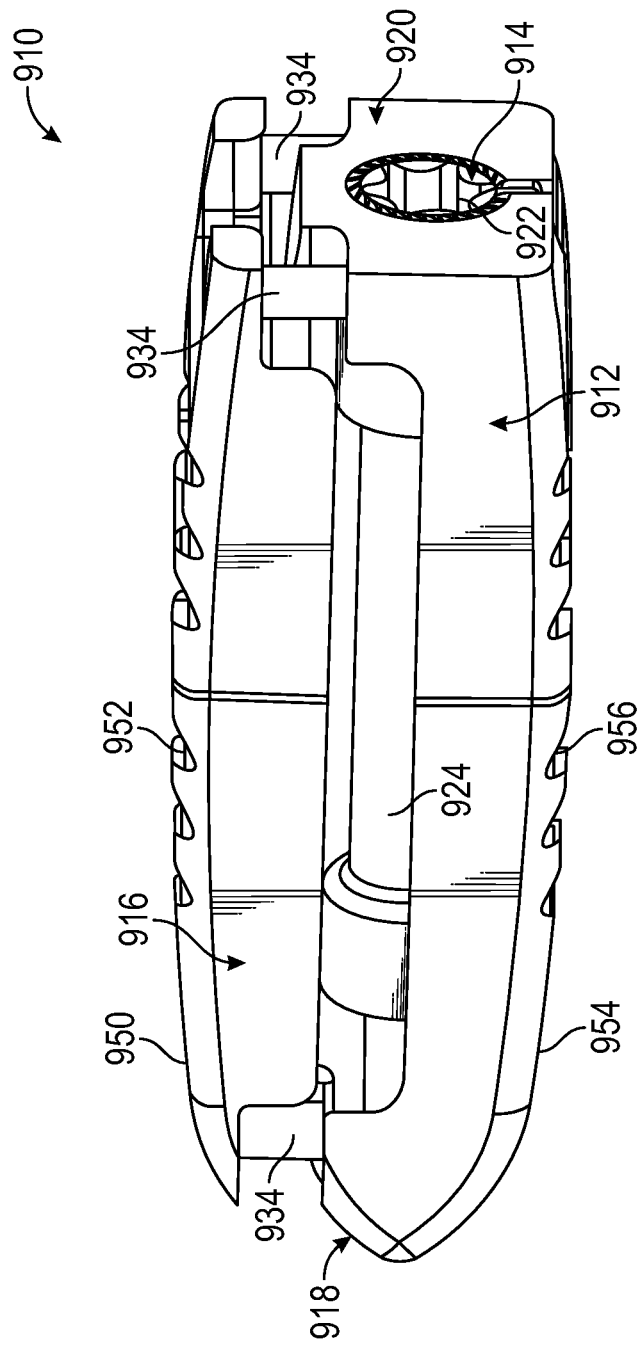
FIG. 92 is a perspective view of the expandable implant of FIG. 90 in an expanded configuration according to an exemplary embodiment.

In various embodiments, the implants shown in FIGS. 59-73, 74-88, and 89 share various common features. For example, the control member or screw (e.g., 616, 716, 816) is contained within the device, such that neither end of the control member or screw protrudes past the end members (e.g., 612, 614; 712, 714; 812, 814). For example, as shown in FIG. 87, the control member 716 may be received by or through rear portion 714 in a counterbore and held captive by collar or ring 724, such that control member 716 is free to rotate within rear portion 714, but does not threadingly engage rear portion. As such, rear portion 714 remains fixed relative to control member 716 as control member 716 is rotated. Control member 716 threadingly engages a threaded aperture 734 defined by a boss extending rearward from front portion 712, such that as control member 716 rotates, front portion 712 moves relative to control member 716 (e.g., control member 716 moves into or out of the threaded boss of front portion 712). As such, control member 716 is contained entirely within the periphery of front and rear portions 712, 714. The control member may in some embodiments be configured to be flush with the outer sides of front and rear portions 712, 714. In other embodiments, the control member is recessed within front and/or rear portions 712, 714. For example, as shown in FIG. 87, front portion 712 has a solid, bull-nose configuration such that control member 716 is concealed therein. In various embodiments, the implants include grooves that may help secure the implant in the body of a patient, by providing spaces for structures in the body of a patient to engage the grooves (see, e.g., grooves 952, 956 shown in FIG. 90, etc.).

Referring now to FIGS. 90-98, an expandable implant 910 (e.g., an interbody device, an intrabody device, etc.) is shown according to an exemplary embodiment. Implant 910 is usable, for example, between and/or within vertebral bodies of the spine, and may share many of the features of the other inter/intra-body implants discussed elsewhere herein. However, it should be understood that implant 910 may have other uses in other portions of a patient's body in addition to the spine (e.g., inside or around bone, such as a femur, as a cement restrictor, etc.). All such applications are understood to be within the scope of the present disclosure. While various embodiments disclosed herein use relative terms for indicating relative positions of components (e.g., proximal, distal, etc.) these terms are illustrative and not intended to limit the scope of the present disclosure.

According to an exemplary embodiment, implant 910 includes a body assembly 912 and a top member 916. Manipulation of components of implant 910 allows for top member 916 to be expanded (e.g., translated away from body assembly 912) or contracted (e.g., translated towards body assembly 912). Body assembly 912 may be provided as an integral (e.g., molded in one piece) body traversing from a proximal end 918 to a distal end 920 of implant 910. Similar to various implants disclosed herein, including implant 810, proximal end 918 may include a bull nose shape facilitating insertion of implant 910 into a patient during surgery. At distal end 920, a gap 914 allows for access to an interior of implant 910, and particularly to a receiver 922. Implant 910 may be implanted in various orientations, such that top member 916 is not necessarily above or below other components of implant 910 relative to a specific frame of reference.

Figure 94:
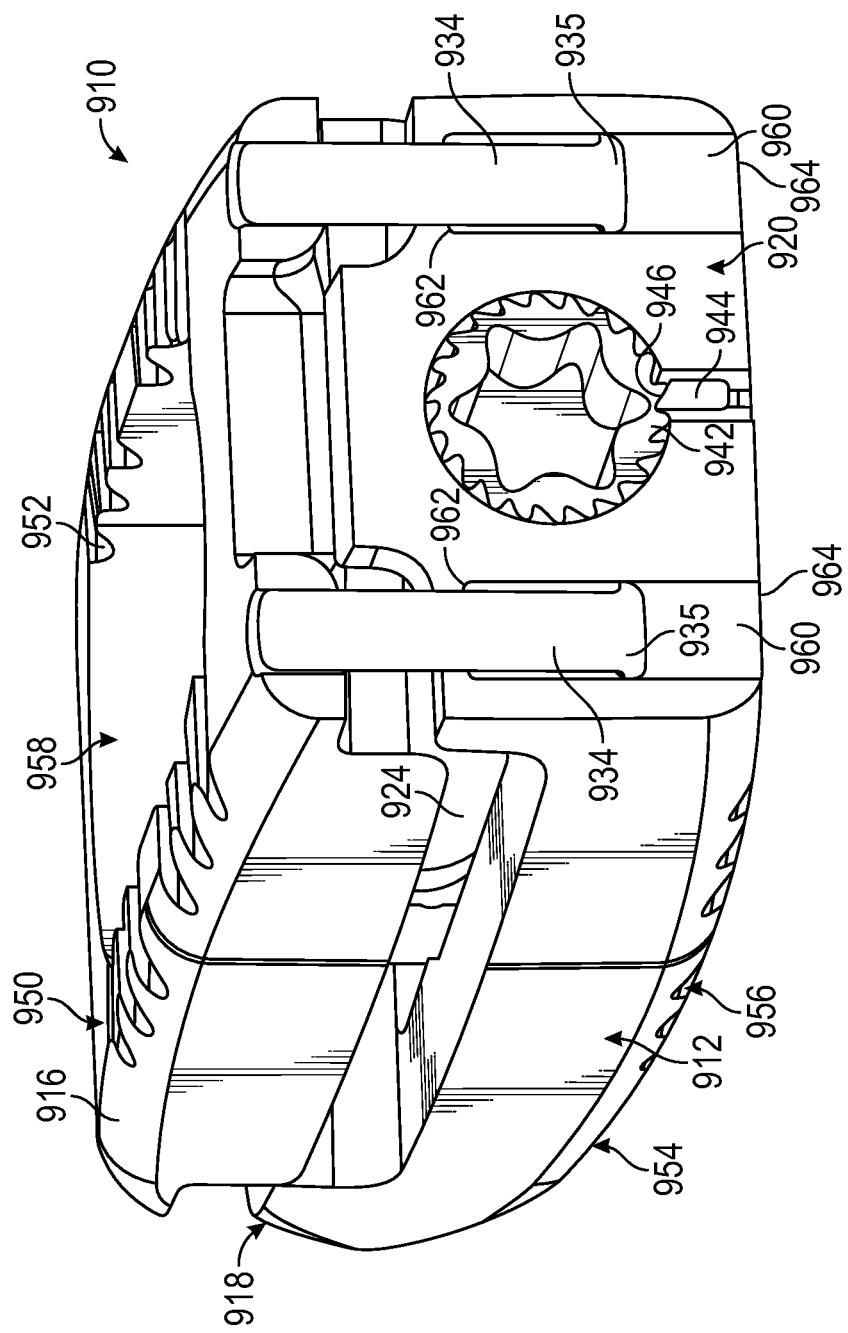
FIG. 94 is another perspective view of the expandable implant of FIG. 90 in an expanded configuration according to an exemplary embodiment.

Referring further to FIGS. 94-98, implant 910 includes top member 916, shaft 924, body assembly 912, and pins 934. Pins 934 pass through body assembly 912 and top member 916, helping to fix the orientation of top member 916 relative to body assembly 912. As shown in FIG. 94, pins 934 may include pin bases 935 having an outer radius that allows pins 934 to slide within channels 960 of body assembly 912. Channels 960 include minor mouths 962 and major mouths 964. Minor mouths 962 have an outer radius that is less than the outer radius of pin bases 935, such that when pin bases 935 contact minor mouths 962 due to sliding of pins 934, minor mouths 962 prevent pins 934 from sliding further, and thus prevent top member 916 from being translated further away from body assembly 912.

Figure 93:
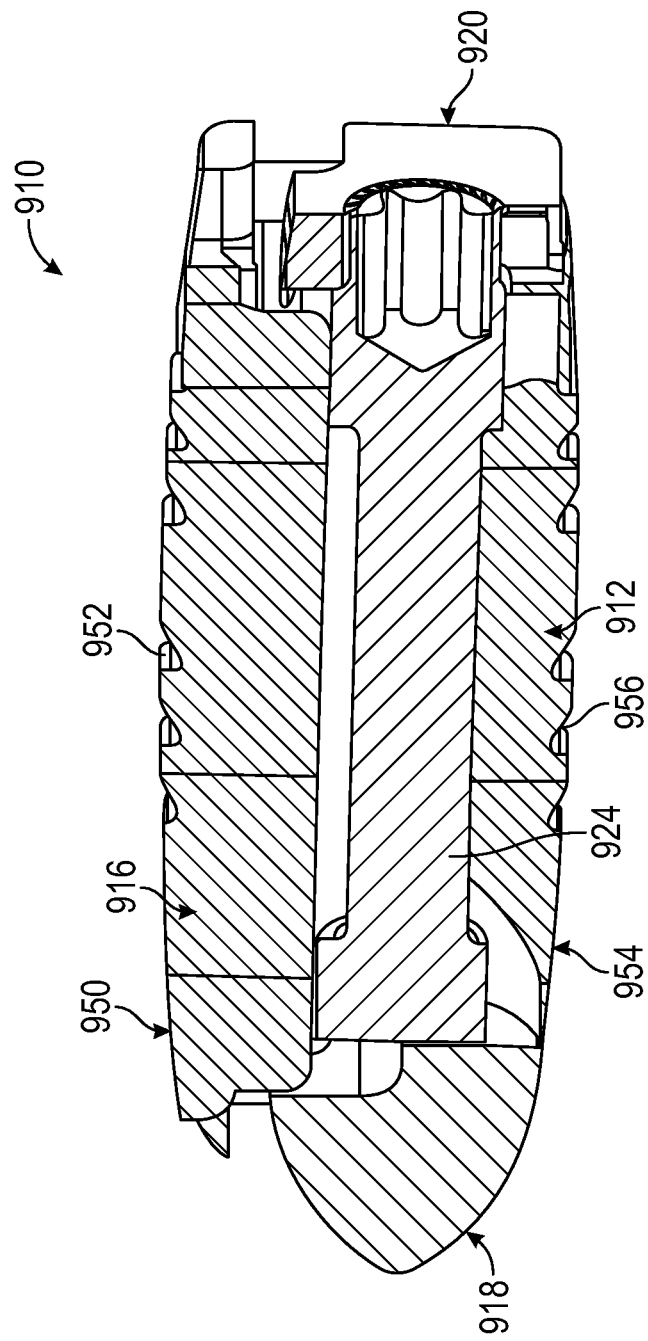
FIG. 93 is a sectional view of the expandable implant of FIG. 90 in an expanded configuration according to an exemplary embodiment.
Figure 95:
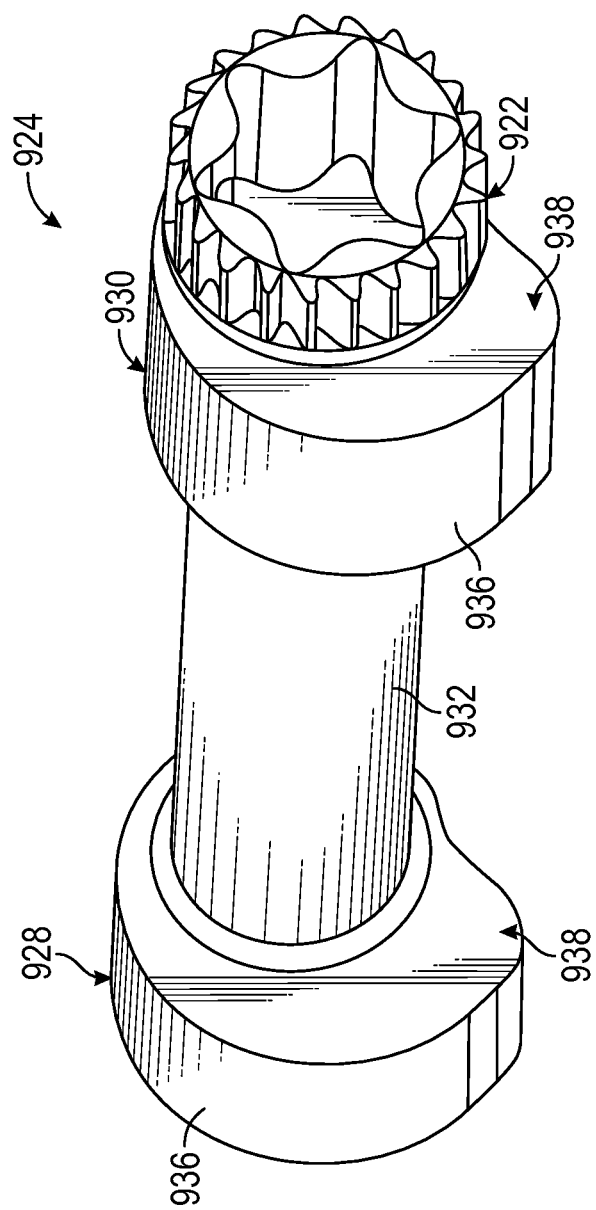
FIG. 95 is a perspective view of a shaft configured for use with the expandable implant of FIG. 90 according to an exemplary embodiment.
Figure 96:
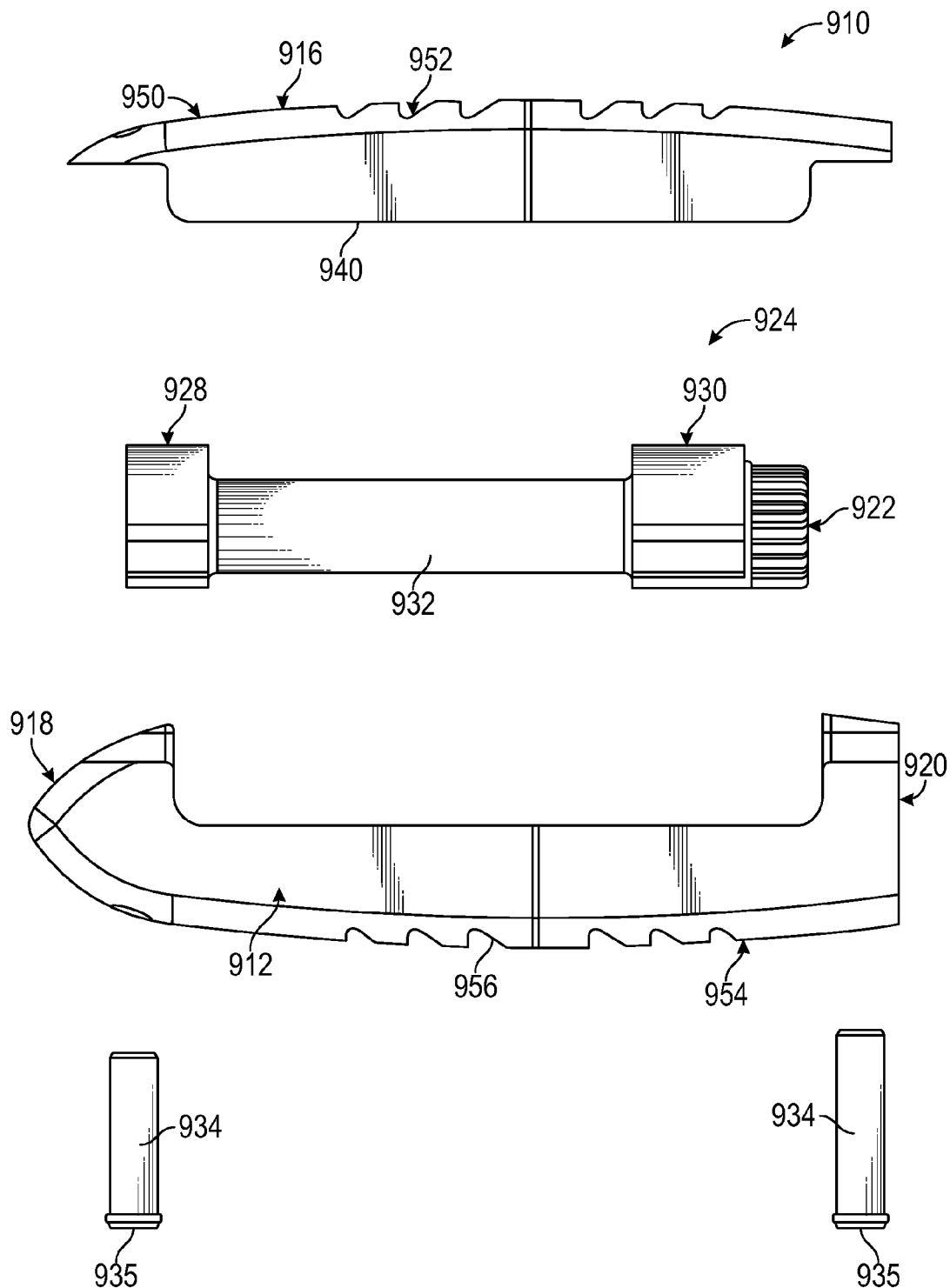
FIG. 96 is a side exploded view of the expandable implant of FIG. 90 according to an exemplary embodiment.

Referring to FIG. 95, shaft 924 includes a shaft body 932, a proximal cam 928, a distal cam 930, and receiver 922. As shown in FIGS. 93 and 96, the length of shaft 924 is slightly less than the length of body assembly 912 and the length of top member 916, such that when shaft 924 is seated in body assembly 912, receiver 922 may be accessed through gap 914 in body assembly 912, and cams 928, 930 may contact an underside 940 of top member 916. In various embodiments, the number and positions of cams, such as cams 928, 930, may be varied.

Figure 98:
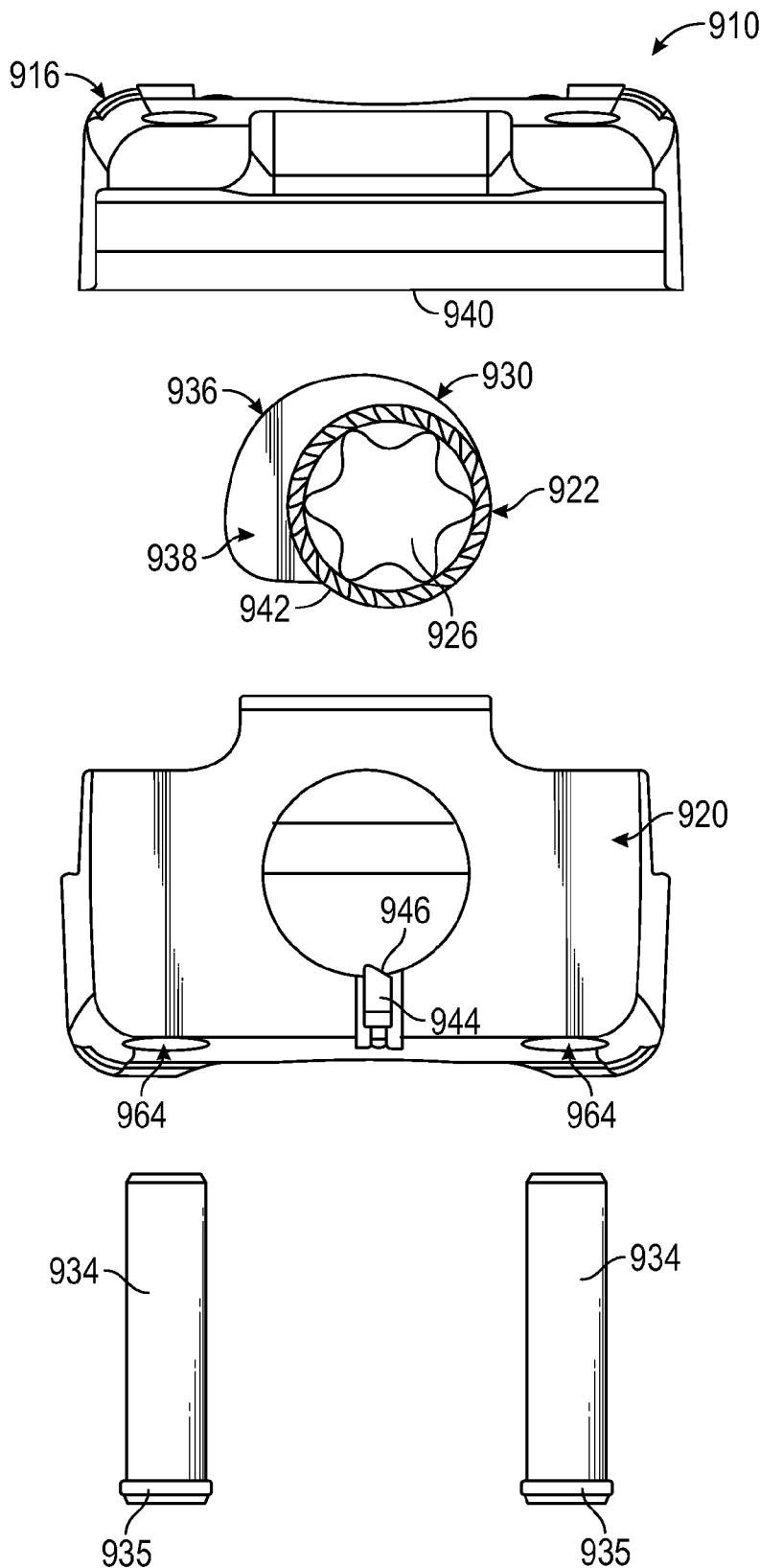
FIG. 98 is an end exploded view of the expandable implant of FIG. 90 according to an exemplary embodiment.
Figure 99:
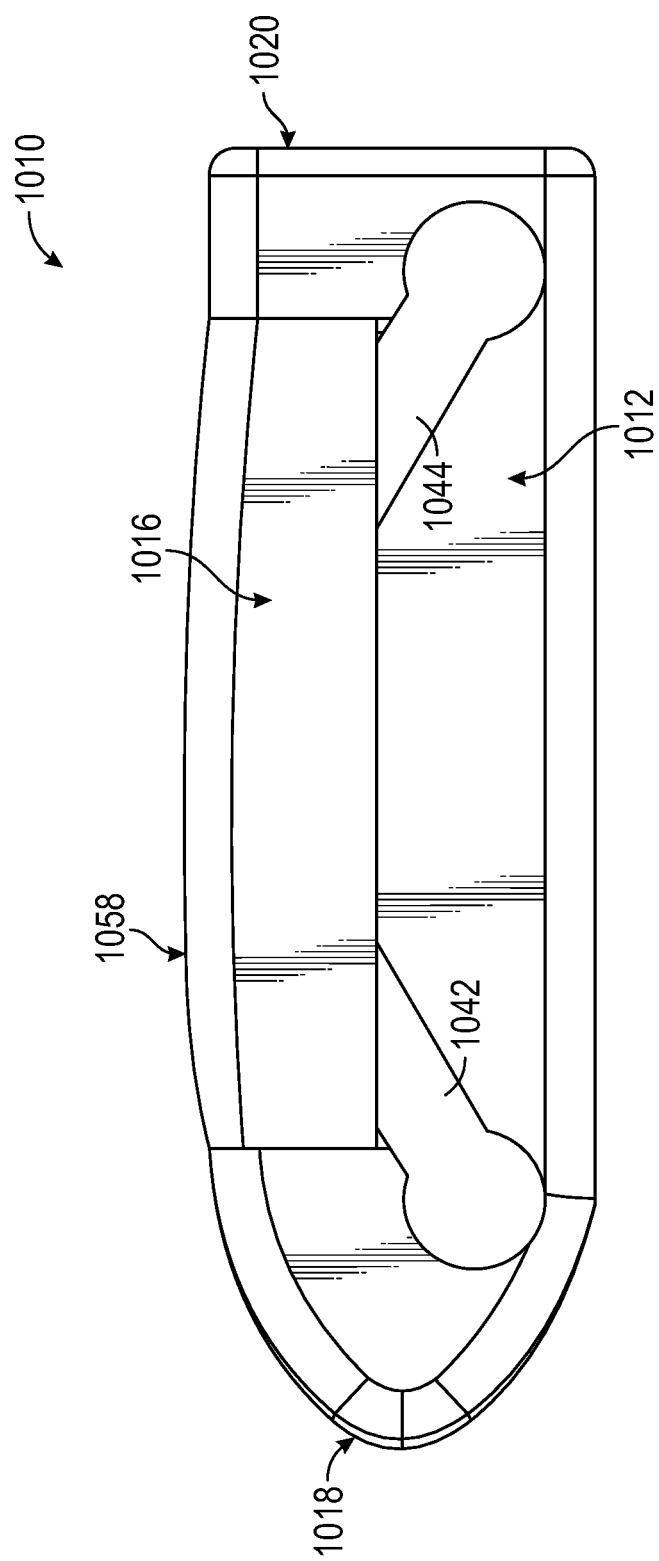
FIG. 99 is a side view of an expandable implant in a contracted configuration according to another exemplary embodiment.
Figure 100:
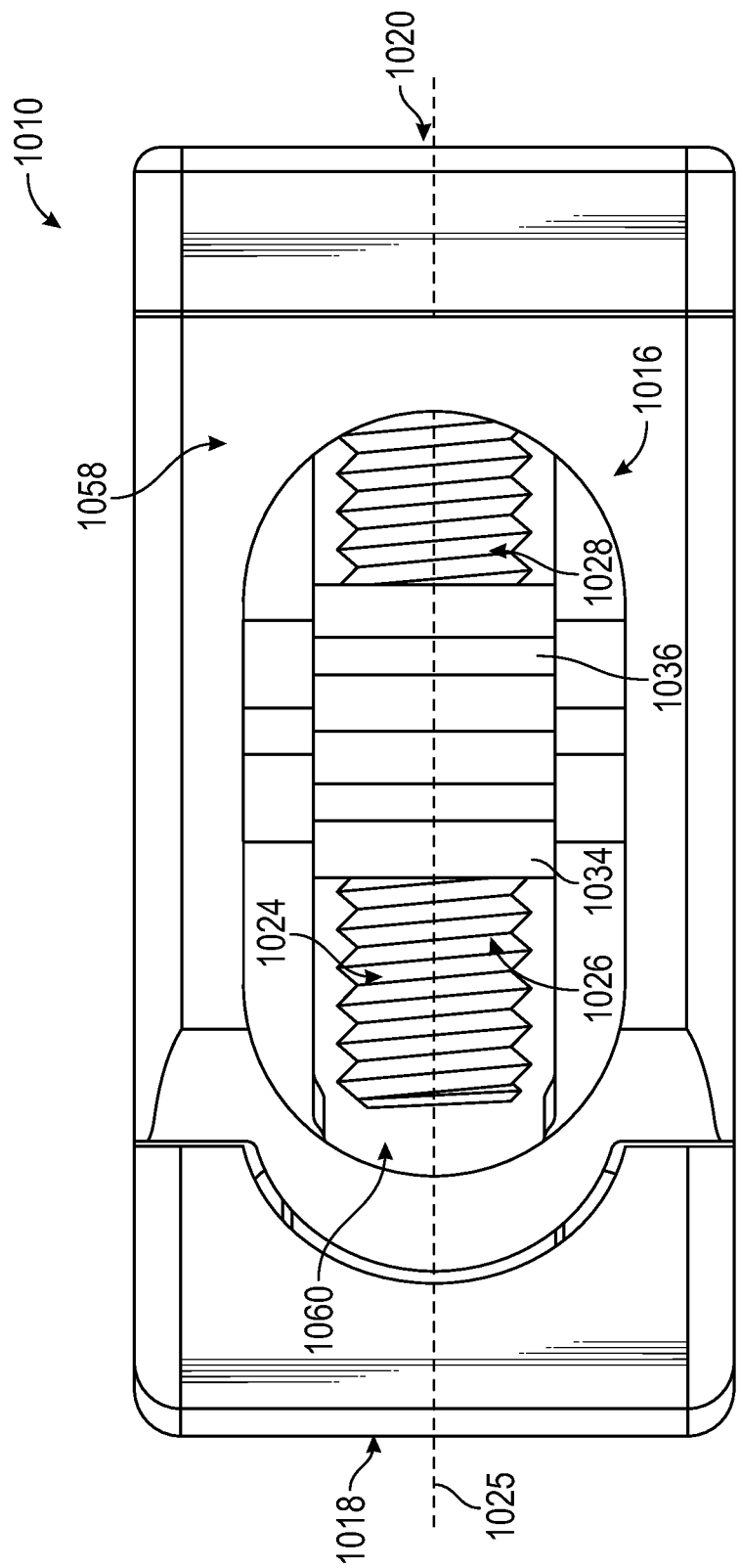
FIG. 100 is a top view of the expandable implant of FIG. 99 according to an exemplary embodiment.

Receiver 922 is configured to be manipulated by a tool, such as a screwdriver, in order to rotate receiver 922 and in turn rotate shaft 924. As shown in FIG. 98, receiver 922 includes a hexalobe head 926, in order to be manipulated by a hex driver. In various embodiments, receiver 922 may include various head components allowing for manipulation by various tools, including but not limited to a Philips head, a flat head, etc.

Figure 97:
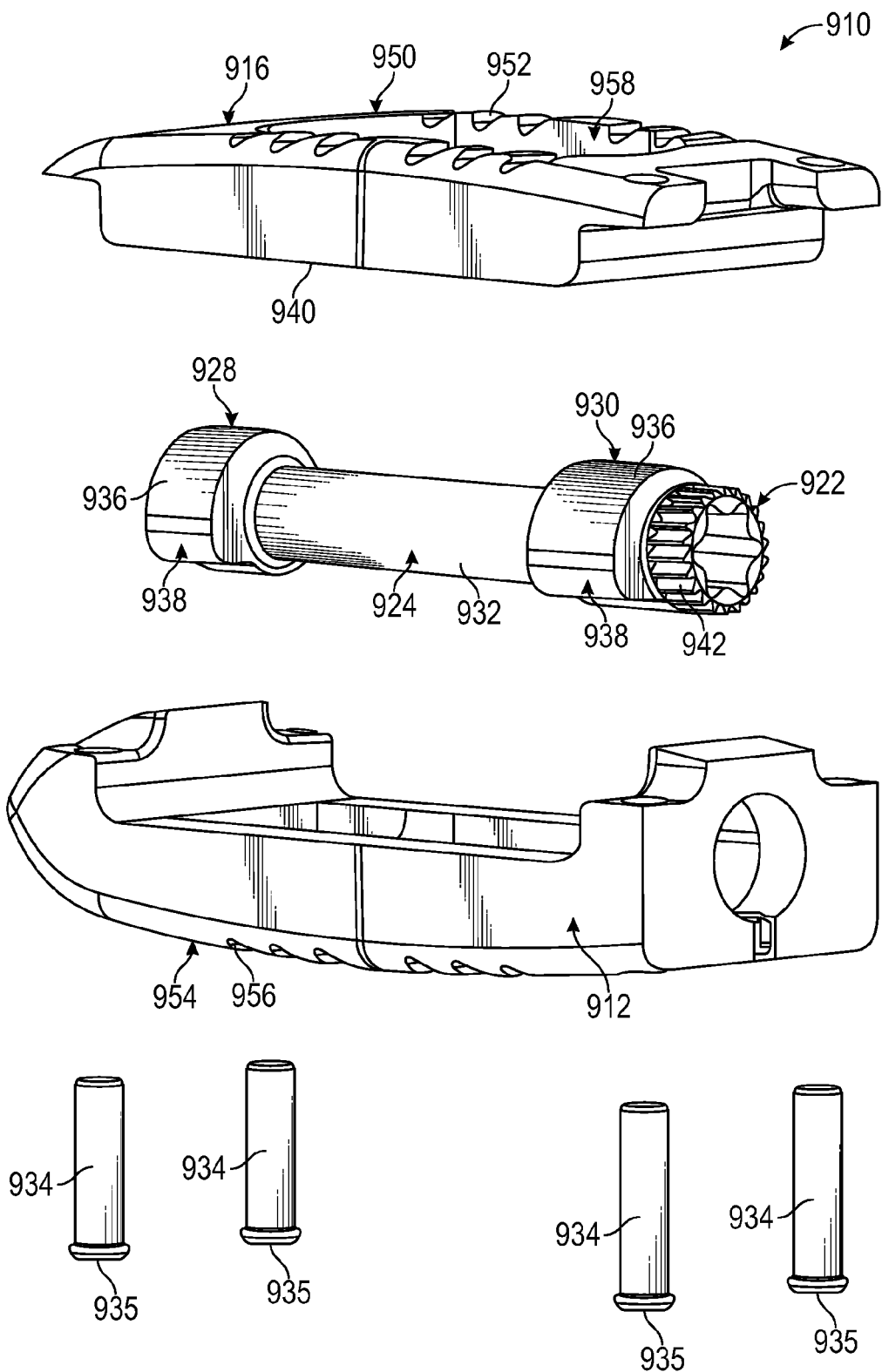
FIG. 97 is a perspective exploded view of the expandable implant of FIG. 90 according to an exemplary embodiment.

Referring to FIGS. 95, 97, and 98, manipulation of receiver 922 (e.g., rotation of receiver 922 and thus rotation of shaft 924) allows for manipulation of the position of top member 916 relative to body assembly 912. Proximal cam 928 and distal cam 930 of implant 910 each include an outer surface 936, which may include a protruding segment 938. Outer surfaces 936 are configured to contact a bottom surface 940 of top member 916. When shaft 924 is rotated, the angular orientation of cams 928, 930 changes, and thus the angular orientation of protruding segments 938 changes. As such, when protruding segments 938 come in contact with bottom surface 940 of top member 916, top member 916 is translated away from body assembly 912. As shown in FIG. 98, in an exemplary embodiment, protruding segment 938 includes a curved profile having an outer radius that varies along outer surface 936 (e.g., a continuously variable radius). As such, proximal cam 928 and distal cam 930 provide a continuous range of distances that top member 916 may be translated away from body assembly 912 (e.g., any top member 916 can be expanded to any position between a contracted position and an expanded position). Body assembly 912 is not translated relative to shaft 924 when shaft 924 is rotated.

Referring to FIGS. 94, 97, and 98, receiver 922 includes a plurality of notches 942. Notches 942 are configured to engage with engagement structure 944 as receiver 922 is rotated and various notches 942 come into contact with engagement structure 944. According to an exemplary embodiment, notches 942 are provided as being biased in one direction (i.e., angled relative to a radius of receiver 922, etc.). Biased notches 942 may allow for receiver 922 and thus shaft 924 to be rotated with little or no resistance in a first direction and with greater resistance in a second direction. Resistance may be provided when engagement structure 944 contacts biased notch 942. For example, as shown in FIGS. 94 and 98, engagement structure 944 may be provided as a pawl 944 having an angled surface 946 that allows notch 942 to slide along pawl 944 when receiver 922 is rotated in a first direction, while abutting notch 942 and thus resisting rotation of receiver 922 in a second direction. In various embodiments, the first direction is a clockwise rotation and the second direction is a counter-clockwise rotation; the first direction may also be a counter-clockwise rotation while the second direction is a clockwise direction. The resistive/ratcheting function providing by engagement structure 944 and notches 942 helps prevent top member 916 from being collapsed (e.g., translated towards body assembly 912) when implant 910 is implanted and force is applied to top member 916 from a structure in the body of a patient. In some embodiments, the resistive/ratcheting function, along with the variable outer radius of cams 928, 930, allows for selection of a specific distance that top member 916 may be translated away from body assembly 912 (e.g., a user implanting implant 910, such as a surgeon, may use a tool for rotating receiver 922 by discrete amounts, until a desired spacing between body assembly 912 and top member 916 is achieved).

Referring to FIGS. 90-94 and 96-98, top member 916 includes grooves 952 provided along an outer surface 950 of top member 916. Similarly, body assembly 912 includes outer surface 954, and may include grooves 956, which may be formed by teeth, projections, or similar structures. While FIGS. 90-94 and 96-98 show grooves 952, 956 following a path generally perpendicular to longitudinal axis 911, in various embodiments, grooves 952, 956 may be disposed in various orientations, such as running parallel to longitudinal axis 911. A bottom surface (e.g., underside, outer surface, etc.) of body assembly 912 is configured to engage (e.g., contact, adjoin, couple, etc.) a vertebral body. Grooves 952, 956 may help secure implant 910 in the body of a patient, by providing spaces for structures in the body of a patient to engage grooves 952, 956. Top member 916 may also include an aperture 958 which, for example, allows access to an interior of implant 910, such as access to shaft 924, etc.

Referring now to FIGS. 99-103, an expandable implant 1010 (e.g., an interbody device, an intrabody device, etc.) is shown according to an exemplary embodiment. Implant 1010 is usable, for example, between and/or within vertebral bodies of the spine, and may share many of the features of the other inter/intra-body implants discussed elsewhere herein. However, it should be understood that implant 1010 may have other uses in other portions of a patient's body in addition to the spine (e.g., inside or around bone, such as a femur, as a cement restrictor, etc.). All such applications are understood to be within the scope of the present disclosure.

According to an exemplary embodiment, implant 1010 includes a body assembly 1012 and a top member 1016. Similar to implant 910, manipulation of components of implant 1010 allows for top member 1016 to be expanded (e.g., translated away from body assembly 1012) or contracted (e.g., translated towards body assembly 1012). Body assembly 1012 may be provided as an integral (e.g., molded in one piece) body traversing from a proximal end 1018 (e.g., first end, front end etc.) to a distal end 1020 (e.g., second end, back end, etc.) of implant 1010. Body assembly 1012 is provided as a body forming a front, bottom, and rear of the implant 1010.

Similar to various implants disclosed herein, including implants 810 and 910, proximal end 1018 may include a bull nose shape facilitating insertion of implant 1010 into a patient during surgery. At distal end 1020, a gap 1014 allows for access to an interior of implant 1010, and particularly to a receiver 1022. Implant 1010 may be implanted in various orientations, such that top member 1016 is not necessarily above or below other components of implant 1010. Top member 1016 of implant 1010 includes an aperture 1060 in an outer surface 1058 of top member 1016, which may allow access to an interior of implant 1010.

Figure 101:
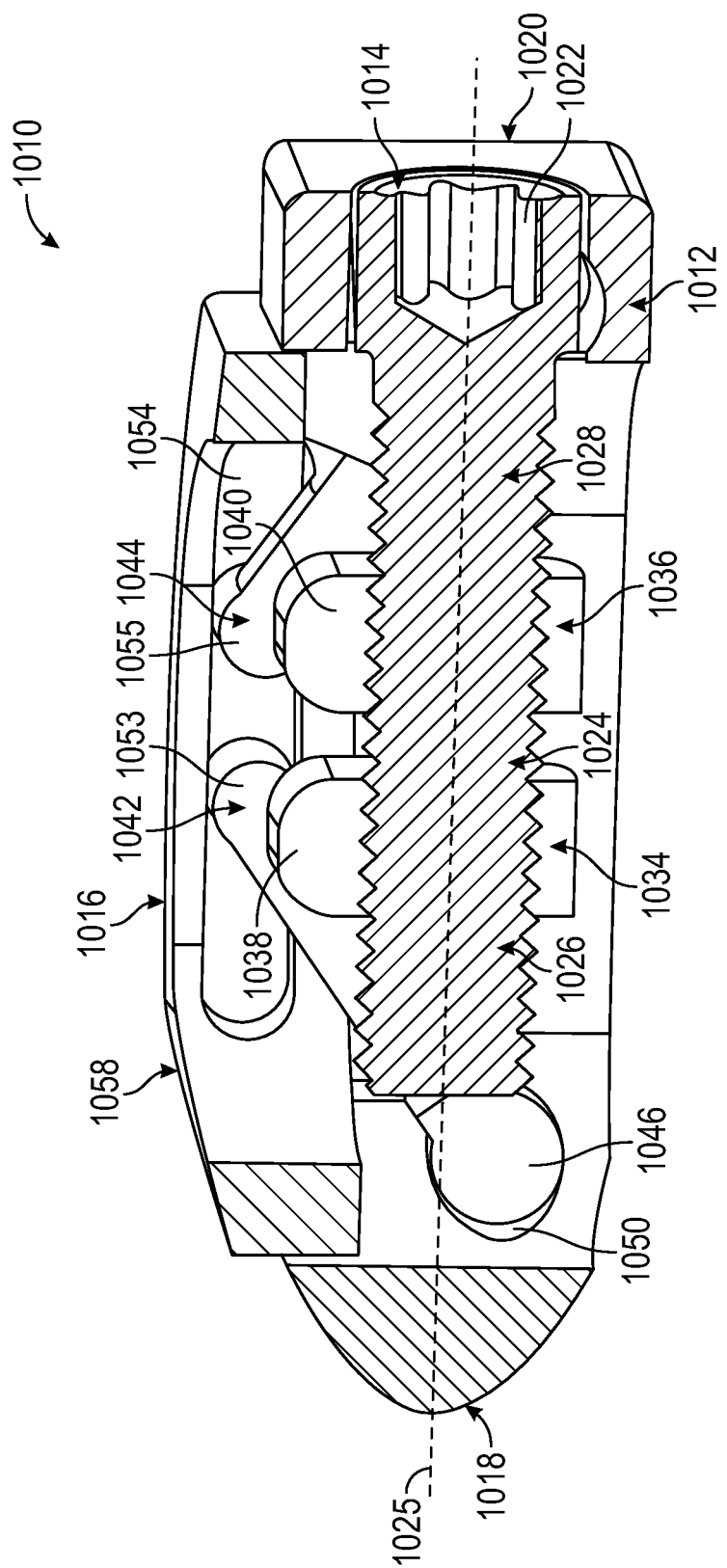
FIG. 101 is a sectional view of the expandable implant of FIG. 99 in an expanded configuration according to an exemplary embodiment.

Referring further to FIG. 101, implant 1010 includes a shaft 1024 having a proximal region 1026 and a distal region 1028. Shaft 1024 includes thread, allowing for movement of a proximal vertical member 1034 and a distal vertical member 1036. Vertical members 1034, 1036 are threadingly coupled to shaft 1024. In various embodiments, the thread along shaft 1024 may be configured so that vertical members 1034, 1036 move (e.g., translate along a longitudinal axis 1025 defined by shaft 1024) in certain directions depending on a direction of rotation of shaft 1024. For example, shaft 1024 and distal vertical member 1036 may be provided with right-handed thread, while proximal vertical member 1034 is provided with left-handed thread, such that rotation of shaft 1024 in a clockwise direction causes vertical members 1034, 1036 to translate away from each other (i.e., proximal vertical member 1034 translates towards proximal end 1018 while distal vertical member 1036 translates towards distal end 1020); rotation of shaft 1024 in a counter-clockwise direction causes vertical members 1034, 1036 to translate towards each other (i.e., proximal vertical member translates towards distal end 1020 while distal vertical member 1036 translates towards proximal end 1018).

Implant 1010 includes a proximal arm 1042 coupled to top portion 1038 of proximal vertical member 1034, and a distal arm 1044 coupled to top portion 1040 of distal vertical member 1036. The coupling may be by a pin, a pivot joint, a roller, a bolt, a peg, etc. Proximal arm 1042 includes a base 1046 disposed in a proximal cavity 1050 of body assembly 1012, allowing for rotation of proximal arm 1042 about a rotational axis passing through base 1046. Similarly, distal arm 1044 includes a base 1048 disposed in a distal cavity 1052 of body assembly 1012, allowing for rotation of distal arm 1044 about a rotational axis passing through base 1048. The pivotable couplings between arms 1042, 1044 and vertical members 1034, 1036 allow vertical members 1034, 1036 to rotate arms 1042, 1044. For example, when proximal vertical member 1034 translates towards proximal end 1018, proximal arm 1042 rotates away from shaft 1024; when proximal vertical member 1034 translates away from proximal end 1018, proximal arm 1042 rotates towards shaft 1024; when distal vertical member 1036 translates towards distal end 1020, distal arm 1044 rotates away from shaft 1024; when distal vertical member 1036 translates away from distal end 1020, distal arm 1044 rotates towards shaft 1024.

Figure 102:
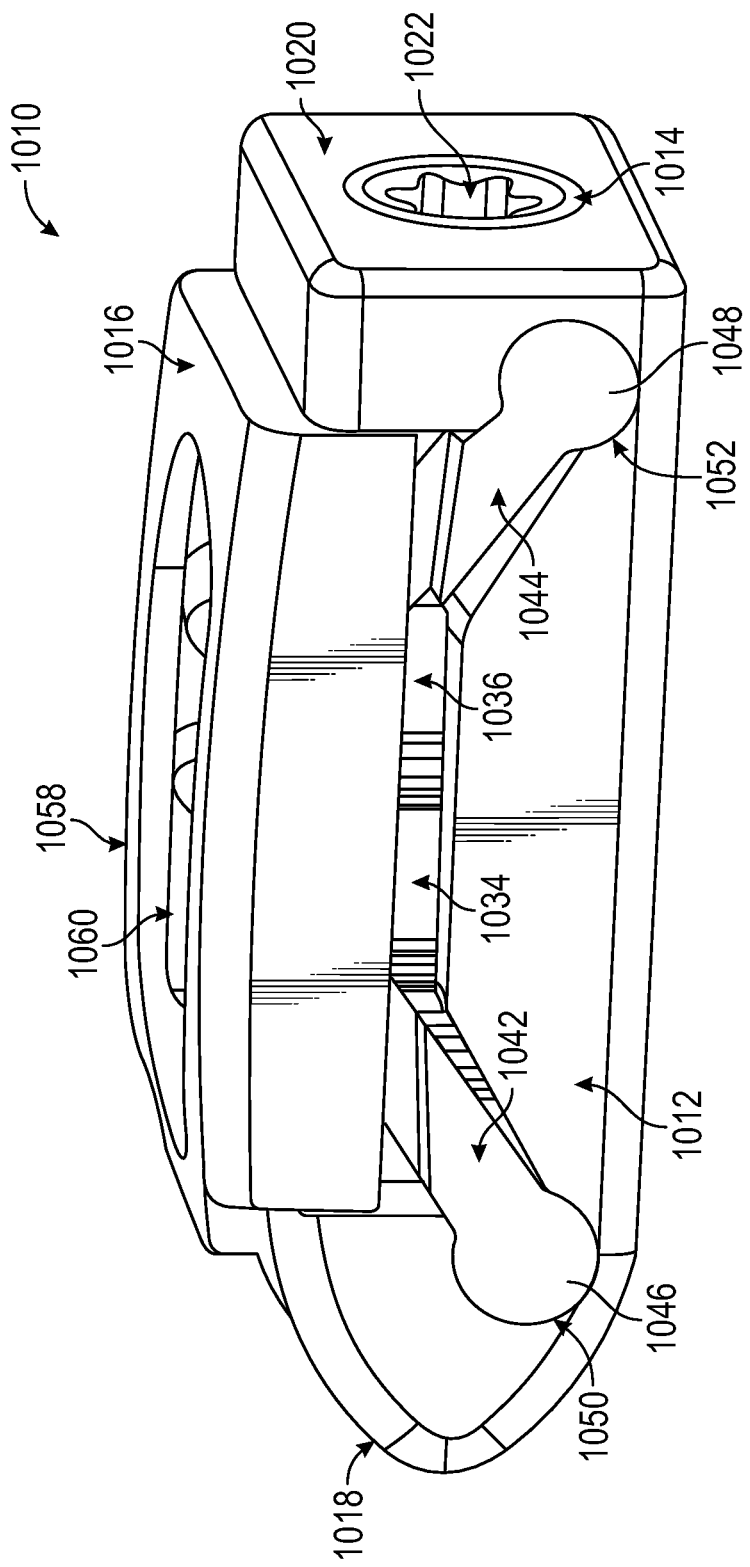
FIG. 102 is a perspective view of the expandable implant of FIG. 99 in an expanded configuration according to an exemplary embodiment.

Proximal arm 1042 and distal arm 1044 each are attached to top member 1016 and configured to translate top member 1016 away from shaft 1024 when arms 1042, 1044 move away from shaft 1024, and to translate top member 1016 towards shaft 1024 when arms 1042, 1044 move towards shaft 1024. For example, as shown in FIGS. 101-102, proximal arm 1042 includes a proximal arm end 1053 disposed on an opposite side of arm 1042 as base 1046; distal arm 1044 includes a distal arm end 1055 disposed on an opposite side of arm 1044 as base 1048; and arm ends 1053, 1055 are configured to slide in a slot 1054 provided within top member 1016 (e.g., arm ends 1053, 1055 may include pins, etc., fitting into slot 1054). When arms 1042, 1044 rotate towards/away from shaft 1016, vertical distances between arm ends 1053, 1055 and shaft 1024 decrease/increase, and thus top member 1016 is translated towards/away from shaft 1024 and body assembly 1012.

Figure 103:
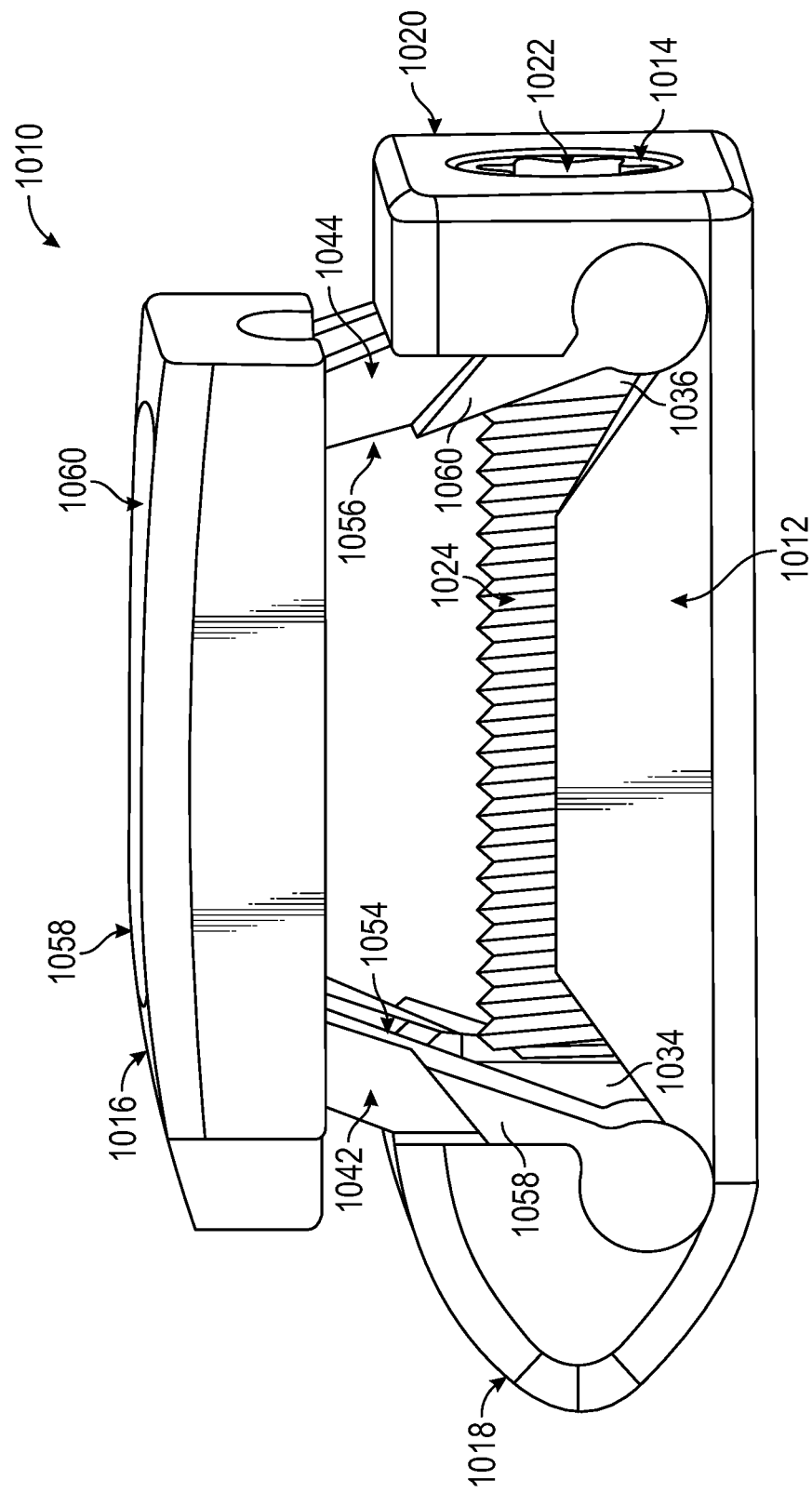
FIG. 103 is a perspective view of the expandable implant of FIG. 99 in another expanded configuration according to an exemplary embodiment.

Referring further to FIG. 103, additional aspects of interplay between vertical members 1034, 1036, arms 1042, 1044, body assembly 1012, and top member 1016 are shown. In an exemplary embodiment, arms 1042, 1044 are provided with channels or tracks, such as channels 1054, 1056, allowing for vertical members 1034, 1036 to ride within the channels as vertical members 1034, 1036 translate along shaft 1024 and push up arms 1042, 1044. Arms 1042, 1044 may include notched lower portions 1058, 1060.

Referring now to FIGS. 104-109, an expandable implant 1110 (e.g., an interbody device, an intrabody device, etc.) is shown according to an exemplary embodiment. Implant 1110 is usable, for example, between and/or within vertebral bodies of the spine, and may share many of the features of the other inter/intra-body implants discussed elsewhere herein. However, it should be understood that implant 1110 may have other uses in other portions of a patient's body in addition to the spine (e.g., inside or around bone, such as a femur, as a cement restrictor, etc.). All such applications are understood to be within the scope of the present disclosure.

According to an exemplary embodiment, implant 1110 includes a body assembly 1112 formed of a top member 1114 (e.g., first member, upper member, etc.), a bottom member 1116 (e.g., second member, lower member, etc.), and a central body 1118, including a proximal portion 1120 (e.g., first portion, front portion, etc.) and a distal portion 1122 (e.g. second portion, back portion, etc.). Central body 1118 includes a pair of inner walls 1124 generally connecting proximal portion 1120 to distal portion 1122. Inner walls 1124 may attach to proximal portion 1120 and distal portion 1122 inside of outer surfaces 1126, 1128 of proximal portion 1120 and distal portion 1122 (e.g., inner walls 1124 may connect an inner surface of proximal portion 1120 to an inner surface of distal portion 1122, etc.).

Figure 108:
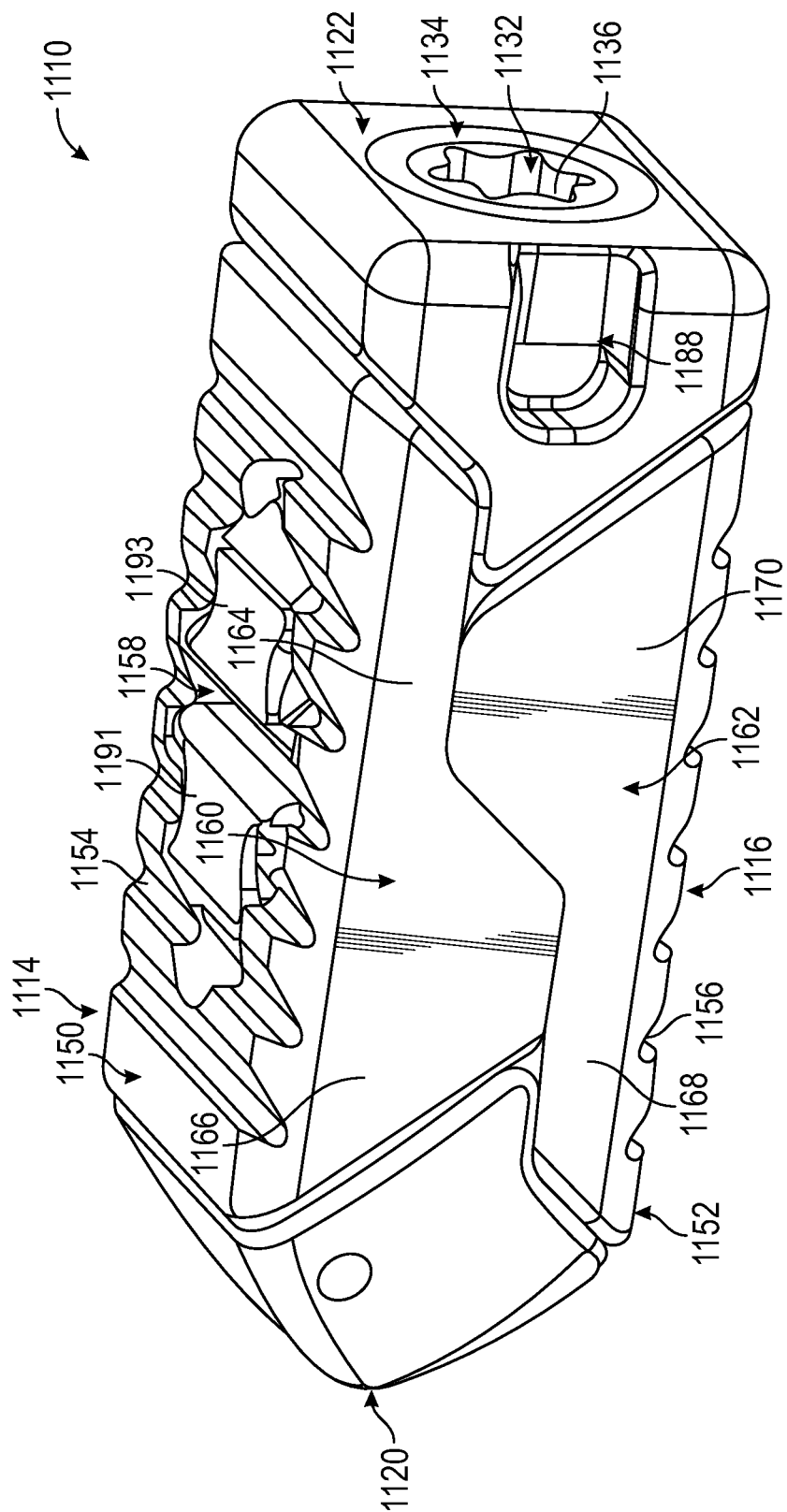
FIG. 108 is a perspective view of the expandable implant of FIG. 104 in a contracted configuration according to an exemplary embodiment.
Figure 109:
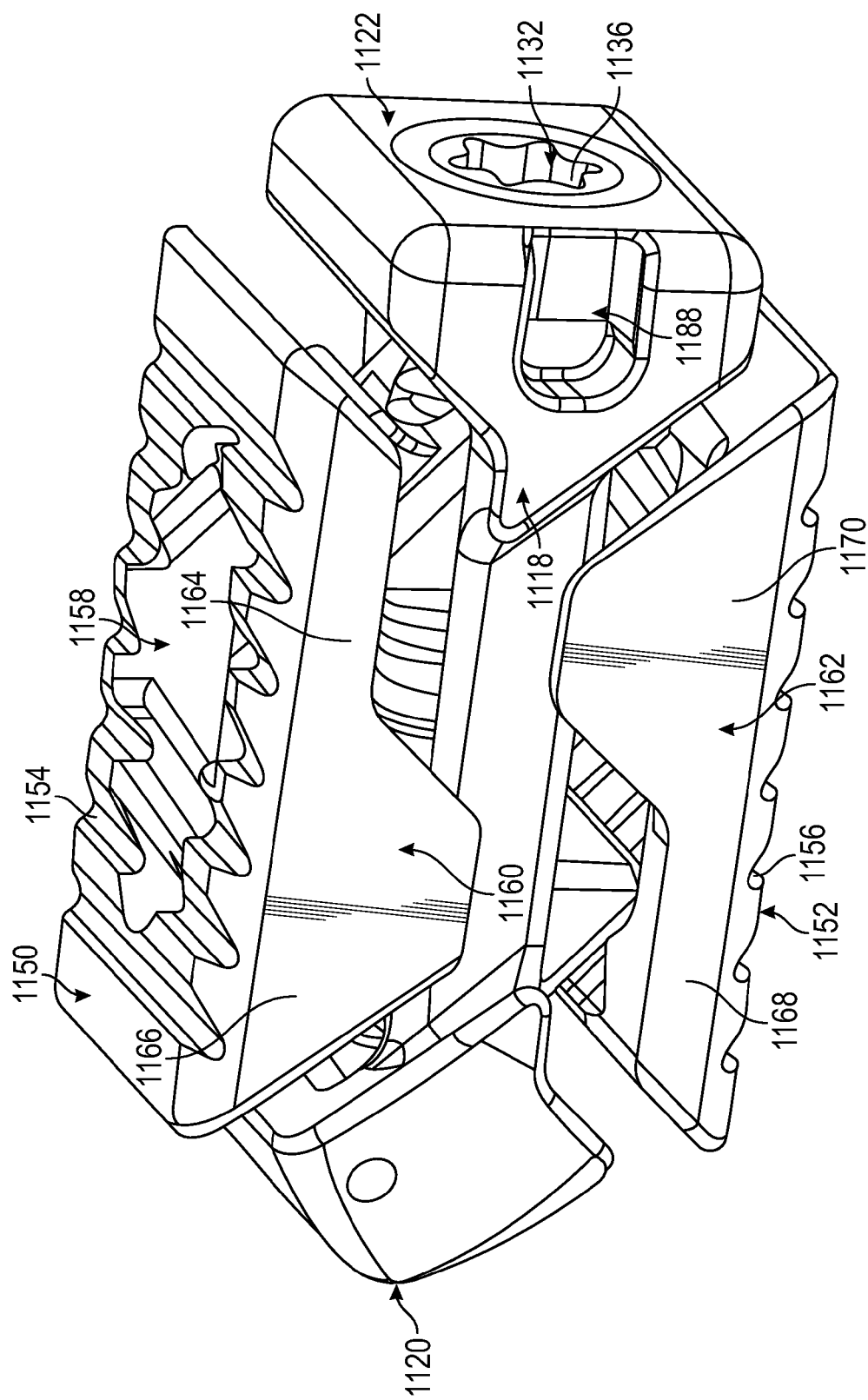
FIG. 109 is a perspective view of the expandable implant of FIG. 104 in an expanded configuration according to an exemplary embodiment.

Implant 1110 includes a shaft 1130 generally traversing between proximal and distal portions 1120, 1122 of implant 1110. Shaft 1130 may be disposed between inner walls 1124. Shaft 1130 includes a receiver 1132 which is configured to rotate shaft 1130 when receiver 1132 is rotated. Receiver 1132 is accessible through a gap 1134 provided on outer surface 1128 of distal portion 1122. Receiver 1132 includes a head 1136 configured to allow receiver 1132 to be rotated. For example, as shown in FIGS. 108-109, head 1136 is provided as a hexalobe head, such that receiver 1132 may be rotated using a hex tool. In various embodiments, various combinations of heads and tools may be used for rotating receiver 1132.

Figure 106:
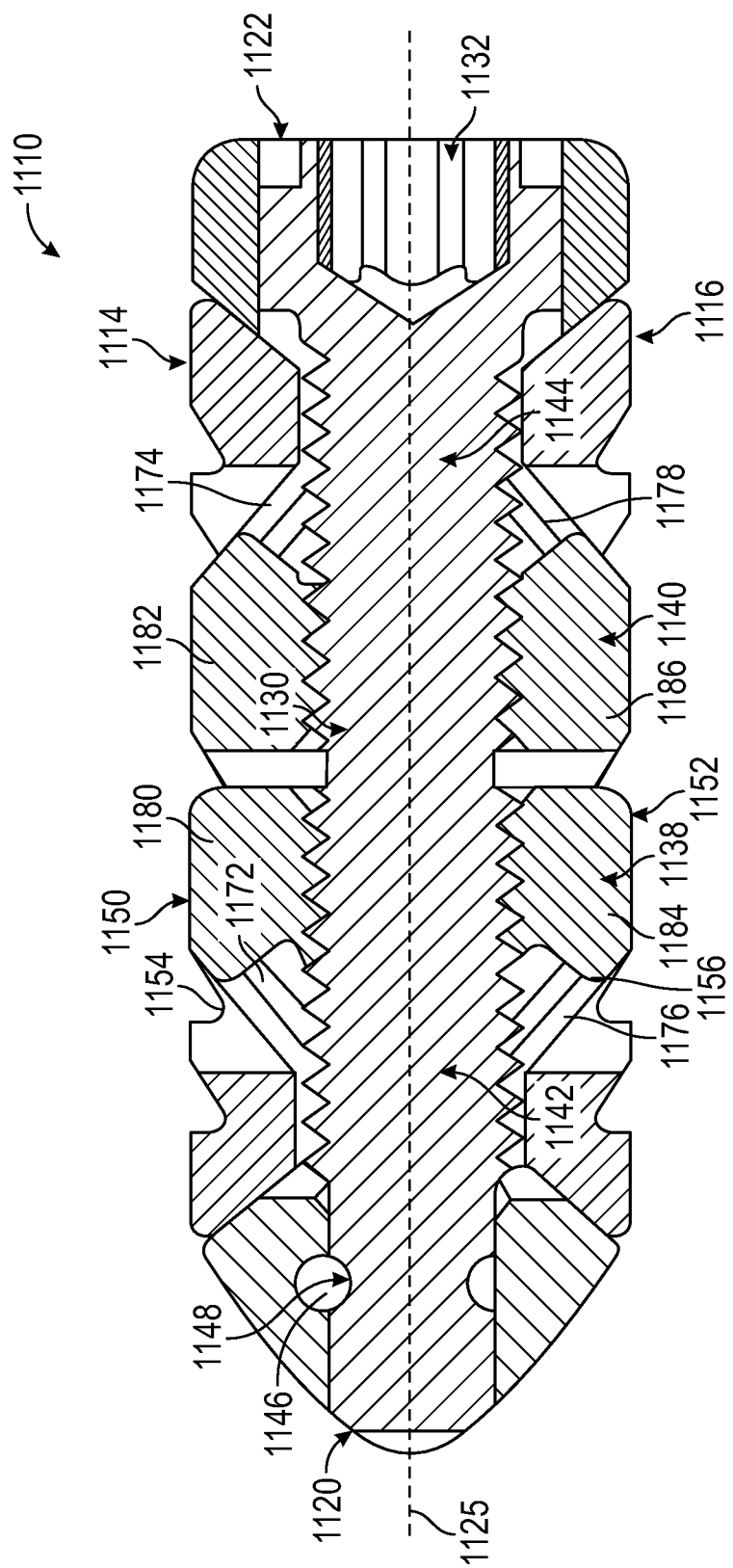
FIG. 106 is a sectional view of the expandable implant of FIG. 104 in a contracted configuration according to an exemplary embodiment.
Figure 107:
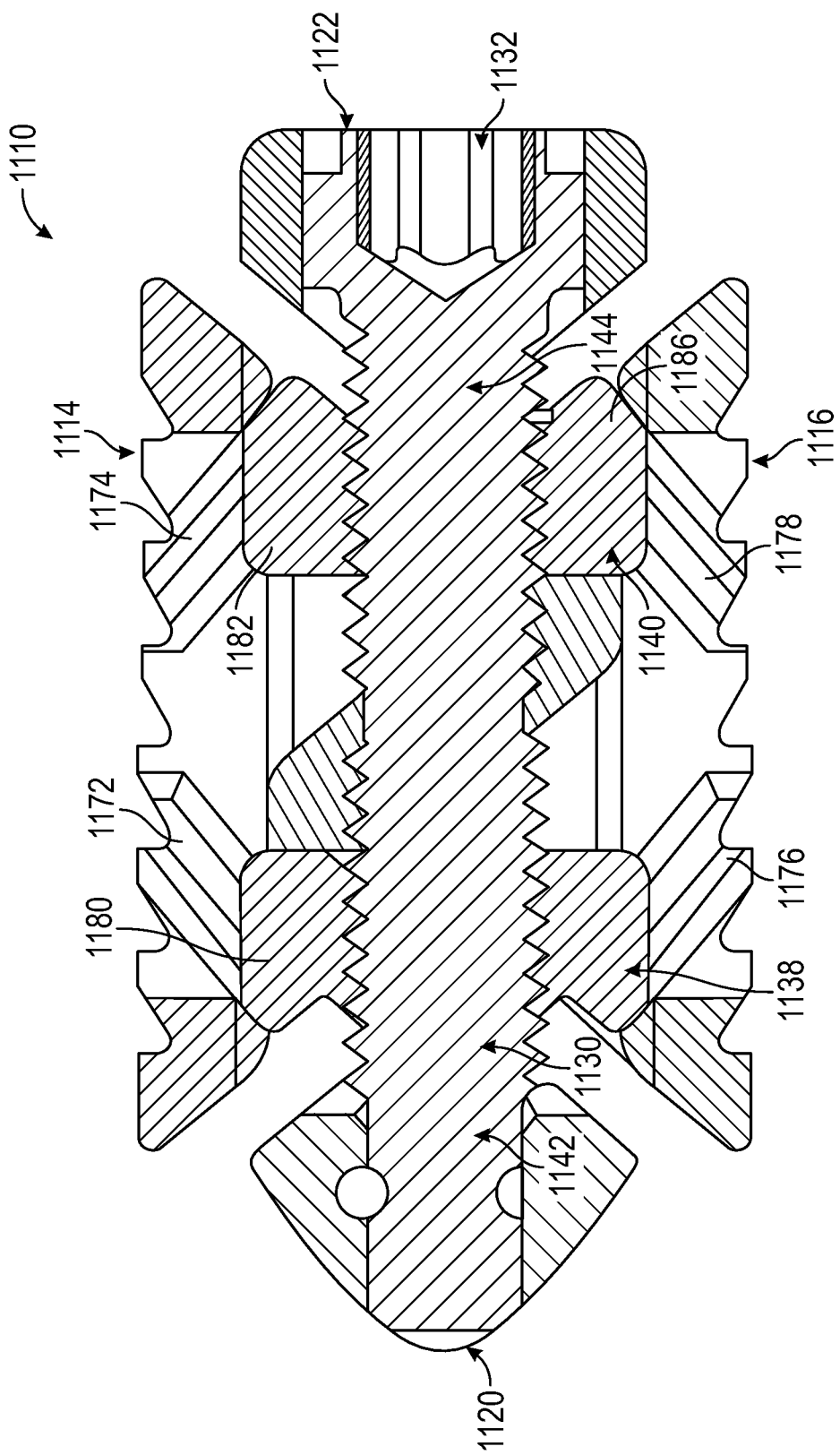
FIG. 107 is a sectional view of the expandable implant of FIG. 104 in an expanded configuration according to an exemplary embodiment.

As shown in FIGS. 106-107, proximal wedge member 1138 and distal wedge member 1140 are each disposed along and threadingly coupled to shaft 1130. In various embodiments, shaft 1130 and wedge members 1138, 1140 are configured to allow wedge members 1138, 1140 to move (e.g., translate along shaft 1130 when shaft 1130 is rotated) in opposite directions.

For example, in various embodiments, shaft 1130 includes a proximal shaft section 1142 having left-handed thread, and a distal shaft section 1144 having right-handed thread. When shaft 1130 is rotated in a clockwise direction, proximal wedge member 1138 will be translated towards proximal portion 1120, while distal wedge member 1140 will be translated towards distal portion 1122. When shaft 1130 is rotated in a counter-clockwise direction, proximal wedge member 1138 will be translated away from proximal portion 1120 (i.e. towards distal portion 1122); distal wedge member 1140 will be translated away from distal portion 1122 (i.e. towards proximal portion 1120).

Figure 104:
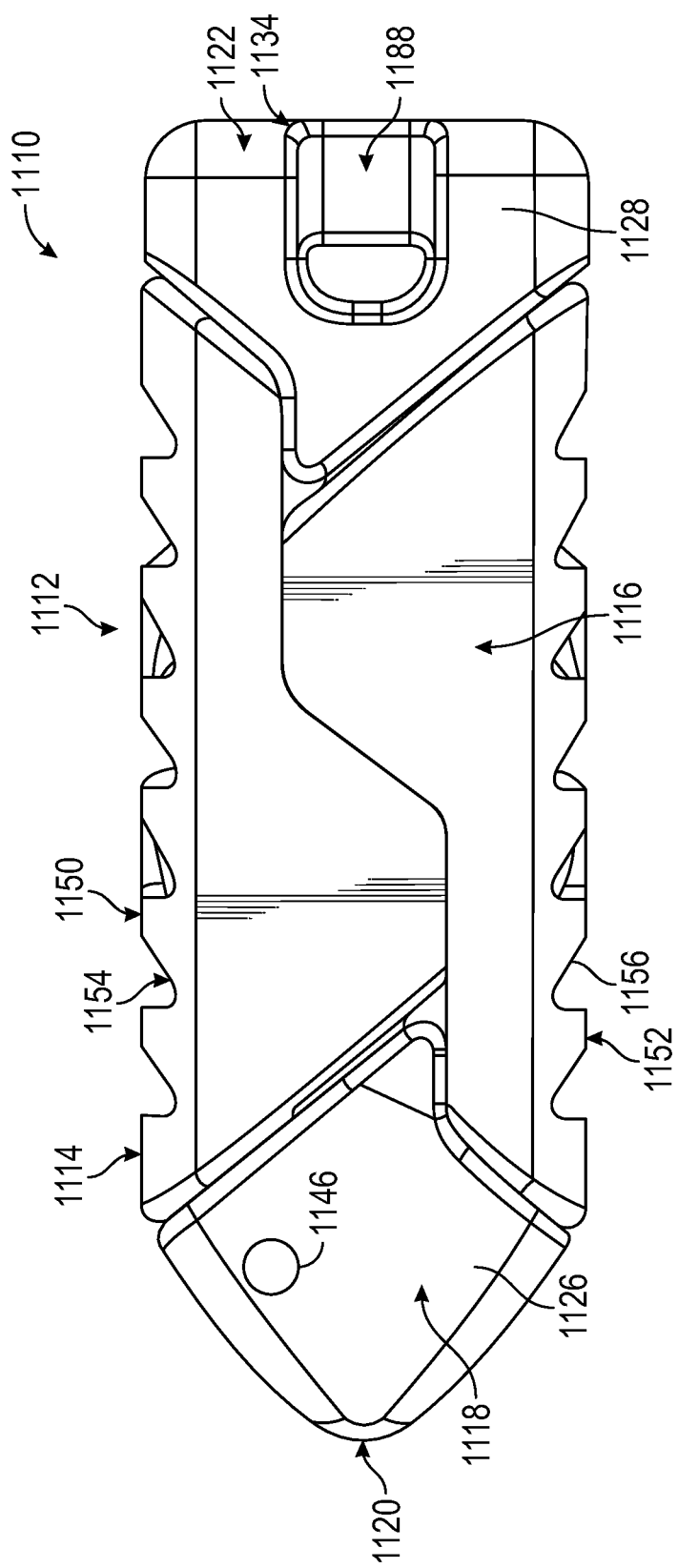
FIG. 104 is a side view of an expandable implant in a contracted configuration according to another exemplary embodiment.
Figure 105:
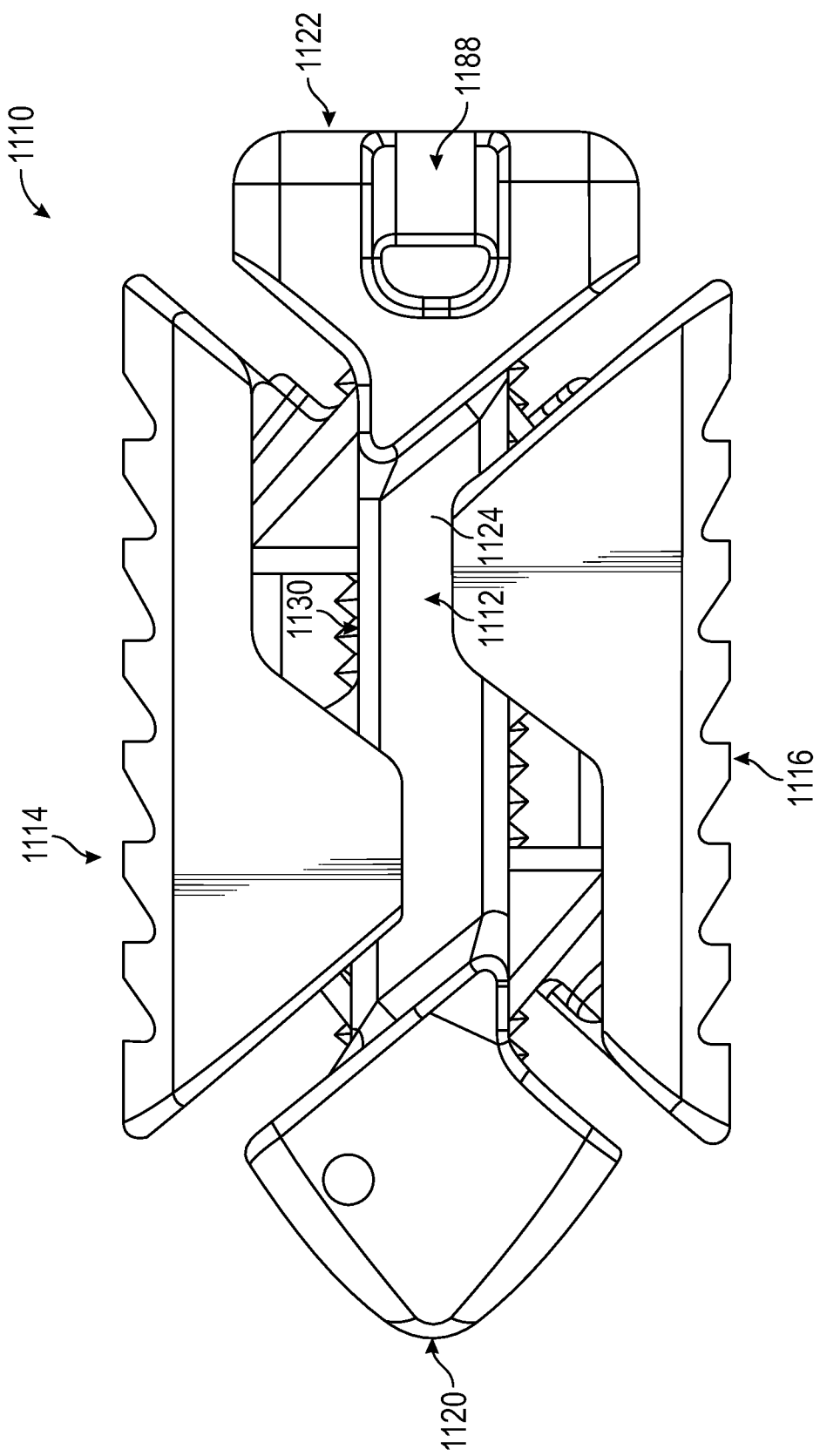
FIG. 105 is a side view of the expandable implant of FIG. 104 in an expanded configuration according to an exemplary embodiment.

Referring to FIGS. 104 and 106, in various embodiments, proximal portion 1120 of implant 1110 includes a pin 1146 running generally perpendicular to a longitudinal axis 1125 and passing through a groove 1148 in proximal shaft section 1142 of shaft 1130.

As shown in FIGS. 104-109, top member 1114 and bottom member 1116 generally include similar form factors with opposite orientations. Top member 1114 and bottom member 1116 may be identical in size and shape. For example, members 1114, 1116 each include an outer face (e.g., a face facing away from shaft 1130, etc.), such as outer faces 1150, 1152. Outer faces 1150, 1152 may include grooves 1154, 1156. While FIGS. 108-109 show grooves 1154, 1156 following a path generally perpendicular to a longitudinal axis 1125, in various embodiments, grooves 1154, 1156 may be disposed various orientations, such as running parallel to longitudinal axis 1125. Grooves 1154, 1156 may help secure implant 1110 in the body of a patient, by providing spaces for structures in the body of a patient to engage grooves 1154, 1156. Members 1114 and 1116 may also include apertures, such as aperture 1158, which, for example, allows access to an interior of implant 1110, such as access to shaft 1130, etc.

Referring further to FIGS. 108-109, top member 1114 and bottom member 1116 also include side faces (e.g., left and/or right faces), such as a side face 1160 of top member 1114, and a side face 1162 of bottom member 1116. Side faces 1160, 1162 may be generally perpendicular to respective members 1114, 1116. Side faces 1160, 1162 may be disposed parallel and outward of inner walls 1124. Side faces 1160, 1162 are configured to engage each other in a complementary fashion when implant 1110 is in a closed configuration (see, e.g., FIG. 108, etc.). For example, as shown in FIGS. 108-109, side face 1160 includes a first region 1164 and a second region 1166 extending further from outer face 1150 than first region 1164. Similarly, side face 1162 includes a first region 1168, and a second region 1170 extending further from outer face 1152 than first region 1168.

Referring further to FIGS. 106-108, top member 1114 includes a proximal track 1172 and a distal track 1174, and bottom member 1116 includes a proximal track 1176 and a distal track 1178. Tracks 1172, 1174, 1176, and 1178 are configured to engage wedge members 1138, 1140. When wedge members 1138, 1140 are translated along shaft 1130 due to rotation of shaft 1130, wedge members 1138, 1140 transfer the force of the rotation in order to slide in tracks 1172, 1174, 1176, 1178, in turn causing members 1114, 1116 to be translated towards or away from shaft 1130. For example, as shown in FIGS. 106-107, a top wedge region 1180 of proximal wedge 1138 is disposed to slide in track 1172; a bottom wedge region 1184 of proximal wedge 1138 is disposed to slide in track 1176; a top wedge region 1182 of distal wedge 1140 is disposed to slide in track 1174; and a bottom wedge region 1186 of distal wedge 1140 is disposed to slide in track 1178. Due to the angled faces of wedges 1138, 1140 and tracks 1172, 1174, 1176, 1178, the forces applied by wedges 1138, 1140 when wedges 1138, 1140 translate along shaft 1130 (i.e., parallel to longitudinal axis 1125) are modified into vertical forces (i.e., perpendicular to longitudinal axis 1125). Tracks 1172, 1174, 1176, 1178 may also include grooves and/or extensions, and wedge members 1138, 1140 may also include complementary grooves and/or extensions, that facilitate engagement between wedge members 1138, 1140 and tracks 1172, 1174, 1176, 1178, in order to expand or collapse implant 1110. In some embodiments, top wedge region 1180 of proximal wedge 1138 includes a proximal dovetail portion 1191, and top wedge region 1182 of distal wedge 1140 includes a distal dovetail portion 1193. Similar to the dovetail shapes of projections 730, 740 of implant 710, projections of implant 810 that extend across front portion 812, etc., dovetail portions 1191, 1193 ensure that wedge members 1138, 1140 can slide in corresponding tracks 1172, 1176, but ensure that the parts cannot be separated, for example, by merely lifting top member 1114 away from central body 1118 (e.g., in an upward direction generally perpendicular to longitudinal axis 1125).

Referring to FIG. 104, implant 1110 may include a recess or containment, such as a recess 1188. A surface (e.g., an outer surface) of body assembly 1112 may define recess 1188. Recess 1188 may be provided for containing material, such as bone graft material; recess 1188 may be provided for attaching an instrument to recess 1188 for installation purposes. While FIG. 104 shows recess 1188 disposed on distal portion 1122 of implant 1110, recess 1188 may be provided on various locations of implant 1110.

Referring now to FIGS. 110-113, an expandable implant 1210 (e.g., an interbody device, an intrabody device, etc.) is shown according to an exemplary embodiment. Implant 1210 is usable, for example, between and/or within vertebral bodies of the spine, and may share many of the features of the other inter/intra-body implants discussed elsewhere herein. However, it should be understood that implant 1210 may have other uses in other portions of a patient's body in addition to the spine (e.g., inside or around bone, such as a femur, as a cement restrictor, etc.). All such applications are understood to be within the scope of the present disclosure. Implant 1210 is generally similar to implant 1110 in structure and function except with respect to the modified alignment features discussed below.

According to an exemplary embodiment, implant 1210 includes a body assembly 1212 formed of a top member 1214 (e.g., upper member, first member, etc.), a bottom member 1216 (e.g., lower member, second member, etc.), and a central body 1218, central body 1218 including a proximal portion 1220 (e.g., first portion, front portion, etc.) and a distal portion 1222 (e.g., second portion, back portion, etc.). Central body 1218 also includes lateral control members 1224, 1226, disposed on either side (e.g., left/right; lateral/contralateral; etc.) of central body 1218 and generally between proximal portion 1220 and distal portion 1222, and generally between top member 1214 and bottom member 1216. Lateral control members 1224, 1226 are configured to control the orientation of members 1214, 1216 as members 1214, 1216 are expanded/collapsed (i.e. translated away from/towards central body 1218).

Implant 1210 includes a shaft 1228 configured to be rotated, for example, by rotation of a receiver 1230. Rotation of shaft 1228 expands/contracts members 1214, 1216 in a similar manner as to other implants disclosed herein, such as implant 1110 through the use of wedge members and tracks, etc. For example, similar to implant 1110, implant 1210 includes dovetail portions 1291, 1293 prevent the parts of implant 1210 from being separated by merely lifting top member 1214 (e.g., in an upward direction generally perpendicular to longitudinal axis 1225).

Figure 110:
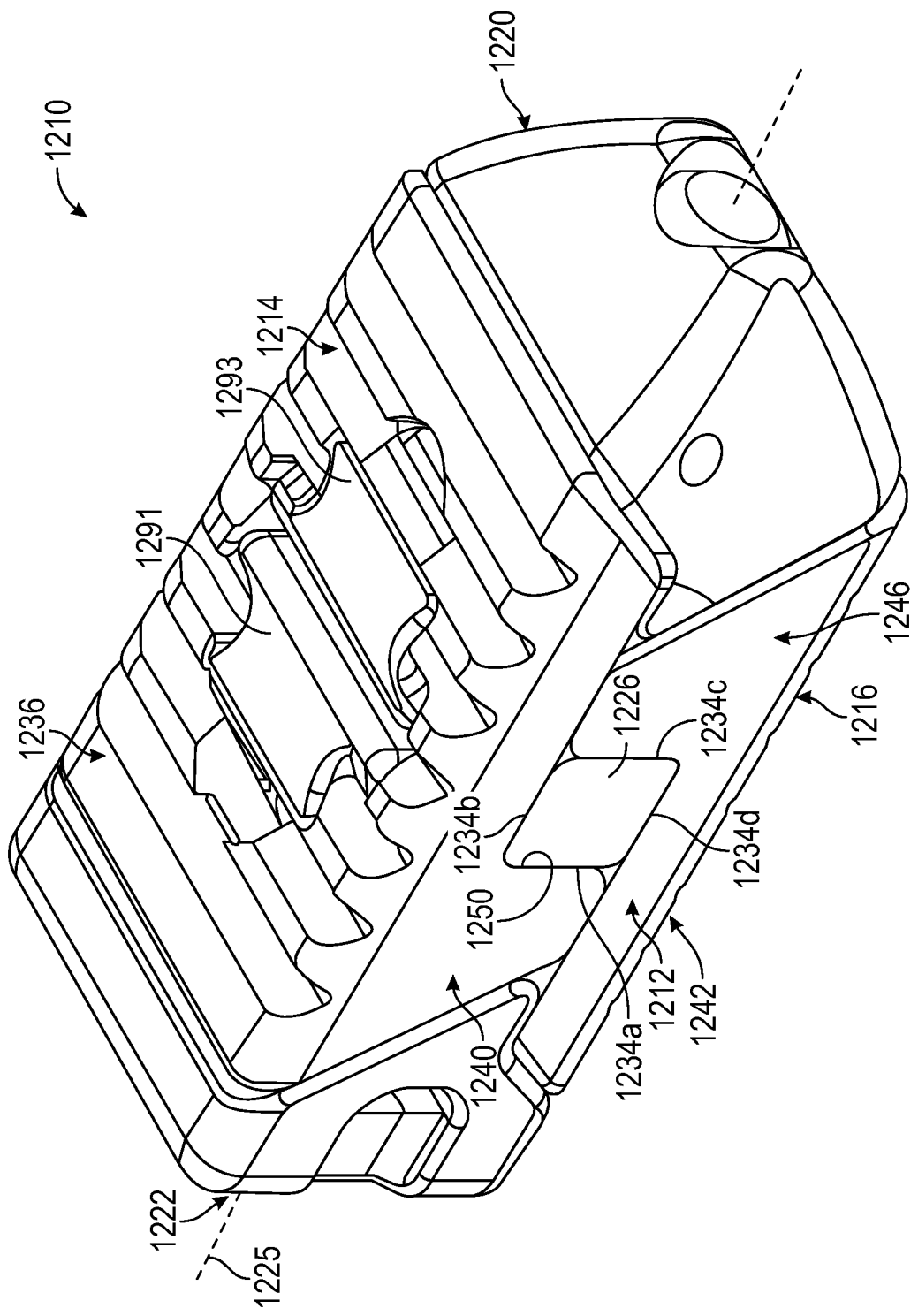
FIG. 110 is a perspective view of an expandable implant in a contracted configuration, with a proximal end of the implant provided on a right side of the view and a distal end of the implant provided on a left side of the view, according to another exemplary embodiment.
Figure 111:
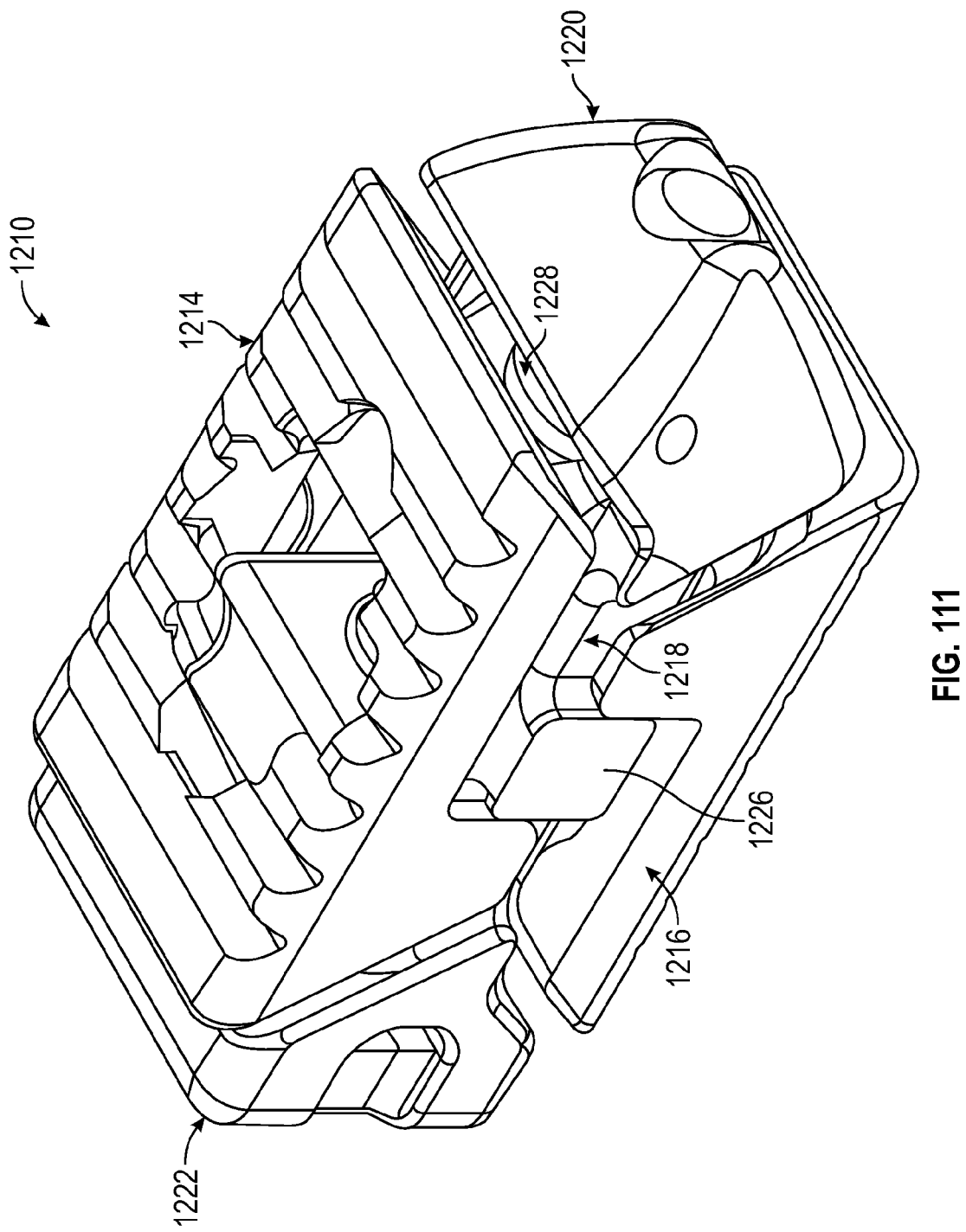
FIG. 111 is a perspective view of the expandable implant of FIG. 110 in an expanded configuration, with a proximal end of the implant provided on a right side of the view and a distal end of the implant provided on a left side of the view, according to an exemplary embodiment.
Figure 112:
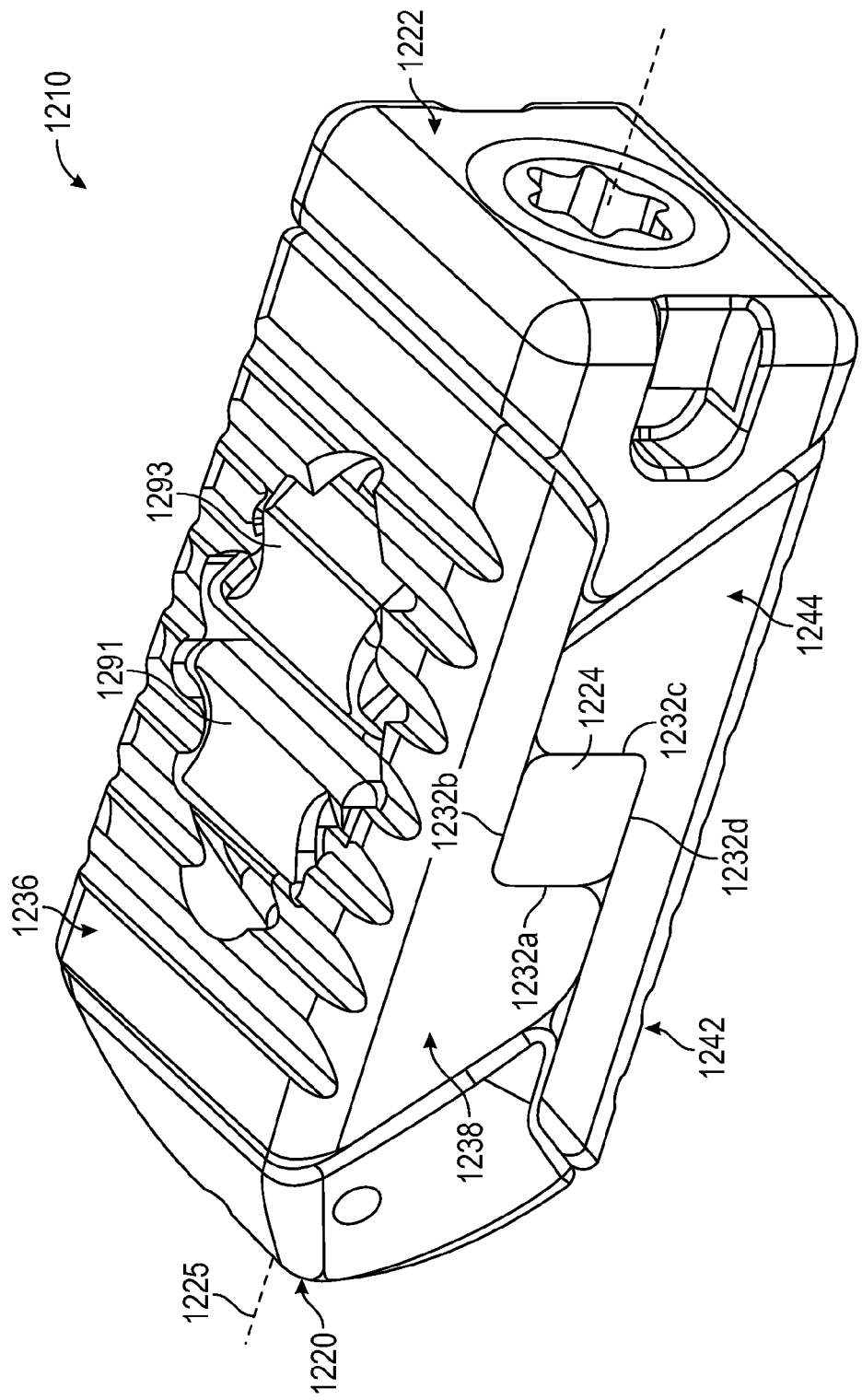
FIG. 112 is a perspective view of the expandable implant of FIG. 110 in a contracted configuration, with a proximal end of the implant provided on a left side of the view and a distal end of the implant provided on a right side of the view, according to an exemplary embodiment.
Figure 113:
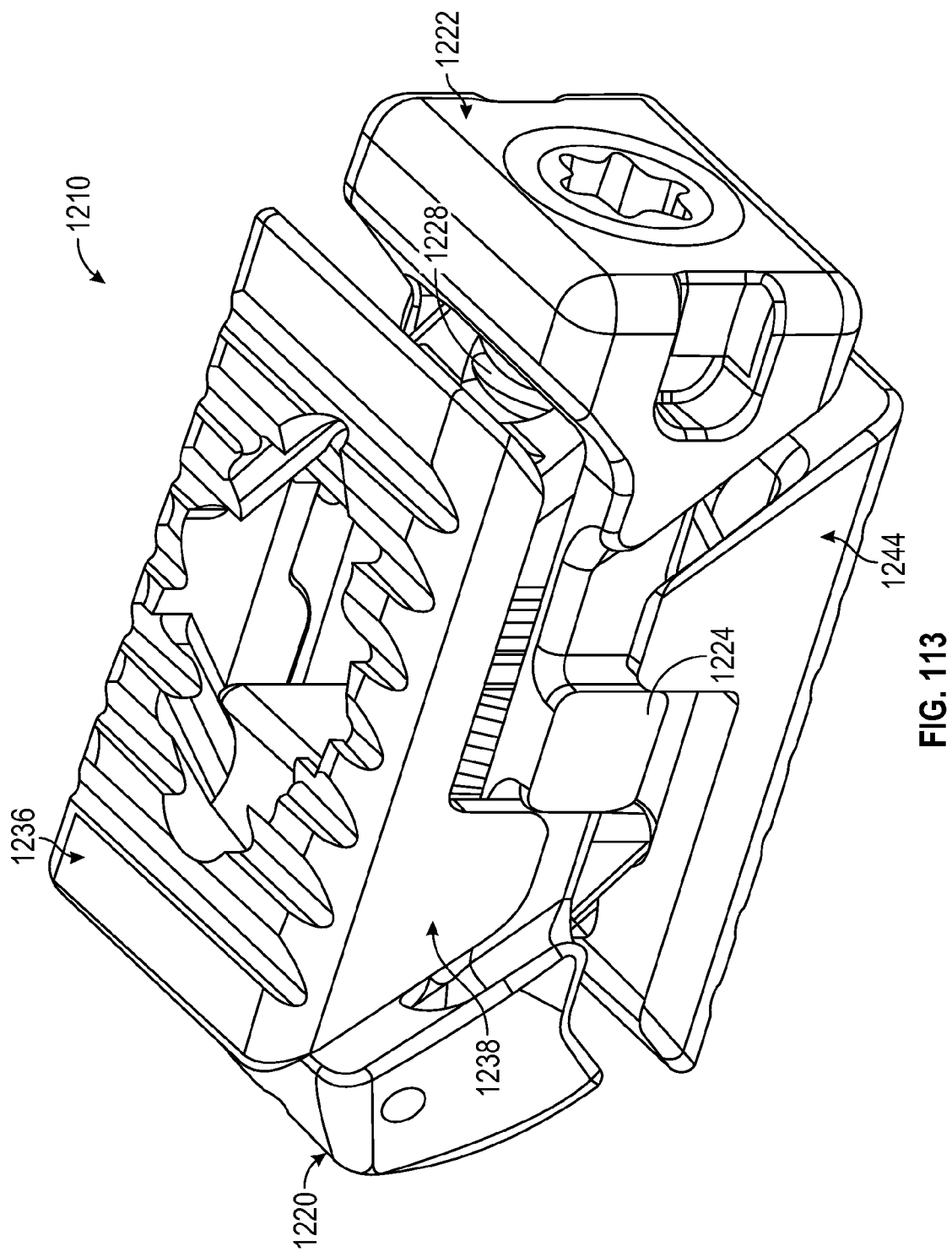
FIG. 113 is a perspective view of the expandable implant of FIG. 110 in an expanded configuration, with a proximal end of the implant provided on a left side of the view and a distal end of the implant provided on a right side of the view, according to an exemplary embodiment.
Figure 114:
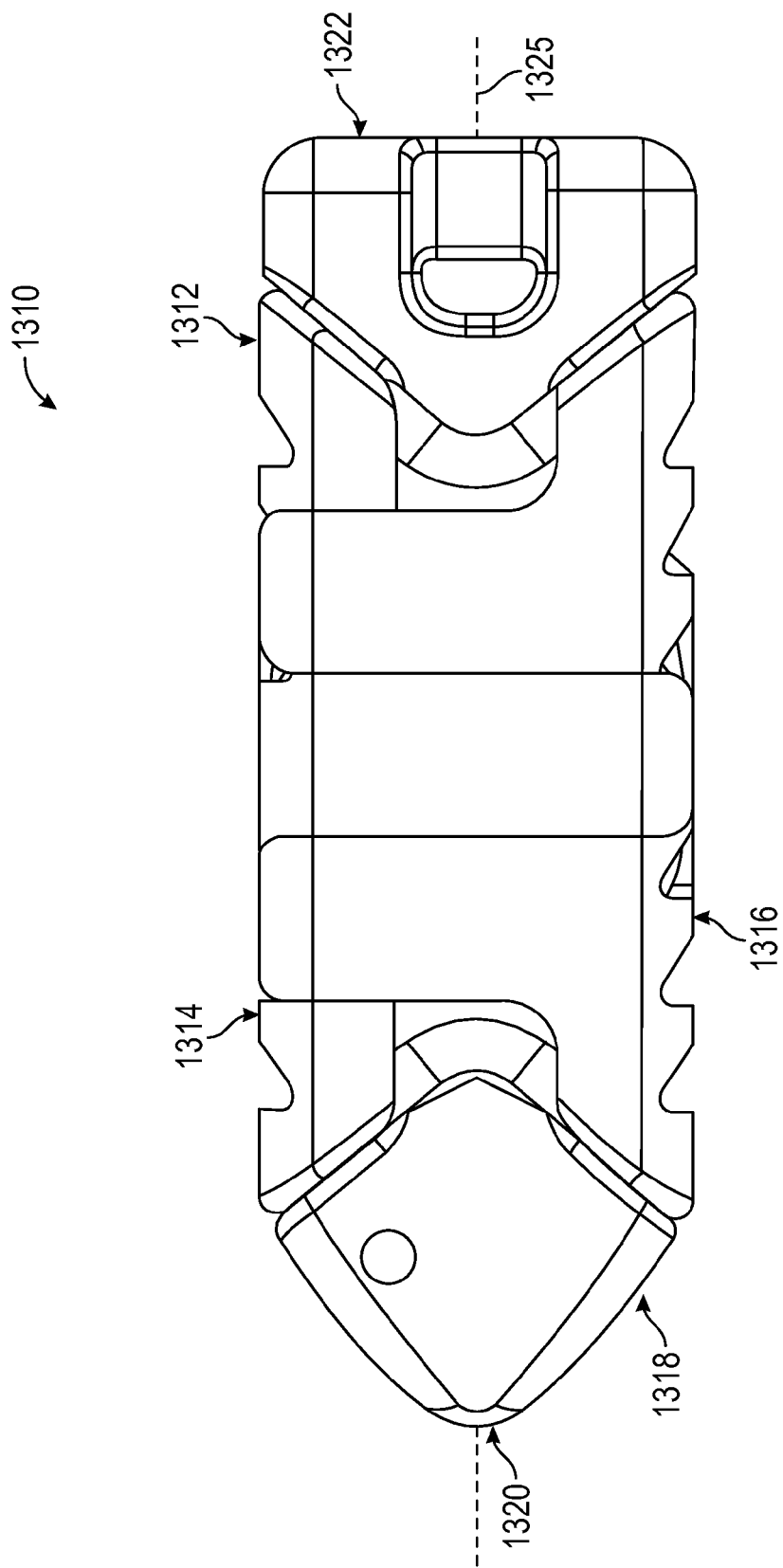
FIG. 114 is a side view of an expandable implant in a contracted configuration according to another exemplary embodiment.
Figure 115:
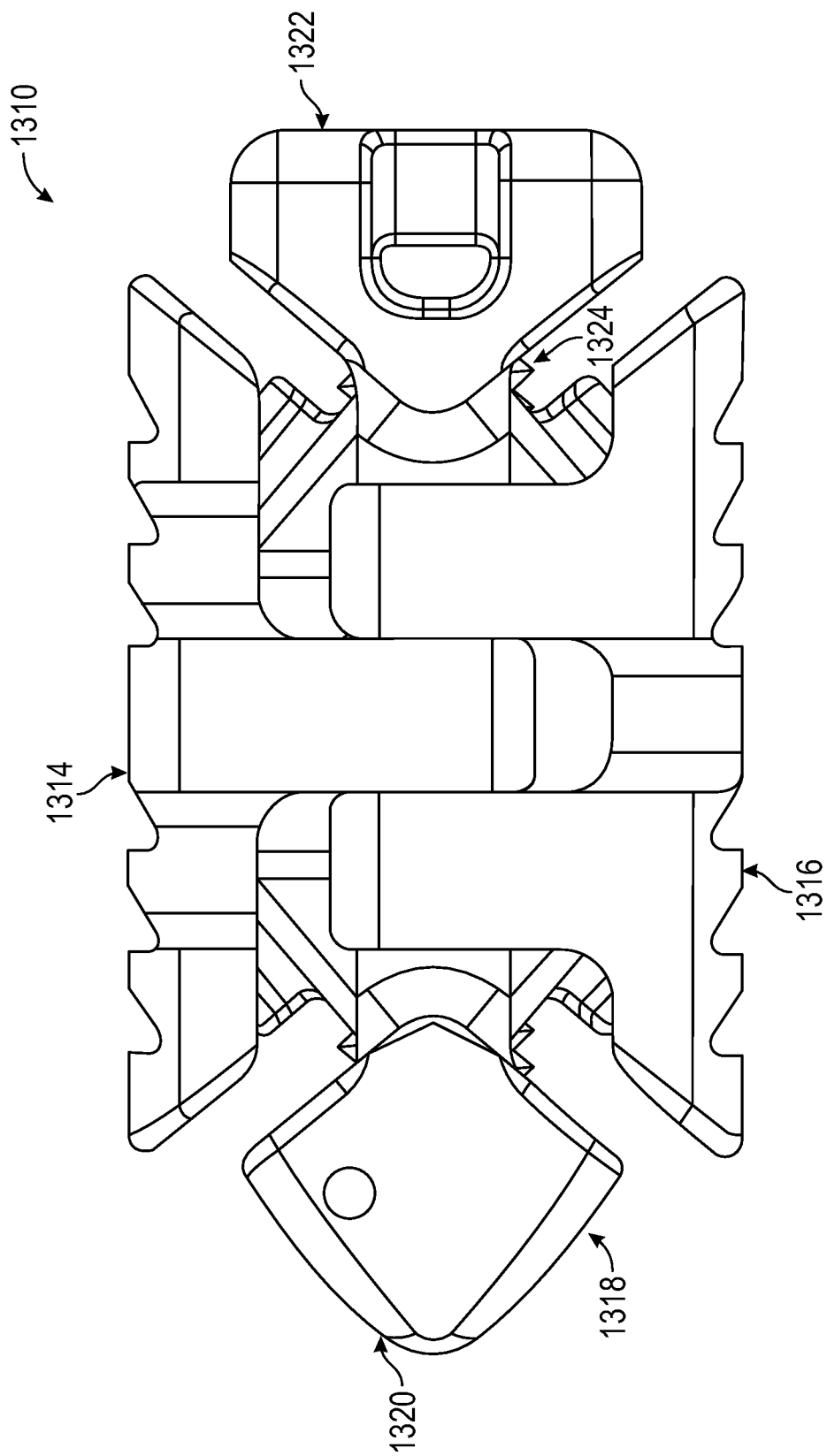
FIG. 115 is a side view of the expandable implant of FIG. 114 in an expanded configuration according to an exemplary embodiment.
Figure 116:
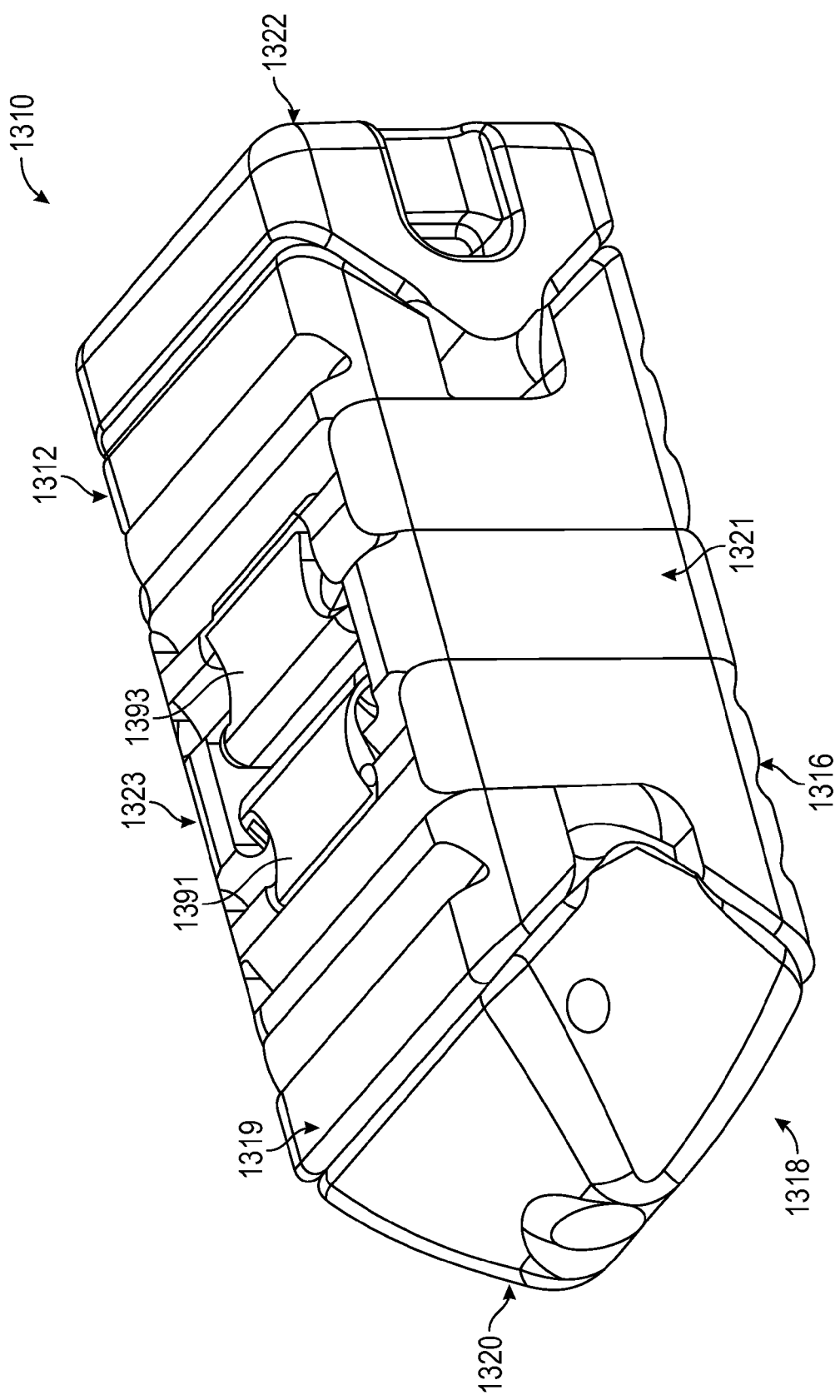
FIG. 116 is a side perspective view of the expandable implant of FIG. 114 in a contracted configuration according to an exemplary embodiment.
Figure 117:
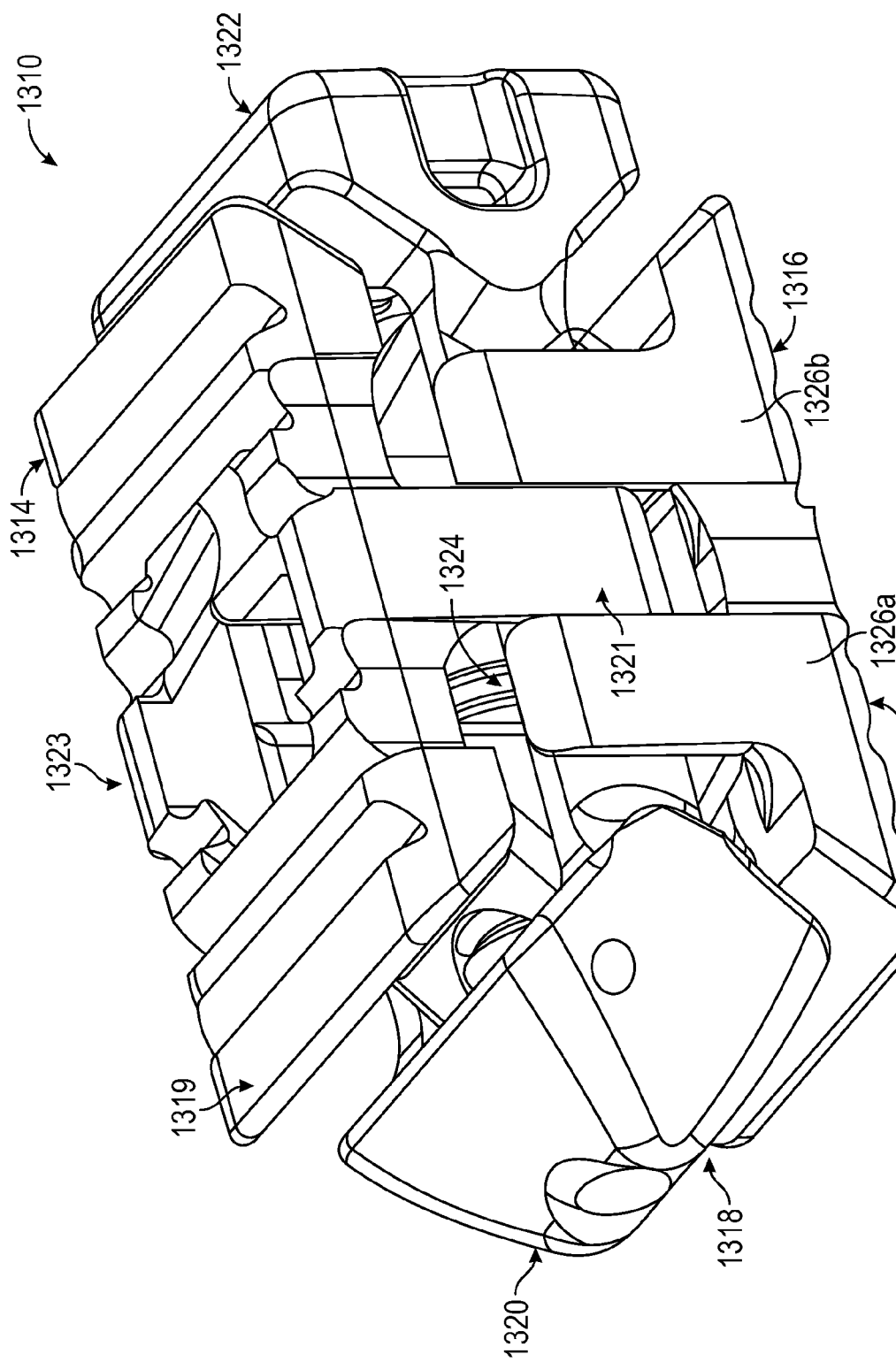
FIG. 117 is a side perspective view of the expandable implant of FIG. 114 in an expanded configuration according to an exemplary embodiment.
Figure 118:
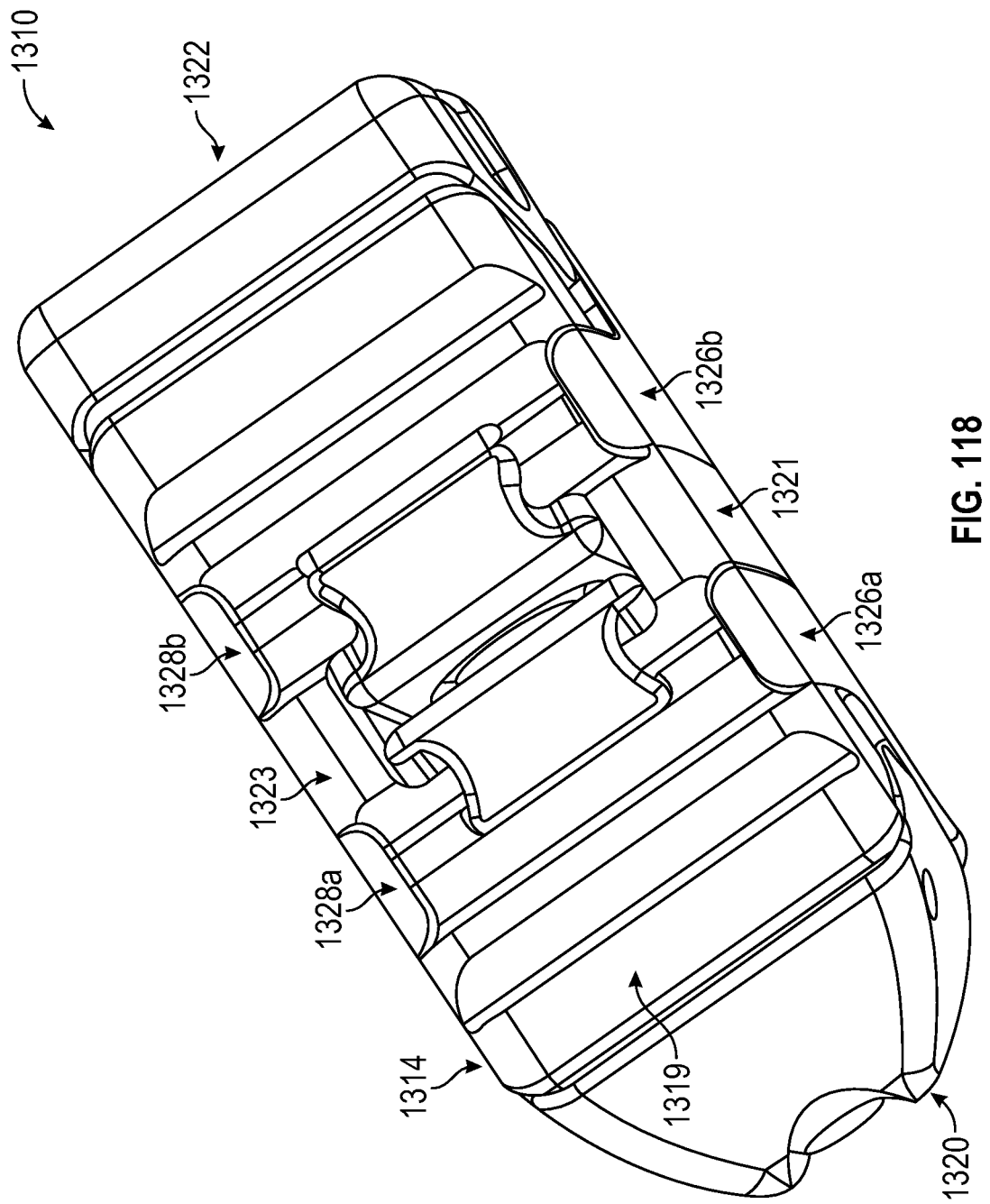
FIG. 118 is a top perspective view of the expandable implant of FIG. 114 in a contracted configuration according to an exemplary embodiment.

As shown in FIGS. 110 and 112, lateral control member 1224 includes a plurality of edges 1232a, 1232b, 1232c, 1232d; lateral control member 1226 includes a plurality of edges 1234a, 1234b, 1234c, 1234d. Top member 1214 includes outer face 1236, and side faces (e.g., sidewalls) 1238, 1240. Bottom member 1216 includes outer face 1242, and side faces (e.g., sidewalls) 1244, 1246. Side face 1238 of top member 1214 and side face 1244 of bottom member 1216 are configured to engage each other and engage lateral control member 1224; side face 1240 of top member 1214 and side face 1246 of bottom member 1216 are configured to engage each other and engage lateral control member 1226 (e.g., side faces 1238, 1244 include cutaway grooves configured to engage a lateral control member and slide along the lateral control member). Vertical edge 1248 of side face 1238 slides along edge 1232a of lateral control member 1224 as top member 1214 expands/contracts. Vertical edge 1250 of side face 1240 slides along edge 1234a of lateral control member 1226 as top member 1214 expands/contracts. Vertical edge 1252 of side face 1244 slides along edge 1232c of lateral control member 1224 as bottom member 1216 expands/contracts. Vertical edge 1254 of side face 1246 slides along edge 1234c of lateral control member 1226 as bottom member 1216 expands/contracts. Lateral control members 1224, 1226 ensure that an angular orientation of top member 1214 or of bottom member 1216 does not change as top member 1214 or bottom member 1216 expands/contracts (e.g., outer face 1236 of top member 1214 and outer face 1242 of bottom member 1216 remain in a same angular orientation—such as being parallel—relative to a longitudinal axis 1225 and lateral control members 1224, 1226, relative to the other outer face, etc.).

Referring now to FIGS. 114-118, an expandable implant 1310 (e.g., an interbody device, an intrabody device, etc.) is shown according to an exemplary embodiment. Implant 1310 is usable, for example, between and/or within vertebral bodies of the spine, and may share many of the features of the other inter/intra-body implants discussed elsewhere herein. However, it should be understood that implant 1310 may have other uses in other portions of a patient's body in addition to the spine (e.g., inside or around bone, such as a femur, as a cement restrictor, etc.). All such applications are understood to be within the scope of the present disclosure. Implant 1310 is generally similar to implants 1110, 1210 in structure and function except with respect to the additional alignment features discussed below.

According to an exemplary embodiment, implant 1310 includes a body assembly 1312 form of a top member 1314, a bottom member 1316, and a central body 1318, central body 1318 including a proximal portion 1320 and a distal portion 1322.

Implant 1310 includes a shaft 1324 configured to be rotated, for example, by rotation of a receiver (see, e.g., receivers 1132 of implant 1110, etc.). Rotation of shaft 1324 expands/contracts members 1314, 1316 in a similar manner as to other implants disclosed herein, such as implants 1110, 1210 through the use of wedge members, etc. For example, similar to implants 1110 and 1210, implant 1310 includes dovetail portions 1391, 1393 prevent the parts of implant 1310 from being separated by merely lifting top member 1314 (e.g., in an upward direction generally perpendicular to longitudinal axis 1325).

Top member 1314 includes an outer face 1319 and central side members 1321, 1323, central side members 1321, 1323 being oriented generally perpendicular to outer face 1319. Bottom member 1316 includes an outer face 1327, a pair of side members 1326a, 1326b disposed on either side of central side member 1321 when implant 1310 is in a closed configuration, and a pair of side members 1328a, 1328b disposed on either side of central side member 1323 when implant 1310 is in a closed configuration. Side members 1328a, 1328b, 1328c, and 1328d are disposed generally perpendicular to outer face 1327 and extend towards top member 1314. As members 1314, 1316 expand/collapse, the interfaces between side members 1321, 1323, and 1326a, 1326b, 1328a, and 1328b ensure that members 1314, 1316 maintain their angular orientation (e.g., members 1314, 1316 maintain an angular orientation in which outer faces 1319, 1327 are parallel to each other and to a plane passing through longitudinal axis 1325 bisecting implant 1310 into a portion containing outer face 1319 and a portion containing outer face 1327).

Figure 119:
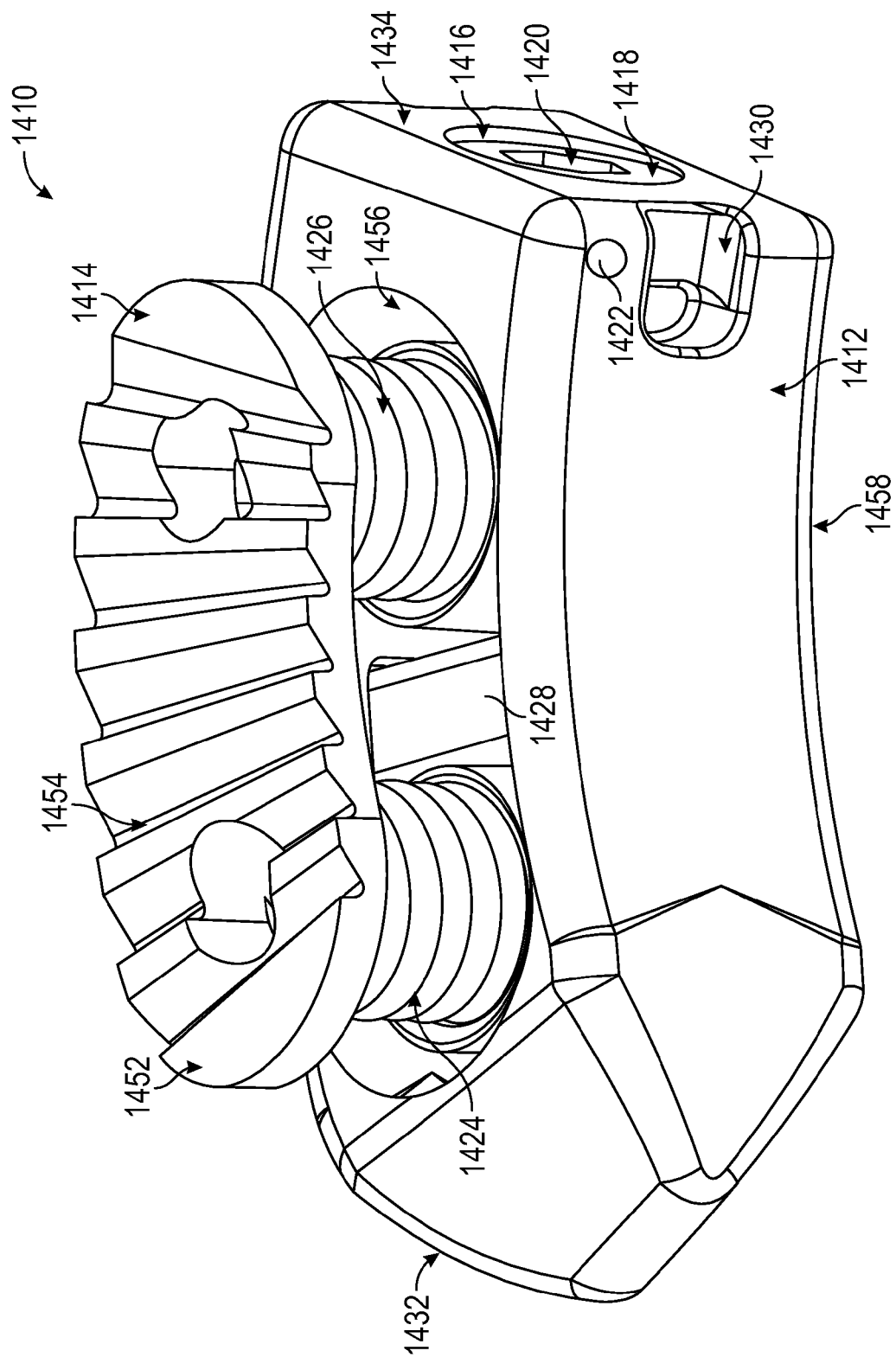
FIG. 119 is perspective view of an expandable implant in an expanded configuration according to another exemplary embodiment.
Figure 120:
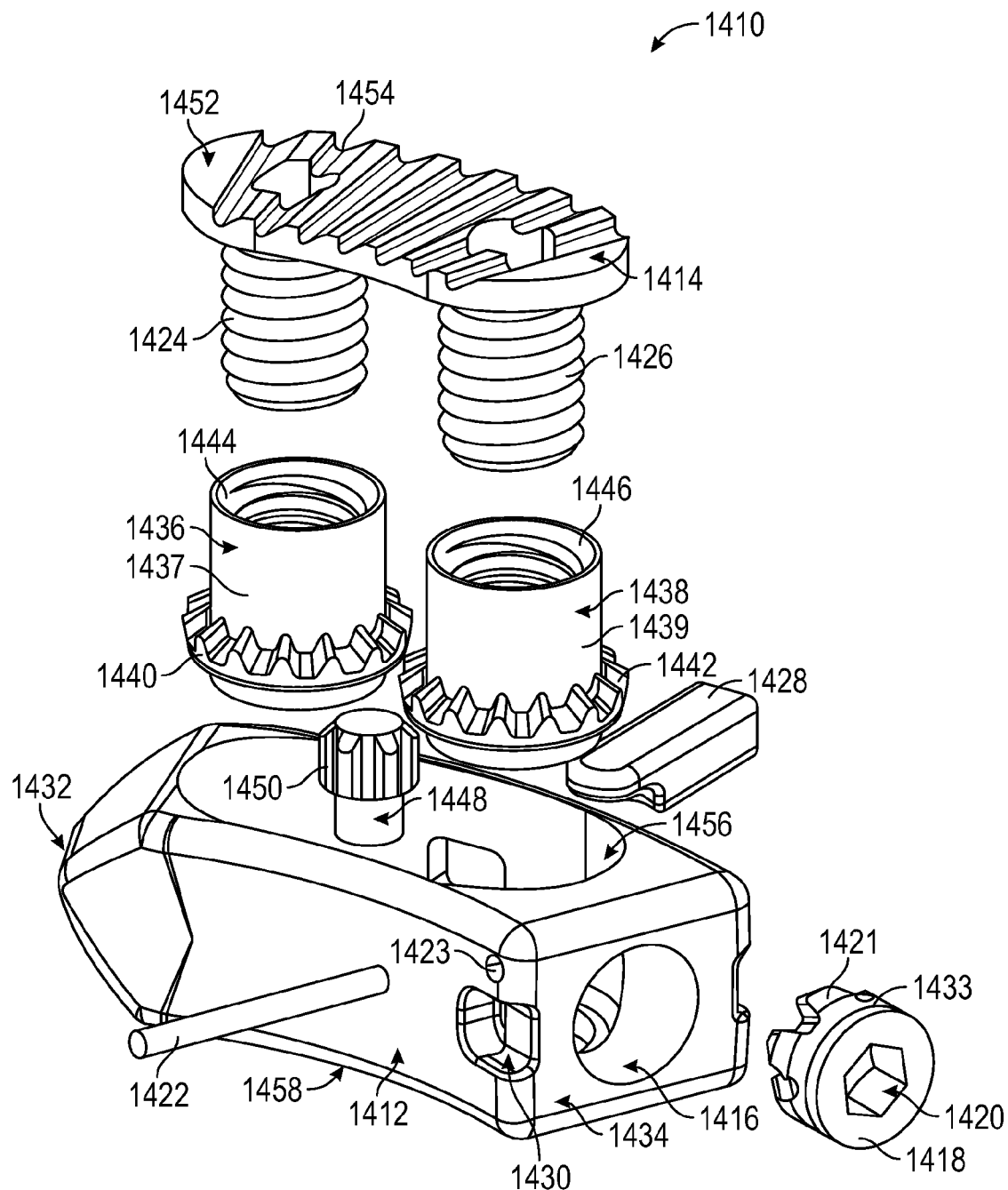
Figure 121:
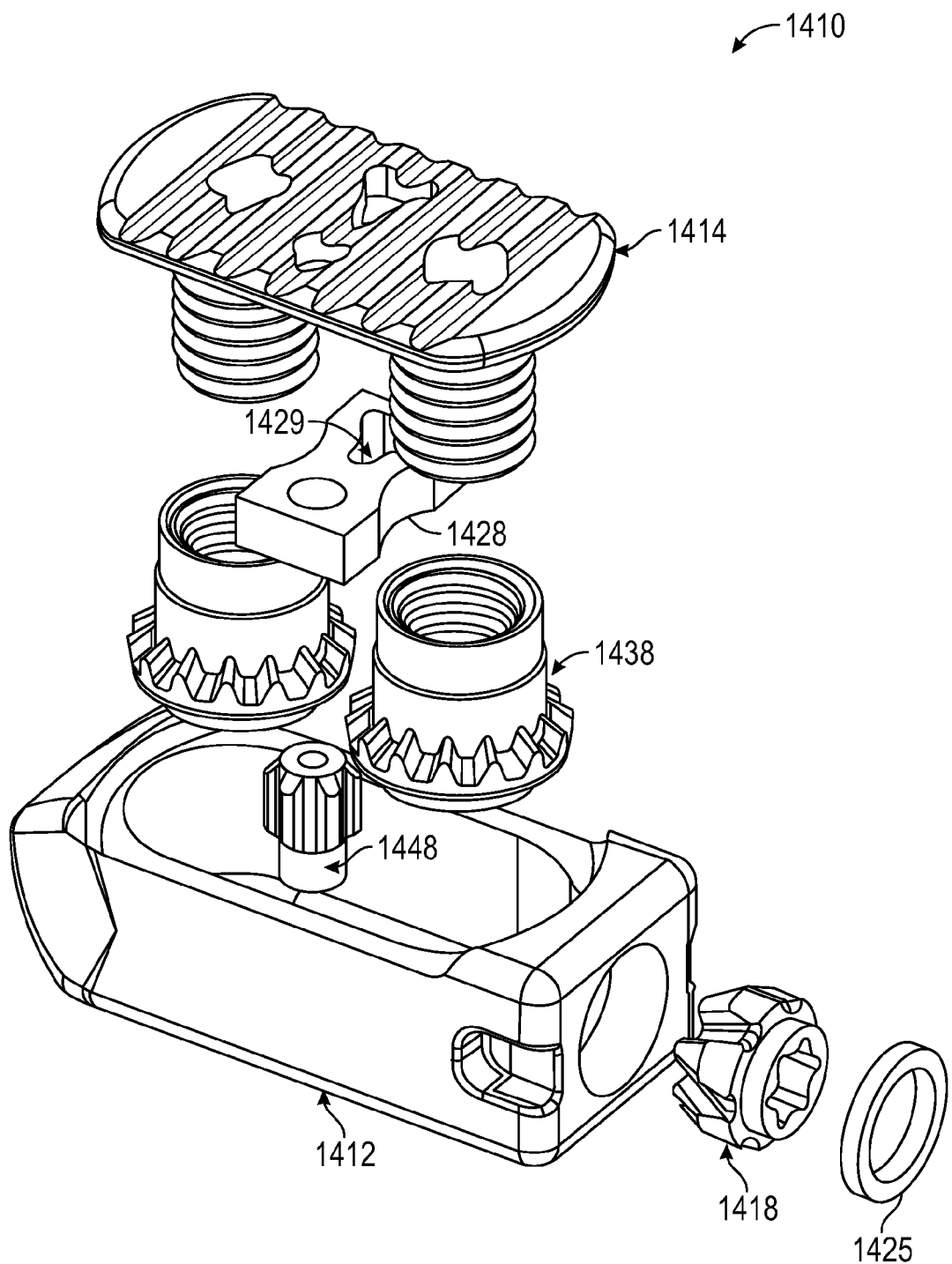

Referring now to FIGS. 119-121, an expandable implant 1310 (e.g., an interbody device, an intrabody device, etc.) is shown according to an exemplary embodiment. Implant 1410 is usable, for example, between and/or within vertebral bodies of the spine, and may share many of the features of the other inter/intra-body implants discussed elsewhere herein. However, it should be understood that implant 1310 may have other uses in other portions of a patient's body in addition to the spine (e.g., inside or around bone, such as a femur, as a cement restrictor, etc.). All such applications are understood to be within the scope of the present disclosure.

According to an exemplary embodiment, implant 1410 includes a body assembly 1412 and a top member 1414 configured to be expanded/contracted (e.g., translated towards/away from implant 1410). Body assembly includes a proximal end 1432 and a distal end 1434. Implant 1410 includes a receiver 1418 disposed within a gap 1416 at distal end 1434 of implant 1410. Receiver 1418 includes a head configured to be rotated by a tool in order to rotate receiver 1418, such as hex head 1420. Receiver 1418 includes a drive gear 1421. Top member 1414 may include grooves 1454 disposed on an outer surface 1452 of top member 1414. While FIGS. 119-120 show grooves 1454 running in a direction generally perpendicular to a curve defined by a longer dimension of outer surface 1452, in various embodiments, grooves 1454 may be configured to run in various directions.

Top member 1414 includes a proximal screw 1424 and a distal screw 1426. Proximal screw 1424 is configured to engage (e.g., threadably couple, screw into, etc.) a proximal gear assembly 1436. Distal screw 1426 is configured to engage (e.g., threadably couple, screw into, etc.) a distal gear assembly 1438. Distal gear assembly 1438 is similar to proximal gear assembly 1436. Proximal gear assembly 1436 includes a proximal gear 1440, a hollow proximal shaft 1437, and a proximal assembly receiver 1444 disposed on an inside surface of proximal shaft 1437. Distal gear assembly 1438 includes a distal gear 1442, a hollow distal shaft 1439, and a distal assembly receiver 1446 disposed on an inside surface of distal shaft 1439. When implant 1410 is assembled, proximal gear assembly 1436 is disposed within body assembly 1412 proximate to proximal end 1432, and distal gear assembly 1438 is disposed within body assembly 1412 proximate to distal end 1434 and engaged to drive gear 1421.

Proximal assembly receiver 1444 is configured to receive (e.g., threadably couple, threadably engage, etc.) proximal screw 1424. For example, as shown in FIG. 120, proximal assembly receiver 1444 has a threadform corresponding to the thread on proximal screw 1424, allowing proximal screw 1424 to be screwed into proximal assembly receiver 1444. As such, proximal gear assembly 1436 is attached to top member 1414 and distal gear assembly 1438 is attached to top member 1414. When proximal assembly receiver 1444 has engaged proximal screw 1424, rotation of proximal gear assembly 1436 causes proximal screw 1424 to be rotated and thus translated into/out of proximal assembly receiver 1444; in turn, top member 1414 is translated towards/away from body assembly 1412. Similarly, when distal assembly receiver 1446 has engaged distal screw 1426, rotation of distal gear assembly 1438 causes distal screw to be rotated and thus translated into/out of proximal assembly receiver 1446; in turn, top member 1414 is translated towards/away from body assembly 1412.

Distal gear 1442 is configured to engage drive gear 1421, such that rotation of receiver 1418 causes rotation of drive gear 1421 and thus distal gear 1442. Distal gear 1442 is also configured to engage a connecting gear 1448. Connecting gear 1448 is disposed within body assembly 1412 between proximal gear assembly 1436 and distal gear assembly 1438. A cover plate 1428 is disposed on a side of connecting gear 1448 proximate to gap 1456. Rotation of distal gear 1442 causes connecting gear 1448 to rotate. Connecting gear 1448 is configured to engage proximal gear 1440. Rotation of connecting gear 1448 causes proximal gear 1440 to rotate. Accordingly, rotation of receiver 1418 causes drive gear 1421, distal gear 1442, connecting gear 1448, and proximal gear 1440 to rotate in unison, in turn rotating proximal screw 1424 and distal screw 1426 in order to expand/contract top member 1414.

In some embodiments, at least some of drive gear 1421, distal gear 1442, connecting gear 1448, proximal gear 1440, proximal screw 1424, and distal screw 1426 have corresponding (e.g., matching, etc.) gear teeth/screw thread orientations. For example, the aforementioned gears and screws may have right-handed teeth/thread orientations, such that rotation of receiver 1418 in a first direction (e.g., clockwise) causes top member 1414 to expand (e.g., translate away from body assembly 1412), and rotation of receiver 1418 in a second direction (e.g., counter-clockwise) causes top member 1414 to contract (e.g., translate towards body assembly 1412). In various embodiments, various combinations of teeth/thread forms may be used for the gears and screws in order to provide various rotational engagements between the gears and screws. In some embodiments, connecting gear 1448 is configured to drive proximal gear 1440 and distal gear 1442 at the same rate. In some embodiments, the gears have straight teeth (e.g., straight-cut teeth that teeth projecting radially).

Implant 1410 includes a drive gear pin 1422 configured to be disposed within a pin gap 1423 of body assembly 1412 and a pin groove 1433 of receiver 1418 (e.g., adjacent to drive gear 1421), such that pin groove 1433 slides along drive gear pin 1422 as receiver 1418 rotates. Drive gear pin 1422 helps ensure that receiver 1418 remains disposed within body assembly 1412. While FIG. 120 shows drive gear pin 1422 disposed proximate to distal end 1434 of body assembly 1412 and proximate to a side of body assembly 1412 at which gap 1456 is disposed, in various embodiments, drive gear pin 1422 may be disposed in various locations (e.g., proximate to a bottom surface 1458 of body assembly 1412).

In some embodiments, body assembly 1412 includes a containment 1430 (e.g., a void, a hollow space, etc.) configured to store material such as bone graft material; containment 1430 may be provided for attaching in instrument to containment 1430 for installation purposes. While FIGS. 119-120 show containment 1430 disposed proximate to distal end 1434 of body assembly 1412, containment 1430 may be disposed on any surface of body assembly 1412.

Referring to FIG. 121, in some embodiments, implant 1410 includes cover plate 1428 as a graft plate or a containment plate or 1428, including a containment 1429 allowing for packing of bone graft material. Cover plate 1428 including containment 1429 may be welded onto an exterior of body assembly 1412. In some embodiments, implant 1410 includes a weld ring 1425. Weld ring 1425 may be used to hold receiver 1418 in body assembly 1412.

As shown in FIGS. 119-120, body assembly 1412 includes a curved profile (e.g., a path travelling from drive gear 1421 through rotational axes defined by rotation of proximal screw 1424 and distal screw 1426 is not straight). In various embodiments (e.g., implant 1410 shown in FIG. 121), body assembly 1412 includes a straight profile (e.g., a path travelling from drive gear 1421 through rotational axes defined by rotation of proximal screw 1424 and distal screw 1426 is straight).

Figure 122:
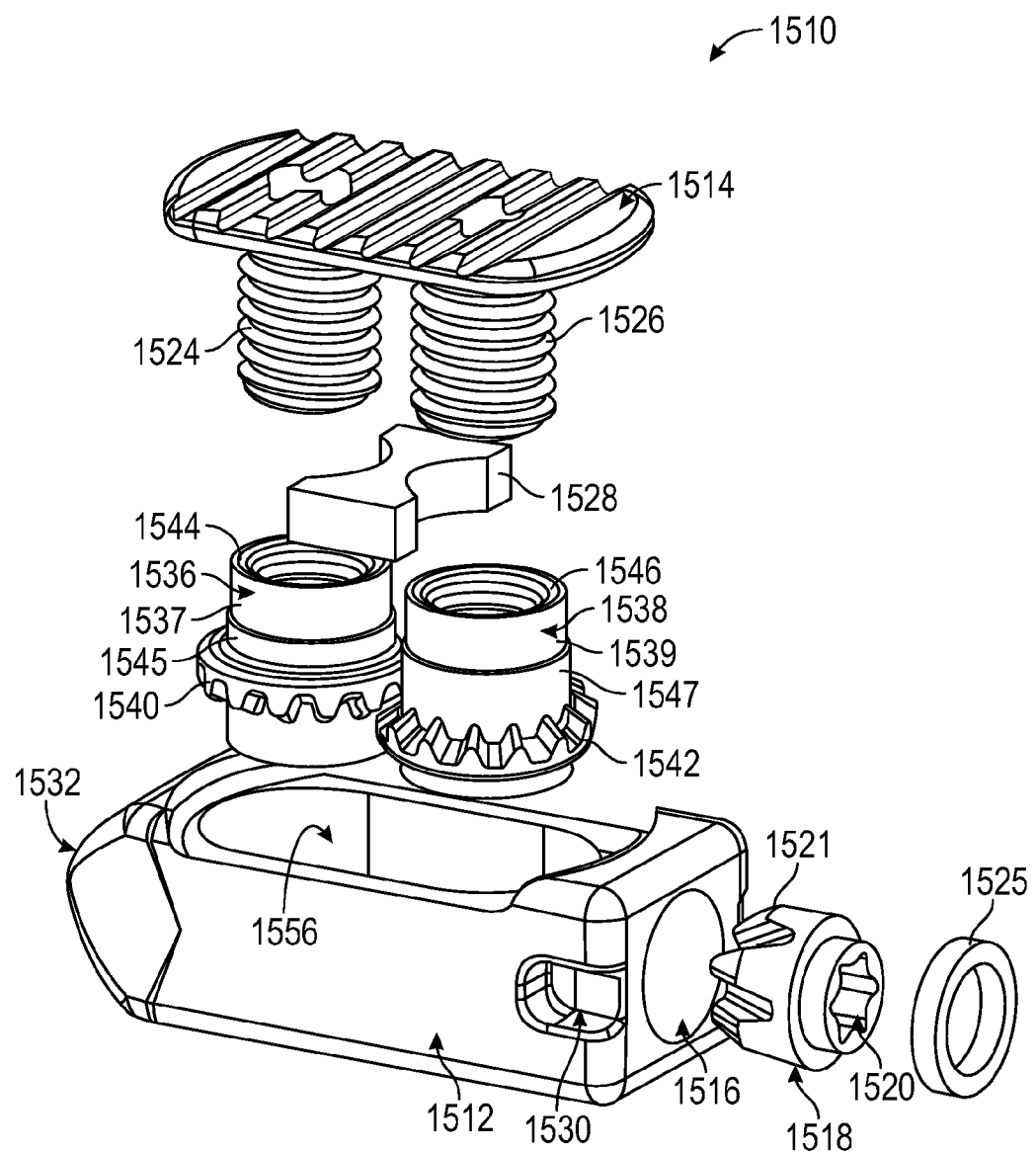
Figure 123:
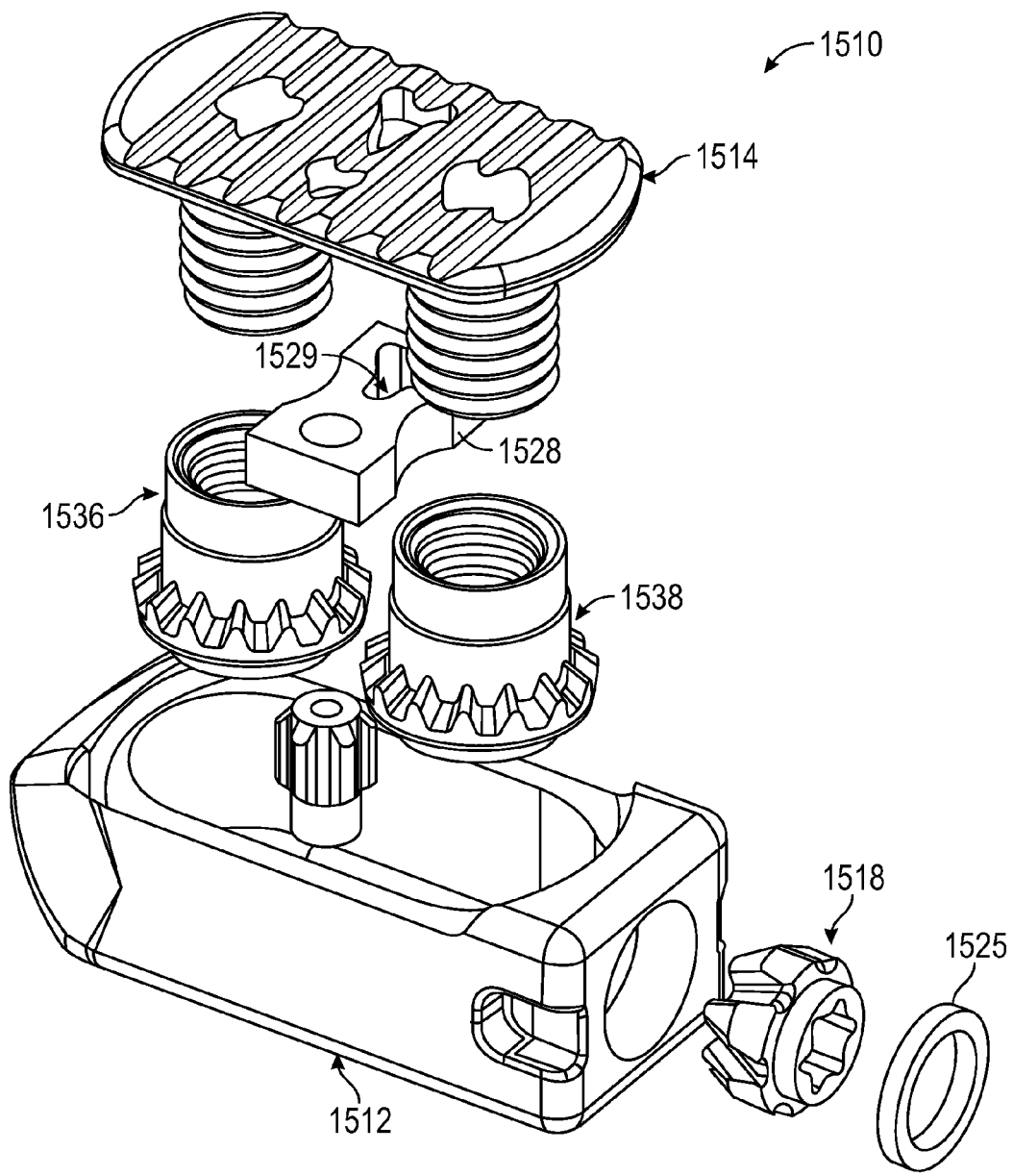

Referring now to FIGS. 122-123, an expandable implant 1510 (e.g., an interbody device, an intrabody device, etc.) is shown according to an exemplary embodiment. Implant 1510 is usable, for example, between and/or within vertebral bodies of the spine, and may share many of the features of the other inter/intra-body implants discussed elsewhere herein. However, it should be understood that implant 1510 may have other uses in other portions of a patient's body in addition to the spine (e.g., inside or around bone, such as a femur, as a cement restrictor, etc.). All such applications are understood to be within the scope of the present disclosure. Implant 1510 is generally similar to implant 1410 in structure and function except with respect to the gear arrangement features discussed below.

According to an exemplary embodiment, implant 1510 includes a body assembly 1512, a top member 1514 configured to be disposed within a gap 1556 of body assembly 1512, and a receiver 1518 configured to be disposed within a gap 1516 of body assembly 1512. Top member 1514 includes a proximal screw 1524 and a distal screw 1526. Proximal screw 1524 is configured to engage a proximal gear assembly 1536, and distal screw 1526 is configured to engage a distal gear assembly 1538. Receiver 1518 includes a head for receiving a tool for rotating receiver 1518, such as hex head 1520. Receiver 1518 includes a drive gear 1521 configured to engage a distal gear 1542 of distal gear assembly 1538. Distal gear 1542 is configured to engage a proximal gear 1540 of proximal gear assembly 1536. As shown in FIG. 122, distal gear 1542 and proximal gear 1540 are provided with opposing gear teeth. The teeth of distal gear 1542 face towards top member 1514, while the teeth of proximal gear 1540 face towards the teeth of distal gear 1542. As such, rotation of distal gear 1542 causes rotation of proximal gear 1540. In some embodiments, drive gear 1421 of receiver 1518 and distal gear 1542 are provided with right-handed gear teeth, while proximal gear 1540 is provided with left-handed gear teeth. In various embodiments, various combinations of turning directions and gear teeth/screw thread forms may be implemented amongst the gears and screws of implant 1510.

Proximal gear assembly 1536 includes a hollow shaft portion with an upper proximal section 1537 having a first proximal shaft radius and a lower proximal section 1545 having a second proximal shaft radius, the second proximal shaft radius being greater than the first proximal shaft radius and proximal gear 1540 being disposed surrounding and coannular with lower proximal section 1545. Distal gear assembly 1538 includes a hollow shaft portion with an upper distal section 1539 having a first distal shaft radius and a lower distal section 1547 having a second distal shaft radius, the second distal shaft radius being greater than the first distal shaft radius and distal gear 1542 being disposed surrounding an coannular with lower distal section 1547. Implant 1510 includes a cover plate 1528. Cover plate 1528 is configured to be disposed between proximal gear assembly 1536 and distal gear assembly 1538, such that curved sides of cover plate 1528 conform to upper proximal section 1537 and upper distal section 1539. Implant 1510 includes a containment 1530 for storing material such as material for a bone graft; containment 1430 may be provided for attaching in instrument to containment 1430 for installation purposes.

Implant 1510 includes weld ring 1525, which is similar to weld ring 1425 shown in FIG. 121. In various embodiments, implant 1510 may be configured to hold receiver 1518 in body assembly 1512 using various implements, such as a drive gear pin similar to drive gear pin 1422 shown in FIGS. 119-120.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. An implant comprising:
    a body assembly;
    a top member configured to fit within a gap in the body assembly;
    a drive gear disposed within the body assembly at a distal end of the body assembly, wherein the drive gear includes a receiver accessible from outside the body assembly, and the receiver is configured to be rotated in order to rotate the drive gear, the drive gear including a plurality of drive gear teeth;
    a distal gear assembly coupled to the top member and engaging the drive gear, the distal gear assembly including a plurality of distal gear teeth disposed perpendicular to and engaged to the drive gear teeth; and
    a proximal gear assembly coupled to the top member and engaging the distal gear assembly, the proximal gear assembly including a plurality of proximal gear teeth disposed opposed to and engaged to the distal gear teeth;
    wherein rotation of the drive gear in a first direction causes the proximal gear assembly and the distal gear assembly to translate the top member away from the body assembly, and rotation of the drive gear in a second direction opposite the first direction causes the gear assemblies to translate the top member towards the body assembly.

2. The implant of claim 1, wherein the body assembly includes a curved profile, the curved profile defined by a path travelling from the drive gear through rotational axes defined by the distal gear assembly and the proximal gear assembly.

3. The implant of claim 1, wherein an outside surface of the body assembly defines a containment configured to store material for a bone graft.

4. The implant of claim 1, further comprising a pin disposed within the body assembly and adjacent to the drive gear; wherein the drive gear includes a groove configured to receive the pin.

5. The implant of claim 1, further comprising a weld ring configured to contain the drive gear.

6. The implant of claim 1, further comprising a cover plate disposed between the proximal gear assembly and distal gear assembly.

7. The implant of claim 1, wherein the proximal gear teeth are one of left-handed or right-handed and the distal gear teeth are the other of left-handed or right-handed.

8. The implant of claim 1, wherein the proximal gear assembly includes a hollow shaft portion including an upper proximal section having a first proximal shaft radius and a lower proximal section having a second proximal shaft radius greater than the first proximal shaft radius, wherein the proximal gear teeth surround the lower proximal section.

9. An implant comprising:
    a body assembly;
    a top member configured to fit within a gap in the body assembly;
    a drive gear disposed within the body assembly at a distal end of the body assembly, wherein the drive gear includes a receiver accessible from outside the body assembly, and the receiver is configured to be rotated in order to rotate the drive gear, the drive gear including a plurality of drive gear teeth;

a distal gear assembly coupled to the top member and engaging the drive gear, the distal gear assembly including a plurality of distal gear teeth disposed perpendicular to and engaged to the drive gear teeth;

a connecting gear disposed on a proximal side of the distal gear assembly, the connecting gear including a plurality of connecting gear teeth engaged to the distal gear teeth; and a proximal gear assembly coupled to the top member and engaging the distal gear assembly, the proximal gear assembly disposed on a proximal side of the connecting gear, the proximal gear assembly including a plurality of proximal gear teeth engaged to the connection gear teeth;

wherein rotation of the drive gear in a first direction causes the proximal gear assembly and the distal gear assembly to translate the top member away from the body assembly, and rotation of the drive gear in a second direction opposite the first direction causes the gear assemblies to translate the top member towards the body assembly.

10. The implant of claim 9, wherein the body assembly further includes a graft plate disposed above the connecting gear, the graft plate including a containment configured to store material for a bone graft.

11. The implant of claim 9, wherein the body assembly includes a curved profile, the curved profile defined by a path travelling from the drive gear through rotational axes defined by the distal gear assembly and the proximal gear assembly.

12. The implant of claim 9, wherein an outside surface of the body assembly defines a containment configured to store material for a bone graft.

13. The implant of claim 9, further comprising a pin disposed within the body assembly and adjacent to the drive gear; wherein the drive gear includes a groove configured to receive the pin.

14. The implant of claim 9, further comprising a weld ring configured to contain the drive gear.

15. The implant of claim 9, further comprising a cover plate disposed between the proximal gear assembly and distal gear assembly.

16. The implant of claim 15, wherein the cover plate includes a containment allowing for placing of bone graft material.

17. The implant of claim 9, wherein the connecting gear teeth are one of left-handed or right-handed and the proximal gear teeth are the other of left-handed or right-handed.

18. The implant of claim 9, wherein the proximal gear assembly includes a proximal assembly receiver that engages a proximal screw of the top member.

* * * * *